US007939654B2

(12) United States Patent
Janjic et al.

(10) Patent No.: US 7,939,654 B2
(45) Date of Patent: *May 10, 2011

(54) PLATELET DERIVED GROWTH FACTOR (PDGF) NUCLEIC ACID LIGAND COMPLEXES

(75) Inventors: Nebojsa Janjic, Boulder, CO (US); Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/512,780

(22) Filed: Jul. 30, 2009

(65) Prior Publication Data

US 2010/0029922 A1 Feb. 4, 2010

Related U.S. Application Data

(60) Continuation of application No. 10/606,159, filed on Jun. 24, 2003, now abandoned, which is a division of application No. 09/851,486, filed on May 8, 2001, now Pat. No. 6,582,918, which is a division of application No. 08/991,743, filed on Dec. 16, 1997, now Pat. No. 6,229,002.

(51) Int. Cl.
*C07H 21/04* (2006.01)
*A61K 31/70* (2006.01)

(52) U.S. Cl. ........................................ 536/24.5; 514/44

(58) Field of Classification Search .................. None
See application file for complete search history.

(56) References Cited

U.S. PATENT DOCUMENTS

| | | | |
|---|---|---|---|
| 4,904,582 A | 2/1990 | Tullis |
| 5,149,794 A | 9/1992 | Yatvin et al. |
| 5,171,217 A | 12/1992 | March et al. |
| 5,245,022 A | 9/1993 | Weis et al. |
| 5,270,163 A | 12/1993 | Gold et al. |
| 5,425,940 A | 6/1995 | Zimmerman et al. |
| 5,459,015 A | 10/1995 | Janjic et al. |
| 5,475,096 A | 12/1995 | Gold et al. |
| 5,562,922 A | 10/1996 | Lambert |
| 5,563,255 A | 10/1996 | Monia et al. |
| 5,593,974 A | 1/1997 | Rosenberg et al. |
| 5,595,877 A | 1/1997 | Gold et al. |
| 5,614,503 A | 3/1997 | Chaudhary et al. |
| 5,631,237 A | 5/1997 | Dzau et al. |
| 5,668,264 A | 9/1997 | Janjic et al. |
| 5,674,685 A | 10/1997 | Gold et al. |
| 5,723,594 A | 3/1998 | Gold et al. |
| 5,756,291 A | 5/1998 | Griffin et al. |
| 5,811,533 A | 9/1998 | Gold et al. |

FOREIGN PATENT DOCUMENTS

| | | |
|---|---|---|
| CA | 2219119 | 11/1996 |
| CA | 2221318 | 12/1996 |
| EP | 0462145 | 12/1991 |
| GB | 2183661 | 6/1987 |
| WO | WO 88/09810 | 12/1988 |
| WO | WO 89/06694 | 7/1989 |
| WO | WO 90/10448 | 9/1990 |
| WO | WO 91/14696 | 10/1991 |
| WO | WO 92/14843 | 9/1992 |
| WO | WO 94/01448 | 1/1994 |
| WO | WO 94/15619 | 7/1994 |
| WO | WO 94/27615 | 12/1994 |
| WO | WO 94/29479 | 12/1994 |
| WO | WO 95/00529 | 1/1995 |
| WO | WO 95/06474 | 3/1995 |
| WO | WO 95/06659 | 3/1995 |
| WO | WO 95/07364 | 3/1995 |
| WO | WO 95/08003 | 3/1995 |
| WO | WO 96/21469 | 7/1996 |
| WO | WO 96/34876 | 11/1996 |
| WO | WO 96/38579 | 12/1996 |

OTHER PUBLICATIONS

De Smidt et al., "Association of antisense oligonucleotides with lipoproteins prolongs the plasma half-life and modifies the tissue distribution," Nucl. Acids Res. 19(17):4695-700 (1991).

Ellington and Szostak, Abstracts of papers presented at the 1990 meeting on RNA Processing, Cold Spring Harbor Laboratory, Cold Spring Harbor, NY, p. 84 (1990).

Ellington, "RNA ligands: out of shape but fir for recognition," Curr. Biol. 3(6):375-7 (1993).

Ferns et al., "Inhibition of neointimal smooth muscle accumulation after angioplasty by an antibody to PDGF," Science 253(5024):1129-32 (1991).

Green et al., "Inhibitory DNA ligands to platelet-derived growth factor B-chain," Biochemistry 35(45):14413-24 (1996).

Jaschke et al., "Synthesis and properties of oligodeoxyribonucleotide-polyethylene glycol conjugates," Nucl. Acids Res. 22(22):4810-7 (1994).

Jellinek et al , "Inhibition of receptor binding by high-affinity RNA ligands to vascular endothelial growth factor," Biochemistry 33(34):10450-6 (1994).

Joyce and Inoue, "A novel technique for the rapid preparation of mutant RNAs," Nucl. Acids Res. 17(2):711-22 (1989).

(Continued)

*Primary Examiner* — Tracy Vivlemore
(74) *Attorney, Agent, or Firm* — Swanson & Bratschun, L.L.C.

(57) ABSTRACT

This invention discloses a method for preparing a complex comprised of a PDGF Nucleic Acid Ligand and a Non-Immunogenic, High Molecular Weight Compound or Lipophilic Compound by identifying a PDGF Nucleic Acid Ligand by SELEX methodology and associating the PDGF Nucleic Acid Ligand with a Non-Immunogenic, High Molecular Weight Compound or Lipophilic Compound. The invention further discloses Complexes comprising one or more PDGF Nucleic Acid Ligands in association with a Non-Immunogenic, High Molecular Weight Compound or Lipophilic Compound. The invention further includes a Lipid construct comprising a PDGF Nucleic Acid Ligand or Complex and methods for making the same.

26 Claims, 26 Drawing Sheets

OTHER PUBLICATIONS

Joyce, "Amplification, mutation and selection of catalytic RNA," Gene 82(1):83-7 (1989).

Kinzler and Vogelstein, "Whole genome PCR: application to the identification of sequences bound by gene regulatory proteins," Nucl. Acids Res. 17(10):3645-53 (1989).

Kramer et al., "Evolution in vitro: sequence and phenotype of a mutant RNA resistant to ethidium bromide," J. Mol. Biol. 89(4):719-36 (1974).

Levisohn and Spiegelman, "Further extracellular Darwinian experiments with replicating RNA molecules: diverse variants isolated under different selective conditions," PNAS USA 63(3):805-811 (1969).

Levisohn and Spiegelman, "The cloning of a self-replicating RNA molecule," PNAS USA 60(3):866-72 (1968).

Mackellar et al., "Synthesis and physical properties of anti-HIV antisense oligonucleotides bearing terminal lipophilic groups," Nucl. Acids Res. 20(13):3411-7 (1992).

Maresta et al., "Trapidil (triazolopyrimidine), a platelet-derived growth factor antagonist, reduces restenosis after percutaneous transluminal coronary angioplasty. Results of the randomized, double-blind STARC study. Studio Trapidil versus Aspirin nella Restenosi Coronarica," Circulation 90(6):2710-5 (1994).

Nucci et al., "The therapeutic value of poly(ethylene glycol)-modified proteins," Adv. Drug Del. Rev. 6:133-151 (1991).

Ohta et al., "Suppressive effect of antisense DNA of platelet-derived growth factor on murine pulmonary fibrosis with silica particles," Chest 111(6 Suppl):105S (1997).

Oliphant and Struhl, "Defining the consensus sequences of E.coli promoter elements by random selection," Nucl. Acids Res. 16(15):7673-83 (1988).

Oliphant and Struhl, "The use of random-sequence oligonucleotides for determining consensus sequences," Meth. Enzymol. 155:568-82 (1987).

Oliphant et al., "Cloning of random-sequence oligodeoxynucleotides," Gene 44(2-3):177-83 (1986).

Oliphant et al., "Defining the sequence specificity of DNA-binding proteins by selecting binding sites from random-sequence oligonucleotides: analysis of yeast GCN4 protein," Mol. Cell Biol. 9(7):2944-9 (1989).

Robertson and Joyce, "Selection in vitro of an RNA enzyme that specifically cleaves single-stranded DNA," Nature 344(6265):467-8 (1990).

Shea et al. "Synthesis, hybridization properties and antiviral activity of lipid-oligodeoxynucleotide conjugates," Nucl. Acids Res. 18(13):3777-83 (1990).

Stull and Szoka, "Antigene, ribozyme and aptamer nucleic acid drugs: progress and prospects," Pharm Res. 12(4):465-83 (1995).

Szostak, "Structure, and activity of ribozymes," in Redesigning the Molecules of Life, Benner, S.A., ed. (Heidelberg: Springer-Verlag) pp. 87-113 (1988).

Thiesen and Bach, "Target Detection Assay (TDA): a versatile procedure to determine DNA binding sites as demonstrated on SP1 protein," Nucl. Acids Res. 18(11):3203-9 (1990).

Veronese and Pasut, "PEGylation, successful approach to drug delivery," Drug Discov. Today. 10(21):1451-8 (2005).

Helix I

SEQ ID NO: 82

```
              C   C
           A C   A C
          C G A T A
       G A   T   G
      G   C   C
    T     G-C
   C       G-C
   T       A-T
   A       C-G
   G       A-T
 G G C     5' C-G [3'T]
C C G
         SEQ ID NO: 84
           FIGURE 2B
```

36t

```
             G   A G C
          G C A A G T A
         G A   T   T
       A G   C   G
      T     G-C
    C       G-C
   T        G-C
   C        T A
   A         A
  T
 A
[3'T]A T     5' 
```

41t

SEQ ID NO: 85
FIGURE 2C

```
         T
       C T T T
      C G T   T
    T   G   C T
   T     T A
  T G C   G-C
     C G   G-C
      C     G-C
   5' TGGGA G-C G [3'T]
```

20t

SEQ ID NO: 83
FIGURE 2A

$K_d = 0.065$ nM

SEQ ID NO: 86

$K_d = 0.097$ nM

NX21568

SEQ ID NO: 87

SEQ ID NO: 145

NX31975 40K PEG
SEQ ID NO: 146

NX31976 40K PEG
SEQ ID NO: 147

Hexaethylene glycol spacer phosphoramidite

Pentyl amino linker

40K PEG NHS ester

US 7,939,654 B2

PLATELET DERIVED GROWTH FACTOR (PDGF) NUCLEIC ACID LIGAND COMPLEXES

RELATED APPLICATIONS

This application is a Continuation of U.S. patent application Ser. No. 10/606,159, filed Jun. 24, 2003, which is a Divisional of U.S. patent application Ser. No. 09/851,486, filed May 8, 2001, now U.S. Pat. No. 6,582,918, which is a Divisional of U.S. patent application Ser. No. 08/991,743, filed Dec. 16, 1997, now U.S. Pat. No. 6,229,002, each of which is incorporated by reference herein in its entirety.

FIELD OF THE INVENTION

Described herein are high affinity ssDNA and RNA ligands to platelet derived growth factor (PDGF). The method utilized herein for identifying such Nucleic Acid Ligands is called SELEX, an acronym for Systematic Evolution of Ligands by Exponential enrichment. Further included in this invention is a method for preparing a therapeutic or diagnostic Complex comprised of a PDGF Nucleic Acid Ligand and a Non-Immunogenic, High Molecular Weight Compound or a Lipophilic Compound by identifying a PDGF Nucleic Acid Ligand by SELEX methodology and covalently linking the PDGF Nucleic Acid Ligand with a Non-Immunogenic, High Molecular Weight Compound or a Lipophilic Compound. The invention further includes Complexes comprised of one or more PDGF Nucleic Acid Ligands and a Non-Immunogenic, High Molecular Weight Compound or a Lipophilic Compound. The invention further relates to improving the Pharmacokinetic Properties of a PDGF Nucleic Acid Ligand by covalently linking the PDGF Nucleic Acid Ligand with a Non-Immunogenic, High Molecular Weight Compound or Lipophilic Compound to form a Complex. The invention further relates to improving the Pharmacokinetic Properties of a PDGF Nucleic Acid Ligand by using a Lipid Construct comprising a PDGF Nucleic Acid Ligand or a Complex comprising a PDGF Nucleic Acid Ligand and a Non-Immunogenic, High Molecular Weight Compound or Lipophilic Compound. This invention further relates to a method for targeting a therapeutic or diagnostic agent to a biological target that is expressing PDGF by associating the agent with a Complex comprised of a PDGF Nucleic Acid Ligand and a Lipophilic Compound or Non-Immunogenic, High Molecular Weight Compound, wherein the Complex is further associated with a Lipid Construct and the PDGF Nucleic Acid Ligand is further associated with the exterior of the Lipid Construct.

BACKGROUND OF THE INVENTION

A. The SELEX Process

The dogma for many years was that nucleic acids had primarily an informational role. Through a method known as Systematic Evolution of Ligands by Exponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, and U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is specifically incorporated by reference herein. Each of these applications, collectively referred to herein as the SELEX patent applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule. SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S.

Pat. No. 5,580,737, describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by Exponential Enrichment: Solution SELEX," now U.S. Pat. No. 5,567,588, describes a SELEX-based method which achieves highly efficient partitioning between oligonucleotides having high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled Nucleic Acid Ligand Complexes," now U.S. Pat. No. 6,011,020. VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228. VEGF Nucleic Acid Ligands that are associated with a Lipophilic Compound, such as a glycerol lipid, or a Non-Immunogenic, High Molecular Weight Compound, such as polyethylene glycol, are further described in U.S. patent application Ser. No. 08/897,351, filed Jul. 21, 1997, entitled "Vascular Endothelial Growth Factor (VEGF) Nucleic Acid Ligand Complexes," now U.S. Pat. No. 6,051,698. VEGF Nucleic Acid Ligands that are associated with a non-immunogenic, high molecular weight compound or lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

B. Lipid Constructs

Lipid Bilayer Vesicles are closed, fluid-filled microscopic spheres which are formed principally from individual molecules having polar (hydrophilic) and non-polar (lipophilic) portions. The hydrophilic portions may comprise phosphate, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into small or Unilamellar Vesicles (UV), with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies, see, for example, U.S. Pat. Nos. 5,019,369, 5,441,745, or 5,435,989.

An area of development aggressively pursued by researchers is the delivery of agents not only to a specific cell type but into the cell's cytoplasm and, further yet, into the nucleus. This is particularly important for the delivery of biological agents such as DNA, RNA, ribozymes and proteins. A promising therapeutic pursuit in this area involves the use of antisense DNA and RNA oligonucleotides for the treatment of disease. However, one major problem encountered in the effective application of antisense technology is that oligonucleotides in their phosphodiester form are quickly degraded in body fluids and by intracellular and extracellular enzymes, such as endonucleases and exonucleases, before the target cell is reached. Intravenous administration also results in rapid clearance from the bloodstream by the kidney, and uptake is insufficient to produce an effective intracellular drug concentration. Liposome encapsulation protects the oligonucleotides from the degradative enzymes, increases the circulation half-life and increases uptake efficiency as a result of phagocytosis of the Liposomes. In this way, oligonucleotides are able to reach their desired target and to be delivered to cells in vivo.

A few instances have been reported where researchers have attached antisense oligonucleotides to Lipophilic Compounds or Non-Immunogenic, High Molecular Weight Compounds. Antisense oligonucleotides, however, are only effective as intracellular agents. Antisense oligodeoxyribonucleotides targeted to the epidermal growth factor (EGF) receptor have been encapsulated into Liposomes linked to folate via a polyethylene glycol spacer (folate-PEG-Liposomes) and delivered into cultured KB cells via folate receptor-mediated endocytosis (Wang et al. (1995) Proc. Natl. Acad. Sci. USA 92:3318-3322). In addition, alkylene diols have been attached to oligonucleotides (Weiss et al. U.S. Pat. No. 5,245,022). Furthermore, a Lipophilic Compound covalently attached to an antisense oligonucleotide has been demonstrated in the literature (EP 462 145 B1).

Loading of biological agents into liposomes can be accomplished by inclusion in the lipid formulation or loading into preformed liposomes. Passive anchoring of oligopeptide and oligosaccharide ligands to the external surface of liposomes has been described (Zalipsky et al. (1997) Bioconjug. Chem. 8:111:118).

C. PDGF

Platelet-derived growth factor (PDGF) was originally isolated from platelet lysates and identified as the major growth-promoting activity present in serum but not in plasma. Two homologous PDGF isoforms have been identified, PDGF A and B, which are encoded by separate genes (on chromosomes 7 and 22). The most abundant species from platelets is the AB heterodimer, although all three possible dimers (AA, AB and BB) occur naturally. Following translation, PDGF dimers are processed into ~30 kDa secreted proteins. Two cell surface proteins that bind PDGF with high affinity have been identified, α and β (Heldin et al. (1981) Proc. Natl. Acad. Sci., 78: 3664; Williams et al. (1981) Proc. Natl. Acad. Sci., 79: 5867). Both species contain five immunoglobulin-like extracellular domains, a single transmembrane domain and an intracellular tyrosine kinase domain separated by a kinase insert domain. The functional high affinity receptor is a dimer and engagement of the extracellular domain of the receptor by PDGF results in cross-phosphorylation (one receptor tyrosine kinase phosphorylates the other in the dimer) on several tyrosine residues. Receptor phosphorylation leads to a cascade of events that results in the transduction of the mitogenic or chemotactic signal to the nucleus. For example, in the intracellular domain of the PDGF β receptor, nine tyrosine residues have been identified that when phosphorylated interact with different src-homology 2 (SH2) domain-containing proteins including phospholipase C-g, phosphatidylinositol 3'-kinase, GTPase-activating protein and several adapter molecules like Shc, Grb2 and Nck (Heldin (1995) Cell 80: 213). In the last several years, the specificities of the three PDGF isoforms for the three receptor dimers ($\alpha\alpha$, $\alpha\beta$, and $\beta\beta$) has been elucidated. The α-receptor homodimer binds all three PDGF isoforms with high affinity, the β-receptor homodimer binds only PDGF BB with high affinity and PDGF AB with approximately 10-fold lower affinity, and the αβ-receptor heterodimer binds PDGF BB and PDGF AB with high affinity (Westermark & Heldin (1993) Acta Oncologica 32:101). The specificity pattern results from the ability of the A-chain to bind only to the α-receptor and of the B-chain to bind to both α and β-receptor subunits with high affinity.

The role of PDGF in proliferative diseases, such as cancer, restenosis, fibrosis, angiogenesis, and wound healing has been established.

PDGF in Cancer

The earliest indication that PDGF expression is linked to malignant transformation came with the finding that the amino acid sequence of PDGF-B chain is virtually identical to that of $p28^{sis}$, the transforming protein of the simian sarcoma virus (SSV) (Waterfield et al. (1983) Nature 304:35; Johnsson et al. (1984) EMBO J. 3:921). The transforming potential of the PDGF-B chain gene and, to a lesser extent, the PDGF-A gene was demonstrated soon thereafter (Clarke et al. (1984) Nature 308:464; Gazit et al. (1984) Cell 39:89; Beckmann et al. Science 241:1346; Bywater et al. (11988) Mol. Cell. Biol. 8:2753). Many tumor cell lines have since been shown to produce and secrete PDGF, some of which also express PDGF receptors (Raines et al. (1990) *Peptide Growth Factors and Their Receptors*, Springer-Verlag, Part 1, p 173). Paracrine and, in some cell lines, autocrine growth stimulation by PDGF is therefore possible. For example, analysis of biopsies from human gliomas has revealed the existence of two autocrine loops: PDGF-B/β-receptor in tumor-associated endothelial cells and PDGF-A/α-receptor in tumor cells (Hermansson et al. (1988) Proc. Natl. Acad. Sci. 85:7748; Hermansson et al. (1992) Cancer Res. 52.3213). The progression to high grade glioma was accompanied by the increase in expression of PDGF-B and the β-receptor in tumor-associated endothelial cells and PDGF-A in glioma cells. PDGF overexpression may thus promote tumor growth either by directly stimulating tumor cells or by stimulating tumor-associated stromal cells (e.g., endothelial cells). The proliferation of endothelial cells is a hallmark of angiogenesis. Increased expression of PDGF and/or PDGF receptors has also been observed in other malignancies including fibrosarcoma (Smits et al. (1992) Am. J. Pathol. 140:639) and thyroid carcinoma (Heldin et al. (1991) Endocrinology 129:2187).

PDGF in Cardiovascular Disease

Percutaneous transluminal coronary angioplasty (PTCA) has become the most common treatment for occlusive coronary artery disease (CAD) involving one or two coronary arteries. In the United States alone about 500,000 procedures are being done annually, with projections of over 700,000 procedures by the year 2000 and about double those amounts worldwide. PTCA, while it involves manipulations inside of coronary arteries, is not considered to be a cardiac surgical intervention. During the most common PTCA procedure, a balloon catheter is threaded through a femoral artery and is positioned within the plaque-laden segment of an occluded coronary vessel; once in place, the balloon is expanded at high pressure, compressing the plaque and increasing the vessel lumen. Unfortunately, in 30-50% of PTCA procedures, reocclusion gradually develops over a period of several weeks or months due to cellular events in the affected vessel wall. Once reocclusion achieves 50% or greater reduction of the original vessel lumen, clinical restenosis is established in the vessel.

In view of the increasing popularity of coronary angioplasty as a less invasive alternative to bypass surgery, restenosis is a serious medical problem. Smooth muscle cells (SMCs) represent a major component of the restenosis lesions. In uninjured arteries, SMCs reside primarily in the medial vessel layer (tunical media). Upon balloon injury that removes the endothelial cells from the intimal layer (tunical intima), SMCs proliferate and migrate into the intima, forming neointimal thickening characteristic of restenosis lesions. When restenosis occurs subsequent to angioplasty, it is usually treated by repeat angioplasty, with or without placement of a stent, or by vascular graft surgery (bypass).

A stent is a rigid cylindrical mesh that, once placed and expanded within a diseased vessel segment, mechanically retains the expanded vessel wall. The stent is deployed by catheter and, having been positioned at the desired site, is expanded in situ by inflation of a high pressure balloon. Being rigid and non-compressible, the expanded stent achieves and maintains a vessel lumen diameter comparable to that of adjacent non-diseased vessel; being pressed tightly into the overlying intima/media, it is resistant to migration within the vessel in response to blood flow. PTCA with stent placement has been compared with PTCA alone and shown to reduce restenosis to about half and to significantly improve other clinical outcomes such as myocardial infarction (MI) and need for bypass surgery.

There is now considerable evidence that PDGF B-chain is a major contributor to the formation of neointimal lesions. In a rat model of restenosis, the neointimal thickening was inhibited with anti-PDGF-B antibodies (Ferns (1991) Science 253:1129-1132; Rutherford et al. (1997) Atherosclerosis 130:45-51). Conversely, the exogenous administration of PDGF-BB promotes SMC migration and causes an increase in neointimal thickening (Jawien et al. (1992) J. Clin. Invest. 89:507-511). The effect of PDGF-B on SMCs is mediated through PDGF β-receptor which is expressed at high levels in these cells after balloon injury (Lindner and Reidy (1995) Circulation Res. 76:951-957). Furthermore, the degree of neointimal thickening following balloon injury was found to be inversely related to the level of expression of PDGF β-receptor at the site of injury (Sirois et al. (1997) Circulation 95:669-676).

U.S. Pat. No. 5,171,217 discloses a method and composition for delivery of a drug to an affected intramural site for sustained release in conjunction with or following balloon catheter procedures, such as angioplasty. The drug may be selected from a variety of drugs known to inhibit smooth muscle cell proliferation, including growth factor receptor antagonists for PDGF.

U.S. Pat. No. 5,593,974 discloses methods for treating vascular disorders, such as vascular restenosis, with antisense oligonucleotides. The method is based on localized application of the antisense oligonucleotides to a specific site in vivo. The oligonucleotides can be applied directly to the target tissue in a mixture with an implant or gel, or by direct injection or infusion.

U.S. Pat. No. 5,562,922 discloses a method for preparing a system suitable for localized delivery of biologically active compounds to a subject. The method relates to treating polyurethane coated substrate with a coating expansion solution under conditions that will allow penetration of the biologically active compound throughout the polyurethane coating.

Substrates suitable for this invention include, inter alia, metallic stents. Biologically active compounds suitable for use in this invention include, inter alia, lipid-modified oligonucleotides.

Rutherford et al. (1997, Atherosclerosis 130:45-51) report substantial inhibition of neointimal response to balloon injury in rat carotid artery using a combination of antibodies to PDGF-BB and basic fibroblast growth factor (bFGF).

PDGF in Renal Disease

A large variety of progressive renal diseases are characterized by glomerular mesangial cell proliferation and matrix accumulation (Slomowitz et al. (11988) New Eng. J. Med. 319:1547-1548) which leads to fibrosis. PDGF B-chain appears to have a central role in driving both of these processes given that 1) mesangial cells produce PDGF in vitro and various growth factors induce mesangial proliferation via induction of auto- or paracrine PDGF B-chain synthesis; 2) PDGF B-chain and its receptor are overexpressed in many glomerular diseases; 3) infusion of PDGF-BB or glomerular transfection with a PDGF B-chain cDNA can induce selective mesangial cell proliferation and matrix accumulation in vivo; and 4) PDGF B-chain or β-receptor knock-out mice fail to develop a mesangium (reviewed in Floege and Johnson (1995) Miner. Electrolyte Metab. 21:271-282). In addition to contributing to kidney fibrosis, PDGF is also believed to play a role in fibrosis development in other organs such as lungs and bone marrow and may have other possible disease associations (Raines et al. (1990) *Experimental Pharmacology, Peptide Growth Factors and Their Receptors*, Sporn & Roberts, eds., pp. 173-262, Springer, Heidelberg).

One study has examined the effect of inhibition of PDGF B-chain in renal disease: Johnson et al., using a neutralizing polyclonal antibody to PDGF, were able to reduce mesangial cell proliferation and matrix accumulation in experimental mesangioproliferative glomerulonephritis (Johnson et al (1992) J. Exp. Med. 175:1413-1416). In this model, injection of an anti-mesangial cell antibody (anti-Thy 1.1) into rats resulted in complement-dependent lysis of the mesangial cells, followed by an overshooting reparative phase that resembled human mesangioproliferative nephritis (Floege et al. (1993) Kidney Int. Suppl. 39:S47-54). Limitations of the study of Johnson et al. (Johnson et al. (11992) J. Exp. Med. 175:1413-1416) included the necessity to administer large amounts of heterologous IgG and a limitation of the study duration to 4 days due to concerns that the heterologous IgG might elicit an immune reaction.

Inhibition of PDGF

Specific inhibition of growth factors, such as PDGF, has become a major goal in experimental and clinical medicine. However, this approach is usually hampered by the lack of specific pharmacological antagonists. Available alternative approaches are also limited, since neutralizing antibodies often show a low efficacy in vivo and are usually immunogenic, and given that in vivo gene therapy for these purposes is still in its infancy. Currently, antibodies to PDGF (Johnsson et al. (1985) Proc. Natl. Acad. Sci. U.S.A. 82:1721-1725; Ferns et al. (1991) Science 253:1129-1132; Herren et al. (1993) Biochimica et Biophysica Acta 1173:294-302; Rutherford et al. (1997) Atherosclerosis 130:45-51) and the soluble PDGF receptors (Herren et al. (1993) Biochimica et Biophysica Acta 1173:294-302; Duan et al. (1991) J. Biol. Chem. 266:413-418; Teisman et al. (1993) J. Biol. Chem. 268:9621-9628) are the most potent and specific antagonists of PDGF. Neutralizing antibodies to PDGF have been shown to revert the SSV-transformed phenotype (Johnsson et al. (1985) Proc. Natl. Acad. Sci. U.S.A. 82:1721-1725) and to inhibit the development of neointimal lesions following arterial injury (Ferns et al. (1991) Science 253:1129-1132). Other inhibitors of PDGF such as suramin (Williams et al. (1984) J. Biol. Chem. 259:287-5294; Betsholtz et al. (1984) Cell 39:447-457), neomycin (Vassbotn et al. (1992) J. Biol. Chem. 267:15635-15641) and peptides derived from the PDGF amino acid sequence (Engström et al. (1992) J. Biol. Chem. 267:16581-16587) have been reported, however, they are either too toxic or lack sufficient specificity or potency to be good drug candidates. Other types of antagonists of possible clinical utility are molecules that selectively inhibit the PDGF receptor tyrosine kinase (Buchdunger et al. (1995) Proc. Natl. Acad. Sci. U.S.A. 92:2558-2562; Kovalenko et al. (1994) Cancer Res. 54:6106-6114).

SUMMARY OF THE INVENTION

The present invention includes methods of identifying and producing nucleic acid ligands to platelet-derived growth factor (PDGF) and homologous proteins and the nucleic acid ligands so identified and produced. For the purposes of this application, PDGF refers to PDGF AA, AB, and BB isoforms and homologous proteins. Specifically included in the definition are human PDGF AA, AB, and BB isoforms.

Described herein are high affinity ssDNA and RNA ligands to platelet derived growth factor (PDGF). The method utilized herein for identifying such nucleic acid ligands is called SELEX, an acronym for Systematic Evolution of Ligands by Exponential enrichment. Included herein are the evolved ligands that are shown in Tables 2-3, 6-7, and 9 and FIGS. 1-2, 8A, 8B and 9A. Further included in this invention is a method for preparing a Complex comprised of a PDGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of PDGF by the method of (a) contacting the Candidate Mixture of Nucleic Acids with PDGF, (b) partitioning between members of said Candidate Mixture on the basis of affinity to PDGF, and c) amplifying the selected molecules to yield a mixture of Nucleic Acids enriched for Nucleic Acid sequences with a relatively higher affinity for binding to PDGF, and covalently linking said identified PDGF Nucleic Acid Ligand with a Non-Immunogenic, High Molecular Weight Compound or a Lipophilic Compound. The invention further comprises a Complex comprised of a PDGF Nucleic Acid Ligand and a Non-Immunogenic, High Molecular Weight Compound or a Lipophilic Compound.

The invention further includes a Lipid Construct comprising a PDGF Nucleic Acid Ligand or a Complex. The present invention further relates to a method for preparing a Lipid Construct comprising a Complex wherein the Complex is comprised of a PDGF Nucleic Acid Ligand and a Lipophilic Compound.

In another embodiment, this invention provides a method for improving the pharmacokinetic properties of a PDGF Nucleic Acid Ligand by covalently linking the PDGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a PDGF Nucleic Acid Ligand by further associating the Complex with a Lipid Construct.

It is an object of the present invention to provide Complexes comprising one or more PDGF Nucleic Acid Ligands in association with one or more Non-Immunogenic, High Molecular Weight Compounds or Lipophilic Compounds and methods for producing the same. It is a further object of the present invention to provide Lipid Constructs comprising a Complex. It is a further object of the invention to provide one or more PDGF Nucleic Acid Ligands in association with one or more Non-Immunogenic, High Molecular Weight Compounds or Lipophilic Compounds with improved Pharmacokinetic Properties.

In embodiments of the invention directed to Complexes comprised of a PDGF Nucleic Acid Ligand and a Non-Immunogenic, High Molecular Weight Compound, it is preferred that the Non-Immunogenic, High Molecular Weight Compound is Polyalkylene Glycol, more preferably, polyethylene glycol (PEG). More preferably, the PEG has a molecular weight of about 10-80K. Most preferably, the PEG has a molecular weight of about 20-45K. In embodiments of the invention directed to Complexes comprised of a PDGF Nucleic Acid Ligand and a Lipophilic Compound, it is preferred that the Lipophilic Compound is a glycerolipid. In the preferred embodiments of the invention, the Lipid Construct is preferably a Lipid Bilayer Vesicle and most preferably a Liposome. In the preferred embodiment, the PDGF Nucleic Acid Ligand is identified according to the SELEX method.

In embodiments of the invention directed to Complexes comprising a Non-Immunogenic, High Molecular Weight Compound or Lipophilic Compound covalently linked to a PDGF Nucleic Acid Ligand or Ligands, the PDGF Nucleic Acid Ligand or Ligands can serve in a targeting capacity.

Additionally, the PDGF Nucleic Acid Ligand can be associated through Covalent or Non-Covalent Interactions with a Lipid Construct without being part of a Complex.

Furthermore, in embodiments of the invention directed to Lipid Constructs comprising a PDGF Nucleic Acid Ligand or a Non-Immunogenic, High Molecular Weight or Lipophilic Compound/PDGF Nucleic Acid Ligand Complex where the Lipid Construct is of a type that has a membrane defining an interior compartment such as a Lipid Bilayer Vesicle, the PDGF Nucleic Acid Ligand or Complex in association with the Lipid Construct may be associated with the membrane of the Lipid Construct or encapsulated within the compartment. In embodiments where the PDGF Nucleic Acid Ligand is in association with the membrane, the PDGF Nucleic Acid Ligand can associate with the interior-facing or exterior-facing part of the membrane, such that the PDGF Nucleic Acid Ligand is projecting into or out of the vesicle. In certain embodiments, a PDGF Nucleic Acid Ligand Complex can be passively loaded onto the outside of a preformed Lipid Construct. In embodiments where the Nucleic Acid Ligand is projecting out of the Lipid Construct, the PDGF Nucleic Acid Ligand can serve in a targeting capacity.

In embodiments where the PDGF Nucleic Acid Ligand of the Lipid Construct serves in a targeting capacity, the Lipid Construct can have associated with it additional therapeutic or diagnostic agents. In one embodiment, the therapeutic or diagnostic agent is associated with the exterior of the Lipid Construct. In other embodiments, the therapeutic or diagnostic agent is encapsulated in the Lipid Construct or associated with the interior of the Lipid Construct. In yet a further embodiment, the therapeutic or diagnostic agent is associated with the Complex. In one embodiment, the therapeutic agent is a drug. In an alternative embodiment, the therapeutic or diagnostic agent is one or more additional Nucleic Acid Ligands.

It is a further object of the present invention to provide a method for inhibiting PDGF-mediated diseases. PDGF-mediated diseases include, but are not limited to, cancer, angiogenesis, restenosis, and fibrosis. Thus, it is a further object of the present invention to provide a method for inhibiting angiogenesis by the administration of a PDGF Nucleic Acid Ligand or a Complex comprising a PDGF Nucleic Acid Ligand and Non-Immunogenic, High Molecular Weight Compound or Lipophilic Compound or a Lipid Construct comprising the Complex of the present invention. It is yet a further object of the present invention to provide a method for inhibiting the growth of tumors by the administration of a PDGF Nucleic Acid Ligand or Complex comprising a PDGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting fibrosis by the administration of a PDGF Nucleic Acid Ligand or Complex comprising a PDGF Nucleic Acid Ligand and Non-Immunogenic, High Molecular Weight Compound or Lipophilic Compound or a Lipid Construct comprising a Complex of the present invention. It is yet a further object of the present invention to provide a method for inhibiting restenosis by the administration of a PDGF Nucleic Acid Ligand or Complex comprising a PDGF Nucleic Acid Ligand and Non-Immunogenic, High Molecular Weight Compound or Lipophilic Compound or a Lipid Construct comprising a Complex of the present invention It is a further object of the invention to provide a method for targeting a therapeutic or diagnostic agent to a biological target that is expressing PDGF by associating the agent with a Complex comprised of a PDGF Nucleic Acid Ligand and a Lipophilic Compound or Non-Immunogenic, High Molecular Weight Compound, wherein the Complex is further associated with a Lipid Construct and the PDGF Nucleic Acid Ligand is further associated with the exterior of the Lipid Construct.

These and other objects, as well as the nature, scope and utilization of this invention, will become readily apparent to those skilled in the art from the following description and the appended claims.

BRIEF DESCRIPTION OF THE FIGURES

FIG. 2 shows the minimal ligands 20t, 36t and 41t folded according to the consensus secondary structure motif [3'T] represents a 3'-3' linked thymidine nucleotide added to reduce 3'-exonuclease degradation.

In FIGS. 8A-8C, the underlined symbols indicate 2'-O-methyl-2'-deoxynucleotides; italicized symbols indicate 2'-fluoro-2'-deoxynucleotides; normal font indicates 2'-deoxyribonucleotides; [3'T] indicates inverted orientation (3'3') thymidine nucleotide (Glen Research, Sterling, Va.); PEG in the loops of helices II and III of FIG. 8B indicates pentaethylene glycol spacer phosphoramidite (Glen Research, Sterling, Va.) (See FIG. 9 for molecular description). FIG. 8C shows the predicted secondary structure of a scrambled Nucleic Acid Ligand sequence that was used as a control in Examples 8 and 9. The scrambled region is boxed to accent the overall similarity of the scrambled Nucleic Acid ligand to the Nucleic Acid Ligand shown in FIG. 8B.

DETAILED DESCRIPTION OF THE INVENTION

Definitions

Figure 1:
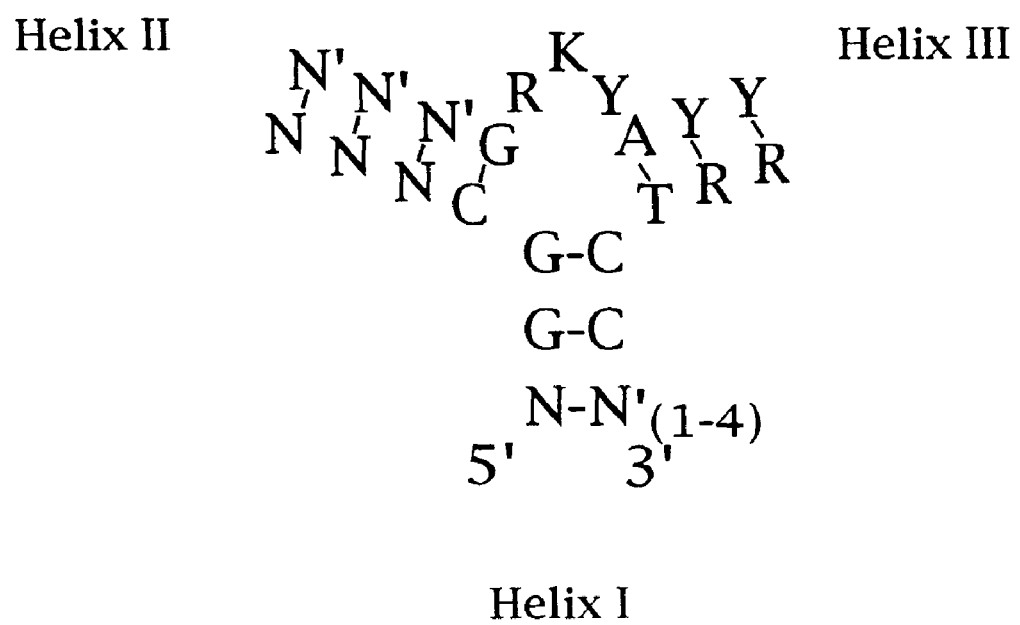
FIG. 1 shows the consensus secondary structure for the sequence set shown in Table 3. R=A or G, Y=C or T, K=G or T, N and N' indicate any base pair.

"Covalent Bond" is the chemical bond formed by the sharing of electrons.

"Non-Covalent Interactions" are means by which molecular entities are held together by interactions other than Covalent Bonds including ionic interactions and hydrogen bonds.

"Lipophilic Compounds" are compounds which have the propensity to associate with or partition into lipid and/or other materials or phases with low dielectric constants, including structures that are comprised substantially of lipophilic components. Lipophilic Compounds include lipids as well as non-lipid containing compounds that have the propensity to associate with lipid (and/or other materials or phases with low dielectric constants). Cholesterol, phospholipids, and glycerolipids, such as dialkylglycerol, and diacylglycerol, and glycerol amide lipids are further examples of Lipophilic Compounds.

"Complex" as used herein describes the molecular entity formed by the covalent linking of a PDGF Nucleic Acid Ligand to a Non-Immunogenic, High Molecular Weight Compound or Lipophilic Compound. In certain embodiments of the present invention, the Complex is depicted as A-B-Y, wherein A is a Lipophilic Compound or Non-Immunogenic, High Molecular Weight Compound as described herein; B is optional, and comprises a Spacer which may comprise one or more linkers Z; and Y is a PDGF Nucleic Acid Ligand.

"Lipid Constructs," for purposes of this invention, are structures containing lipids, phospholipids, or derivatives thereof comprising a variety of different structural arrangements which lipids are known to adopt in aqueous suspension. These structures include, but are not limited to, Lipid Bilayer Vesicles, micelles, Liposomes, emulsions, lipid ribbons or sheets, and may be complexed with a variety of drugs and components which are known to be pharmaceutically acceptable. In the preferred embodiment, the Lipid Construct is a Liposome. The preferred Liposome is unilamellar and has a relative size less than 200 nm. Common additional components in Lipid Constructs include cholesterol and alphatocopherol, among others. The Lipid Constructs may be used alone or in any combination which one skilled in the art would appreciate to provide the characteristics desired for a particular application. In addition, the technical aspects of Lipid Constructs and Liposome formation are well known in the art and any of the methods commonly practiced in the field may be used for the present invention.

"Nucleic Acid Ligand" as used herein is a non-naturally occurring Nucleic Acid having a desirable action on a Target. The Target of the present invention is PDGF, hence the term PDGF Nucleic Acid Ligand. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for PDGF, wherein the Nucleic Acid Ligand is not a Nucleic Acid having the known physiological function of being bound by PDGF.

In preferred embodiments of the invention, the PDGF Nucleic Acid Ligand of the Complexes and Lipid Constructs of the invention are identified by the SELEX methodology. PDGF Nucleic Acid Ligands are identified from a Candidate Mixture of Nucleic Acids, said Nucleic Acid being a ligand of PDGF, by the method comprising a) contacting the Candidate Mixture with PDGF, wherein Nucleic Acids having an increased affinity to PDGF relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids (see U.S. patent application Ser. No. 08/479,725, filed Jun. 7, 1995, entitled "High Affinity PDGF Nucleic Acid Ligands," now U.S. Pat. No. 5,674,685, U.S. patent application Ser. No. 08/479,783, filed Jun. 7, 1995, entitled "High Affinity PDGF Nucleic Acid Ligands," now U.S. Pat. No. 5,668,264, and U.S. patent application Ser. No. 08/618,693, filed Mar. 20, 1996, entitled "High Affinity PDGF Nucleic Acid Ligands," now U.S. Pat. No. 5,723,594, which are hereby incorporated by reference herein).

In certain embodiments, portions of the PDGF Nucleic Acid Ligand (Y) may not be necessary to maintain binding and certain portions of the contiguous PDGF Nucleic Acid Ligand can be replaced with a Spacer or Linker. In these embodiments, for example, Y can be represented as Y-B'-Y'-B"-Y''', wherein Y, Y' and Y" are parts of a PDGF Nucleic Acid Ligand or segments of different PDGF Nucleic Acid Ligands and B' and/or B" are Spacers or Linker molecules that replace certain nucleic acid features of the original PDGF Nucleic Acid Ligand. When B' and B" are present and Y, Y', and Y" are parts of one PDGF Nucleic Acid Ligand, a tertiary structure is formed that binds to PDGF. When B' and B" are not present, Y, Y', and Y" represent one contiguous PDGF Nucleic Acid Ligand. PDGF Nucleic Acid Ligands modified in such a manner are included in this definition.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications such as internucleoside phosphorothioate linkages, methylations, unusual base-pairing combinations such as the isobases isocytidine and isoguanidine and the like. Modifications can also include 3' and 5' modifications such as capping.

"Non-Immunogenic, High Molecular Weight Compound" is a compound between approximately 1000 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. Examples of Non-Immunogenic, High Molecular Weight Compounds include Polyalkylene Glycol and polyethylene glycol. In one preferred embodiment of the invention, the Non-Immunogenic, High Molecular Weight Compound covalently linked to the PDGF Nucleic Acid Ligand is a polyalkylene glycol and has the structure $R(O(CH_2)_x)_nO\text{—}$, where R is independently selected from the group consisting of H and $CH_3$, x=2-5, and n~MW of the Polyalkylene Glycol/(16+14x). In the preferred embodiment of the present invention, the molecular weight is about between 10-80 kDa. In the most preferred embodiment, the molecular weight of the polyalkylene glycol is about between 20-45 kDa. In the most preferred embodiment, x=2 and $n=9\times10^2$. There can be one or more Polyalkylene Glycols attached to the same PDGF Nucleic Acid Ligand, with the sum of the molecular weights preferably being between 10-80 kDa, more preferably 20-45 kDa.

In certain embodiments, the Non-Immunogenic, High Molecular Weight Compound can also be a Nucleic Acid Ligand.

"Lipid Bilayer Vesicles" are closed, fluid-filled microscopic spheres which are formed principally from individual molecules having polar (hydrophilic) and non-polar (lipophilic) portions. The hydrophilic portions may comprise phosphate, glycerylphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable components (including anti-oxidants like alpha-tocopherol) may also be included to improve vesicle stability or confer other desirable characteristics.

"Liposomes" are a subset of Lipid Bilayer Vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into unilamellar vesicles (UV), with the application of a shearing force.

"Cationic Liposome" is a Liposome that contains lipid components that have an overall positive charge at physiological pH.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. The SELEX methodology is described in the SELEX patent applications.

"Target" means any compound or molecule of interest for which a ligand is desired. A Target can be a protein (such as PDGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. The principal Target of the subject invention is PDGF.

"Improved Pharmacokinetic Properties" means that the PDGF Nucleic Acid Ligand covalently linked to a Non-Immunogenic, High Molecular Weight Compound or Lipophilic Compound or in association with a Lipid Construct shows a longer circulation half-life in vivo relative to the same PDGF Nucleic Acid Ligand not in association with a Non-Immunogenic, High Molecular Weight Compound or Lipophilic Compound or in association with a Lipid Construct.

Figure 9A:
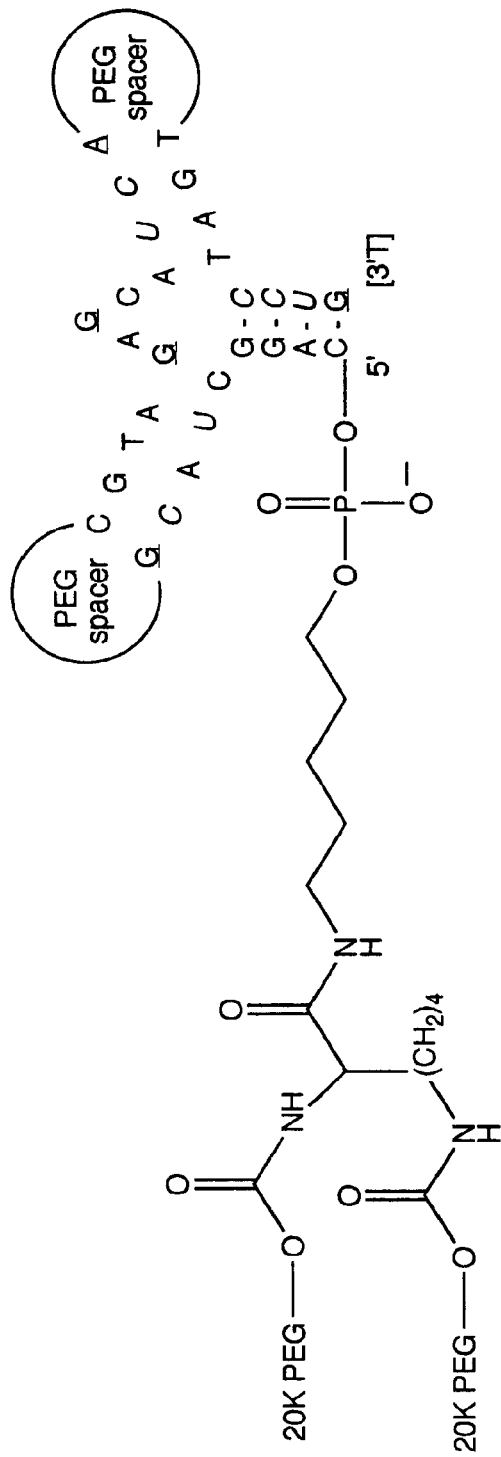
FIGS. 9A-9E show the molecular descriptions NX31975 40K PEG (FIG. 9A), NX31976 40K (FIG. 9B), hexaethylene glycol phosphoramidite (FIG. 9C), pentyl amino linker (FIG. 9D), and 40K PEG NHS ester (FIG. 9E). The 5' phosphate group shown in the PEG Spacer of FIGS. 9A and 9B are from the hexaethylene glycol phosphoramidite.
Figure 9A:
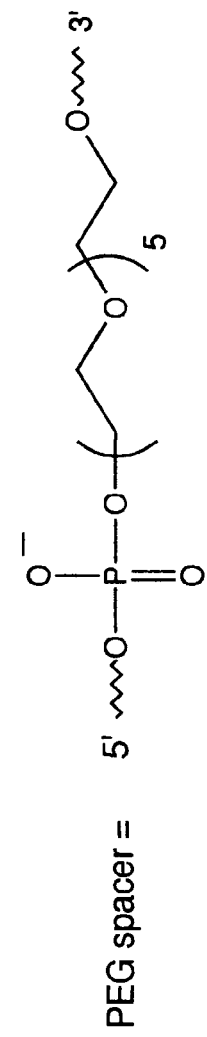
Figure 9B:
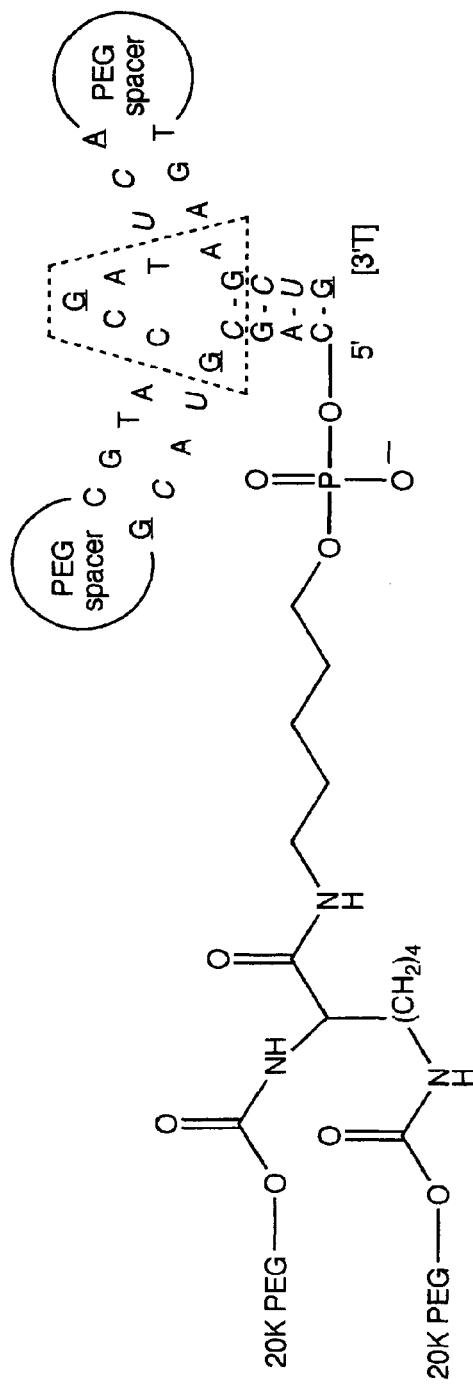
Figure 9B:
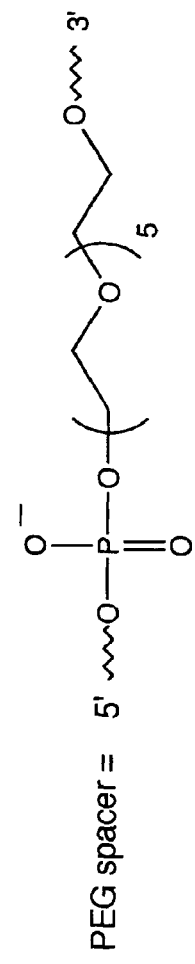
Figure 9C:
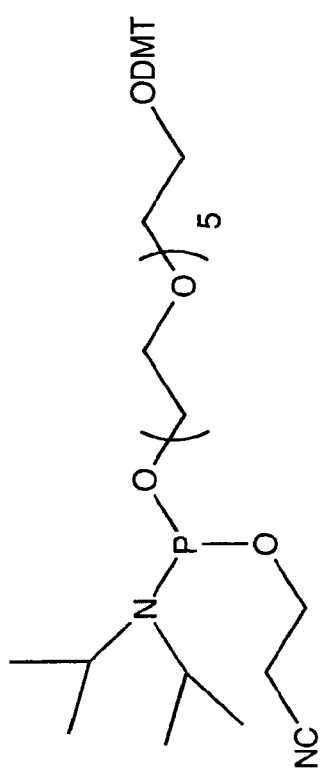

"Linker" is a molecular entity that connects two or more molecular entities through Covalent Bond or Non-Covalent Interactions, and can allow spatial separation of the molecular entities in a manner that preserves the functional properties of one or more of the molecular entities. A linker can also be known as a Spacer. Examples of Linkers, include but are not limited to, the structures shown in FIGS. 9C-9E and the PEG spacer shown in FIG. 9A.

In the preferred embodiment, the linker B' and B" are pentaethylene glycols.

"Therapeutic" as used herein, includes treatment and/or prophylaxis. When used, Therapeutic refers to humans and other animals.

This invention includes ssDNA and RNA ligands to PDGF. This invention further includes the specific RNA ligands to PDGF shown in Tables 2-3, 6-7, and 9 and FIGS. 1-2, 8A and 8B (SEQ ID NOS: 4-35, 39-87, 97-149). More specifically, this invention includes nucleic acid sequences that are substantially homologous to and that have substantially the same ability to bind PDGF as the specific nucleic acid ligands shown in Tables 2-3, 6-7, and 9 and FIGS. 1-2, 8A and 8B (SEQ ID NOS: 4-35, 39-87, 97-149). By substantially homologous it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. Substantially the same ability to bind PDGF means that the affinity is within one or two orders of magnitude of the affinity of the ligands described herein. It is well within the skill of those of ordinary skill in the art to determine whether a given sequence—substantially homologous to those specifically described herein—has the same ability to bind PDGF.

A review of the sequence homologies of the nucleic acid ligands of PDGF shown in Tables 2-3, 6-7, and 9 and FIGS. 1-2, 8A and 8B (SEQ ID NOS: 4-35, 39-87, 97-149) shows that sequences with little or no primary homology may have substantially the same ability to bind PDGF. For these reasons, this invention also includes Nucleic Acid Ligands that have substantially the same postulated structure or structural motifs and ability to bind PDGF as the nucleic acid ligands shown in Tables 2-3, 6-7, and 9 and FIGS. 1-2, 8A and 8B (SEQ ID NOS: 4-35, 39-87, 97-149). Substantially the same structure or structural motifs can be postulated by sequence alignment using the Zukerfold program (see Zuker (1989) Science 244:48-52). As would be known in the art, other computer programs can be used for predicting secondary structure and structural motifs. Substantially the same structure or structural motif of Nucleic Acid Ligands in solution or as a bound structure can also be postulated using NMR or other techniques as would be known in the art.

Further included in this invention is a method for preparing a Complex comprised of a PDGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of PDGF by the method of (a) contacting the Candidate Mixture of Nucleic Acids with PDGF, (b) partitioning between members of said Candidate Mixture on the basis of affinity to PDGF, and c) amplifying the selected molecules to yield a mixture of Nucleic Acids enriched for Nucleic Acid sequences with a relatively higher affinity for binding to PDGF, and covalently linking said identified PDGF Nucleic Acid Ligand with a Non-Immunogenic, High Molecular Weight Compound or a Lipophilic Compound.

It is a further object of the present invention to provide Complexes comprising one or more PDGF Nucleic Acid Ligands covalently linked to a Non-Immunogenic, High Molecular Weight Compound or Lipophilic Compound. Such Complexes have one or more of the following advantages over a PDGF Nucleic Acid Ligand not in association with a Non-Immunogenic, High Molecular Weight Compound or Lipophilic Compound: 1) improved Pharmacokinetic Properties, and 2) improved capacity for intracellular delivery, or 3) improved capacity for targeting. Complexes further associated with a Lipid Construct have the same advantages.

The Complexes or the Lipid Constructs comprising the PDGF Nucleic Acid Ligand or Complexes may benefit from one, two, or three of these advantages. For example, a Lipid Construct of the present invention may be comprised of a) a Liposome, b) a drug that is encapsulated within the interior of the Liposome, and c) a Complex comprised of a PDGF Nucleic Acid Ligand and Lipophilic Compound, wherein the PDGF Nucleic Acid Ligand component of the Complex is associated with and projecting from the exterior of the Lipid Construct. In such a case, the Lipid Construct comprising a Complex will 1) have Improved Pharmacokinetic Properties, 2) have enhanced capacity for intracellular delivery of the encapsulated drug, and 3) be specifically targeted to the preselected location in vivo that is expressing PDGF by the exteriorly associated PDGF Nucleic Acid Ligand.

In another embodiment, this invention provides a method for improving the pharmacokinetic properties of a PDGF Nucleic Acid Ligand by covalently linking the PDGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a PDGF Nucleic Acid Ligand by further associating the Complex with a Lipid Construct.

In another embodiment, the Complex of the present invention is comprised of a PDGF Nucleic Acid Ligand covalently attached to a Lipophilic Compound, such as a glycerolipid, or a Non-Immunogenic, High Molecular Weight Compound, such as Polyalkylene Glycol or polyethylene glycol (PEG). In these cases, the pharmacokinetic properties of the Complex will be enhanced relative to the PDGF Nucleic Acid Ligand alone. In another embodiment, the pharmacokinetic properties of the PDGF Nucleic Acid Ligand is enhanced relative to the PDGF Nucleic Acid Ligand alone when the PDGF Nucleic Acid Ligand is covalently attached to a Non-Immunogenic, High Molecular Weight Compound or Lipophilic Compound and is further associated with a Lipid Construct or the PDGF Nucleic Acid Ligand is encapsulated within a Lipid Construct.

In embodiments where there are multiple PDGF Nucleic Acid Ligands, there is an increase in avidity due to multiple binding interactions with PDGF. Furthermore, in embodiments where the Complex is comprised of multiple PDGF Nucleic Acid Ligands, the pharmacokinetic properties of the Complex will be improved relative to one PDGF Nucleic Acid Ligand alone. In embodiments where a Lipid Construct comprises multiple Nucleic Acid Ligands or Complexes, the Pharmacokinetic Properties of the PDGF Nucleic Acid Ligand may be improved relative to Lipid Constructs in which there is only one Nucleic Acid Ligand or Complex.

In certain embodiments of the invention, the Complex of the present invention is comprised of a PDGF Nucleic Acid Ligand attached to one (dimeric) or more (multimeric) other Nucleic Acid Ligands. The Nucleic Acid Ligand can be to PDGF or a different Target. In embodiments where there are multiple PDGF Nucleic Acid Ligands, there is an increase in avidity due to multiple binding interactions with PDGF. Furthermore, in embodiments of the invention where the Complex is comprised of a PDGF Nucleic Acid Ligand attached to one or more other PDGF Nucleic Acid Ligands, the pharmacokinetic properties of the Complex will be improved relative to one PDGF Nucleic Acid Ligand alone.

The Non-Immunogenic, High Molecular Weight compound or Lipophilic Compound may be covalently bound to a variety of positions on the PDGF Nucleic Acid Ligand, such as to an exocyclic amino group on the base, the 5-position of a pyrimidine nucleotide, the 8-position of a purine nucleotide, the hydroxyl group of the phosphate, or a hydroxyl group or other group at the 5 or 3' terminus of the PDGF Nucleic Acid Ligand. In embodiments where the Non-Immunogenic, High Molecular Weight Compound is polyalkylene glycol or polyethylene glycol, preferably it is bonded to the 5' or 3' hydroxyl of the phosphate group thereof. In the most preferred embodiment, the Non-Immunogenic, High Molecular Weight Compound is bonded to the 5' hydroxyl of the phosphate group of the Nucleic Acid Ligand. Attachment of the Non-Immunogenic, High Molecular Weight Compound or Lipophilic Compound to the PDGF Nucleic Acid Ligand can be done directly or with the utilization of Linkers or Spacers. In embodiments where the Lipid Construct comprises a Complex, or where the PDGF Nucleic Acid Ligands are encapsulated within the Liposome, a Non-Covalent Interaction between the PDGF Nucleic Acid Ligand or the Complex and the Lipid Construct is preferred.

One problem encountered in the therapeutic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the PDGF Nucleic Acid Ligand can be made to increase the in vivo stability of the PDGF Nucleic Acid Ligand or to enhance or to mediate the delivery of the PDGF Nucleic Acid Ligand. Modifications of the PDGF Nucleic Acid Ligands contemplated in this invention include, but are not limited to, those which provide other chemical groups that incorporate additional charge, polarizability, hydrophobicity, hydrogen bonding, electrostatic interaction, and fluxionality to the PDGF Nucleic Acid Ligand bases or to the PDGF Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield PDGF Nucleic Acid Ligands with both specificity for PDGF and improved in vivo stability. Post-SELEX modifications made to 2'-OH Nucleic Acid Ligands can result in improved in vivo stability without adversely affecting the binding capacity of the Nucleic Acid Ligands. The preferred modifications of the PDGF Nucleic Acid Ligands of the subject invention are 5' and 3' phosphorothioate capping and 3'3' inverted phosphodiester linkage at the 3' end. In the most preferred embodiment, the preferred modification of the PDGF Nucleic Acid Ligand is 3'3' inverted phosphodiester linkage at the 3' end. Additional 2' fluoro (2'-F), 2' amino (2'—$NH_2$) and 2' OMethyl (2'-OMe) modification of all or some of the nucleotides is preferred. In the most preferred embodiment, the preferred modification is 2'-OMe and 2'-F modification of some of the nucleotides. Additionally, the PDGF Nucleic Acid Ligand can be post-SELEX modified to substitute Linkers or Spacers such as hexaethylene glycol Spacers for certain portions.

In another aspect of the present invention, the covalent linking of the PDGF Nucleic Acid Ligand with a Non-Immunogenic, High Molecular Weight Compound or Lipophilic Compound results in Improved Pharmacokinetic Properties (i.e., slower clearance rate) relative to the PDGF Nucleic Acid Ligand not in association with a Non-Immunogenic, High Molecular Weight Compound or Lipophilic Compound.

In another aspect of the present invention, the Complex comprising a PDGF Nucleic Acid Ligand and Non-Immunogenic, High Molecular Weight Compound or Lipophilic Compound can be further associated with a Lipid Construct. This association may result in Improved Pharmacokinetic Properties relative to the PDGF Nucleic Acid Ligand or Complex not in association with a Lipid Construct. The PDGF Nucleic Acid Ligand or Complex can be associated with the Lipid Construct through covalent or Non-Covalent Interactions. In another aspect, the PDGF Nucleic Acid Ligand can be associated with the Lipid Construct through Covalent or Non-Covalent Interactions. In a preferred embodiment, the association is through Non-Covalent Interactions. In a preferred embodiment, the Lipid Construct is a Lipid Bilayer Vesicle. In the most preferred embodiment, the Lipid Construct is a Liposome.

Liposomes for use in the present invention can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. Multilamellar Liposomes can be formed by conventional techniques, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques.

In certain embodiments of this invention, the Lipid Construct comprises a targeting PDGF Nucleic Acid Ligand(s) associated with the surface of the Lipid Construct and an encapsulated therapeutic or diagnostic agent. Preferably the Lipid Construct is a Liposome. Preformed Liposomes can be modified to associate with the PDGF Nucleic Acid Ligands. For example, a Cationic Liposome associates through electrostatic interactions with the PDGF Nucleic Acid Ligand. A PDGF Nucleic Acid Ligand covalently linked to a Lipophilic Compound, such as a glycerolipid, can be added to preformed Liposomes whereby the glycerolipid, phospholipid, or glycerol amide lipid becomes associated with the liposomal membrane. Alternatively, the PDGF Nucleic Acid Ligand can be associated with the Liposome during the formulation of the Liposome.

It is well known in the art that Liposomes are advantageous for encapsulating or incorporating a wide variety of therapeutic and diagnostic agents. Any variety of compounds can be enclosed in the internal aqueous compartment of the Liposomes. Illustrative therapeutic agents include antibiotics, antiviral nucleosides, antifungal nucleosides, metabolic regulators, immune modulators, chemotherapeutic drugs, toxin antidotes, DNA, RNA, antisense oligonucleotides, etc. By the same token, the Lipid Bilayer Vesicles may be loaded with a diagnostic radionuclide (e.g., Indium 111, Iodine 131, Yttrium 90, Phosphorous 32, or gadolinium) and fluorescent materials or other materials that are detectable in in vitro and in vivo applications. It is to be understood that the therapeutic or diagnostic agent can be encapsulated by the Liposome walls in the aqueous interior. Alternatively, the carried agent can be a part of, that is, dispersed or dissolved in the vesicle wall-forming materials.

During Liposome formation, water soluble carrier agents may be encapsulated in the aqueous interior by including them in the hydrating solution, and lipophilic molecules incorporated into the lipid bilayer by inclusion in the lipid formulation. In the case of certain molecules (e.g., cationic or anionic lipophilic drugs), loading of the drug into preformed Liposomes may be accomplished, for example, by the methods described in U.S. Pat. No. 4,946,683, the disclosure of which is incorporated herein by reference. Following drug encapsulation, the Liposomes are processed to remove unencapsulated drug through processes such as gel chromatography or ultrafiltration. The Liposomes are then typically sterile filtered to remove any microorganisms which may be present in the suspension. Microorganisms may also be removed through aseptic processing.

If one wishes to encapsulate large hydrophilic molecules with Liposomes, larger unilamellar vesicles can be formed by methods such as the reverse-phase evaporation (REV) or solvent infusion methods. Other standard methods for the formation of Liposomes are known in the art, for example, methods for the commercial production of Liposomes include the homogenization procedure described in U.S. Pat. No. 4,753,788 and the thin-film evaporation method described in U.S. Pat. No. 4,935,171, which are incorporated herein by reference.

It is to be understood that the therapeutic or diagnostic agent can also be associated with the surface of the Lipid Bilayer Vesicle. For example, a drug can be attached to a phospholipid or glyceride (a prodrug). The phospholipid or glyceride portion of the prodrug can be incorporated into the lipid bilayer of the Liposome by inclusion in the lipid formulation or loading into preformed Liposomes (see U.S. Pat. Nos. 5,194,654 and 5,223,263, which are incorporated by reference herein).

It is readily apparent to one skilled in the art that the particular Liposome preparation method will depend on the intended use and the type of lipids used to form the bilayer membrane.

Lee and Low (1994, JBC 269:3198-3204) and DeFrees et al. (1996, JACS 118:6101-6104) first showed that co-formulation of ligand-PEG-lipid with lipid components gave liposomes with both inward and outward facing orientations of the PEG-ligand. Passive anchoring was outlined by Zalipsky et al. (1997, Bioconj. Chem. 8:111-118) as a method for anchoring oligopeptide and oligosaccharide ligands exclusively to the external surface of liposomes. The central concept presented in their work is that oligo-PEG-lipid conjugates can be prepared and then formulated into pre-formed liposomes via spontaneous incorporation ("anchoring") of the lipid tail into the existing lipid bilayer. The lipid group undergoes this insertion in order to reach a lower free energy state via the removal of its hydrophobic lipid anchor from aqueous solution and its subsequent positioning in the hydrophobic lipid bilayer. The key advantage to such a system is that the oligo-lipid is anchored exclusively to the exterior of the lipid bilayer. Thus, no oligo-lipids are wasted by being unavailable for interactions with their biological targets by being in an inward-facing orientation.

The efficiency of delivery of a PDGF Nucleic Acid Ligand to cells may be optimized by using lipid formulations and conditions known to enhance fusion of Liposomes with cellular membranes. For example, certain negatively charged lipids such as phosphatidylglycerol and phosphatidylserine promote fusion, especially in the presence of other fusogens (e.g., multivalent cations like $Ca^{2+}$, free fatty acids, viral fusion proteins, short chain PEG, lysolecithin, detergents and surfactants). Phosphatidylethanolamine may also be included in the Liposome formulation to increase membrane fusion and, concomitantly, enhance cellular delivery. In addition, free fatty acids and derivatives thereof, containing, for example, carboxylate moieties, may be used to prepare pH-sensitive Liposomes which are negatively charged at higher pH and neutral or protonated at lower pH. Such pH-sensitive Liposomes are known to possess a greater tendency to fuse.

In the preferred embodiment, the PDGF Nucleic Acid Ligands of the present invention are derived from the SELEX methodology. SELEX is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, now U.S. Pat. No. 5,475,096, and U.S. patent application Ser. No. 07/931,473, filed Aug. 17, 1992, entitled "Methods for Identifying Nucleic Acid Ligands," now U.S. Pat. No. 5,270,163 (see also WO 91/19813). These applications, each specifically incorporated herein by reference, are collectively called the SELEX patent applications.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5-50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned (see U.S. Pat. No. 5,580,737), describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by Exponential Enrichment: Solution SELEX," now abandoned (see U.S. Pat. No. 5,567,588), describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by Exponential Enrichment Chemi-SELEX," now U.S. U.S. Pat. No. 5,705,337, describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'—$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method Her encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled Nucleic Acid Ligand Complexes," now U.S. Pat. No. 6,011,021. The SELEX method further encompasses combining selected VEGF Nucleic Acid Ligands with lipophilic compounds, such as diacyl glycerol or dialkyl glycerol, as described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228. VEGF Nucleic Acid Ligands that are associated with a High Molecular Weight, Non-Immunogenic Compound, such as Polyethyleneglycol, or a Lipophilic Compound, such as Glycerolipid, phospholipid, or glycerol amide lipid, in a diagnostic or therapeutic complex are described in U.S. patent application Ser. No. 08/897,351, filed Jul. 21, 1997, entitled "Vascular Endothelial Growth Factor (VEGF) Nucleic Acid Ligand Complexes," now U.S. Pat. No. 6,051,698. Each of the above described patent applications which describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In commonly assigned U.S. patent application. Ser. No. 07/964,624, filed Oct. 21, 1992 ('624), now U.S. Pat. No. 5,496,938, methods are described for obtaining improved Nucleic Acid Ligands after SELEX has been performed. The '624 application, entitled Nucleic Acid Ligands to HIV-RT and HIV-1 Rev, is specifically incorporated herein by reference.

The SELEX process has been used to identify a group of high affinity RNA Ligands to PDGF from random ssDNA libraries and 2'-fluoro-2'-deoxypyrimidine RNA ligands from random ssDNA libraries (U.S. patent application Ser. No. 08/618,693, filed Mar. 20, 1996, entitled High-Affinity PDGF Nucleic Acid Ligands, now U.S. Pat. No. 5,723,594, which is a Continuation-in-Part Application of U.S. patent application Ser. No. 08/479,783, filed Jun. 7, 1995, entitled High-Affinity PDGF Nucleic Acid Ligands, now U.S. Pat. No. 5,668,264, and U.S. patent application Ser. No. 08/479,725, filed Jun. 7, 1995, entitled "High Affinity PDGF Nucleic Acid Ligands, now U.S. Pat. No. 5,674,685, both of which are incorporated herein by reference; see also Green et al. (1995) Chemistry and Biology 2:683-695).

In embodiments where the PDGF Nucleic Acid Ligand(s) can serve in a targeting capacity, the PDGF Nucleic Acid Ligands adopt a three dimensional structure that must be retained in order for the PDGF Nucleic Acid Ligand to be able to bind its target. In embodiments where the Lipid Construct comprises a Complex and the PDGF Nucleic Acid Ligand of the Complex is projecting from the surface of the Lipid Construct, the PDGF Nucleic Acid Ligand must be properly oriented with respect to the surface of the Lipid Construct so that its target binding capacity is not compromised. This can be accomplished by attaching the PDGF Nucleic Acid Ligand at a position that is distant from the binding portion of the PDGF Nucleic Acid Ligand. The three dimensional structure and proper orientation can also be preserved by use of a Linker or Spacer as described supra.

Any variety of therapeutic or diagnostic agents can be attached to the Complex for targeted delivery by the Complex. In addition, any variety of therapeutic or diagnostic agents can be attached encapsulated, or incorporated into the Lipid Construct as discussed supra for targeted delivery by the Lipid Construct.

In embodiments where the Complex is comprised of a Lipophilic Compound and a PDGF Nucleic Acid Ligand in association with a Liposome, for example, the PDGF Nucleic Acid Ligand could target tumor cells expressing PDGF (e.g., in Kaposi's sarcoma) for delivery of an antitumor drug (e.g., daunorubicin) or imaging agent (e.g., radiolabels). It should be noted that cells and tissues surrounding the tumor may also express PDGF, and targeted delivery of an antitumor drug to these cells would also be effective.

In an alternative embodiment, the therapeutic or diagnostic agent to be delivered to the Target cell could be another Nucleic Acid Ligand.

It is further contemplated by this invention that the agent to be delivered can be incorporated into the Complex in such a way as to be associated with the outside surface of the Liposome (e.g., a prodrug, receptor antagonist, or radioactive substance for treatment or imaging). As with the PDGF Nucleic Acid Ligand, the agent can be associated through covalent or Non-Covalent Interactions. The Liposome would provide targeted delivery of the agent extracellularly, with the Liposome serving as a Linker.

In another embodiment, a Non-Immunogenic, High Molecular Weight Compound (e.g., PEG) can be attached to the Liposome to provide Improved Pharmacokinetic Properties for the Complex. PDGF Nucleic Acid Ligands may be attached to the Liposome membrane or may be attached to a Non-Immunogenic, High Molecular Weight Compound which in turn is attached to the membrane. In this way, the Complex may be shielded from blood proteins and thus be made to circulate for extended periods of time while the PDGF Nucleic Acid Ligand is still sufficiently exposed to make contact with and bind to its Target.

In another embodiment of the present invention, more than one PDGF Nucleic Acid Ligand is attached to the surface of the same Liposome. This provides the possibility of bringing the same PDGF molecules in close proximity to each other and can be used to generate specific interactions between the PDGF molecules.

In an alternative embodiment of the present invention, PDGF Nucleic Acid Ligands and a Nucleic Acid Ligand to a different Target can be attached to the surface of the same Liposome. This provides the possibility of bringing PDGF in close proximity to a different Target and can be used to generate specific interactions between PDGF and the other Target. In addition to using the Liposome as a way of bringing Targets in close proximity, agents could be encapsulated in the Liposome to increase the intensity of the interaction.

The Lipid Construct comprising a Complex allows for the possibility of multiple binding interactions to PDGF. This, of course, depends on the number of PDGF Nucleic Acid Ligands per Complex, and the number of Complexes per Lipid Construct, and mobility of the PDGF Nucleic Acid Ligands and receptors in their respective membranes. Since the effective binding constant may increase as the product of the binding constant for each site, there is a substantial advantage to having multiple binding interactions. In other words, by having many PDGF Nucleic Acid Ligands attached to the Lipid Construct, and therefore creating multivalency, the effective affinity (i.e., the avidity) of the multimeric Complex for its Target may become as good as the product of the binding constant for each site.

In certain embodiments of the invention, the Complex of the present invention is comprised of a PDGF Nucleic Acid Ligand attached to a Lipophilic Compound. In this case, the pharmacokinetic properties of the Complex will be improved relative to the PDGF Nucleic Acid Ligand alone. As discussed supra, the Lipophilic Compound may be covalently bound to the PDGF Nucleic Acid Ligand at numerous positions on the PDGF Nucleic Acid Ligand.

In another embodiment of the invention, the Lipid Construct comprises a PDGF Nucleic Acid Ligand or Complex. In this embodiment, the glycerolipid can assist in the incorporation of the PDGF Nucleic Acid Ligand into the Liposome due to the propensity for a glycerolipid to associate with other Lipophilic Compounds. The glycerolipid in association with a PDGF Nucleic Acid Ligand can be incorporated into the lipid bilayer of the Liposome by inclusion in the formulation or by loading into preformed Liposomes. The glycerolipid can associate with the membrane of the Liposome in such a way so as the PDGF Nucleic Acid Ligand is projecting into or out of the Liposome. In embodiments where the PDGF Nucleic Acid Ligand is projecting out of the Complex, the PDGF Nucleic Acid Ligand can serve in a targeting capacity.

It is to be understood that additional compounds can be associated with the Lipid Construct to further improve the Pharmacokinetic Properties of the Lipid Construct. For example, a PEG may be attached to the exterior-facing part of the membrane of the Lipid Construct.

In other embodiments, the Complex of the present invention is comprised of a PDGF Nucleic Acid Ligand covalently linked to a Non-Immunogenic, High Molecular Weight Compound such as Polyalkylene Glycol or PEG. In this embodiment, the pharmacokinetic properties of the Complex are improved relative to the PDGF Nucleic Acid Ligand alone. The Polyalkylene Glycol or PEG may be covalently bound to a variety of positions on the PDGF Nucleic Acid Ligand. In embodiments where Polyalkylene Glycol or PEG are used, it is preferred that the PDGF Nucleic Acid Ligand is bonded through the 5 hydroxyl group via a phosphodiester linkage.

In certain embodiments, a plurality of Nucleic Acid Ligands can be associated with a single Non-Immunogenic, High Molecular Weight Compound, such as Polyalkylene Glycol or PEG, or a Lipophilic Compound, such as a glycerolipid. The Nucleic Acid Ligands can all be to PDGF or PDGF and a different Target. In embodiments where there are multiple PDGF Nucleic Acid Ligands, there is an increase in avidity due to multiple binding interactions with PDGF. In yet further embodiments, a plurality of Polyalkylene Glycol, PEG, glycerol lipid molecules can be attached to each other. In these embodiments, one or more PDGF Nucleic Acid Ligands or Nucleic Acid Ligands to PDGF and other Targets can be associated with each Polyalkylene Glycol, PEG, or glycerol lipid. This also results in an increase in avidity of each Nucleic Acid Ligand to its Target. In embodiments where multiple PDGF Nucleic Acid Ligands are attached to Polyalkylene Glycol, PEG, or glycerol lipid, there is the possibility of bringing PDGF molecules in close proximity to each other in order to generate specific interactions between PDGF. Where multiple Nucleic Acid Ligands specific for PDGF and different Targets are attached to Polyalkylene Glycol, PEG, or glycerol lipid, there is the possibility of bringing PDGF and another Target in close proximity to each other in order to generate specific interactions between the PDGF and the other Target. In addition, in embodiments where there are Nucleic Acid Ligands to PDGF or Nucleic Acid Ligands to PDGF and different Targets associated with Polyalkylene Glycol, PEG, or glycerol lipid, a drug can also be associated with Polyalkylene Glycol, PEG, or glycerol lipid. Thus the Complex would provide targeted delivery of the drug, with Polyalkylene Glycol, PEG, or glycerol lipid serving as a Linker.

PDGF Nucleic Acid Ligands selectively bind PDGF. Thus, a Complex comprising a PDGF Nucleic Acid Ligand and a Non-Immunogenic, High Molecular Weight Compound or Lipophilic Compound or a Lipid Construct comprising a PDGF Nucleic Acid Ligand or a Complex are useful as pharmaceuticals or diagnostic agents. The PDGF Nucleic Acid Ligand-containing Complexes and Lipid Constructs can be used to treat, inhibit, prevent or diagnose any disease state that involves inappropriate PDGF production, for example, cancer, angiogenesis, restenosis, and fibrosis. PDGF is produced and secreted in varying amounts by many tumor cells. Thus, the present invention, includes methods of treating, inhibiting, preventing, or diagnosing cancer by administration of a Complex comprising a PDGF Nucleic Acid Ligand and a Non-Immunogenic, High Molecular Weight Compound or Lipophilic Compound, a Lipid Construct comprising a Complex, or a PDGF Nucleic Acid Ligand in association with a Lipid Construct without being part of the Complex.

Angiogenesis rarely occurs in healthy adults, except during the menstrual cycle and wound healing. Angiogenesis is a central feature, however, of various disease states, including, but not limited to cancer, diabetic retinopathy, macular degeneration, psoriasis and rheumatoid arthritis. The present invention, therefore, includes methods of treating, inhibiting, preventing, or diagnosing angiogenesis by administration of a Complex comprising PDGF Nucleic Acid Ligand and a Non-Immunogenic, High Molecular Weight Compound or Lipophilic Compound, a Lipid Construct comprising PDGF Nucleic Acid Ligand or a Complex comprising a PDGF Nucleic Acid Ligand and a Non-Immunogenic, High Molecular Weight Compound or Lipophilic Compound.

PDGF is also produced in fibrosis in organs, such as lung, bone marrow and kidney. Fibrosis can also be associated with radiation treatments. The present invention, therefore, includes methods of treating, inhibiting, preventing or diagnosing lung, bone marrow, kidney and radiation treatment-associated fibrosis by administration of a Complex comprising PDGF Nucleic Acid Ligand and a Non-Immunogenic, High Molecular Weight Compound or Lipophilic Compound, a Lipid Construct comprising PDGF Nucleic Acid Ligand or a Complex comprising a PDGF Nucleic Acid Ligand and a Non-Immunogenic, High Molecular Weight Compound or Lipophilic Compound.

PDGF is a prominent growth factor involved in restenosis. Restenosis, the reocclusion of a diseased blood vessel after treatment to eliminate stenosis, is a common occurrence that develops following coronary interventions and some peripheral vessel interventions. Additionally, stents have been used in the treatment of or in conjunction with treatment of coronary and non-coronary vessels; however, restenosis is also associated with use of stents (called in-stent restenosis). In-stent restenosis occurs in about 15-30% of coronary interventions and frequently in some peripheral vessel interventions. For example, in-stent restenosis is a significant problem in small vessels, with frequencies ranging from 15% to 40% in stented femoral or popliteal arteries. Intermediate-sized vessels, such as renal arteries, have an in-stent restenosis rate of 10-20%.

The present invention, therefore, includes methods of treating, inhibiting, preventing or diagnosing restenosis by administration of a Complex comprising PDGF Nucleic Acid Ligand and a Non-Immunogenic, High Molecular Weight Compound or Lipophilic Compound, a Lipid Construct comprising PDGF Nucleic Acid Ligand or a Complex comprising a PDGF Nucleic Acid Ligand and a Non-Immunogenic, High Molecular Weight Compound or Lipophilic Compound. The present invention also includes methods of treating, inhibiting, preventing or diagnosing restenosis in coronary and non-coronary vessels. The present invention also includes methods of treating, inhibiting, preventing or diagnosing in-stent restenosis.

Additionally, cancer, angiogenesis, restenosis, and fibrosis involve the production of growth factors other than PDGF. Thus, it is contemplated by this invention that a Complex comprising PDGF Nucleic Acid Ligand and a Non-Immunogenic, High Molecular Weight Compound or Lipophilic Compound, a Lipid Construct comprising PDGF Nucleic Acid Ligand or a Complex comprising a PDGF Nucleic Acid Ligand and a Non-Immunogenic, High Molecular Weight Compound or Lipophilic Compound can be used in conjunction with Complexes comprising Nucleic Acid Ligands to other growth factors (such as bFGF, TGFβ, hKGF, etc.) and a Non-Immunogenic, High Molecular Weight Compound or Lipophilic Compound, a Lipid Construct comprising PDGF Nucleic Acid Ligand or a Complex comprising a PDGF Nucleic Acid Ligand and a Non-Immunogenic, High Molecular Weight Compound or Lipophilic Compound.

In one embodiment of the present invention, the Lipid Construct comprises a Complex comprised of a PDGF Nucleic Acid Ligand and a Lipophilic Compound with an additional diagnostic or therapeutic agent encapsulated in the Lipid Construct or associated with the interior of the Lipid Construct. In the preferred embodiment, the Lipid Construct is a Lipid Bilayer Vesicle, and more preferably a Liposome. The therapeutic use of Liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. In one embodiment of the present invention, the PDGF Nucleic Acid Ligand is associated with the outside surface of the liposome, and serves in a targeting capacity. Additional targeting components, such as antibodies or specific receptor ligands can be included on the liposome surface, as would be known to one of skill in the art. In addition, some efforts have been successful in targeting liposomes to tumors without the use of antibodies, see, for example, U.S. Pat. Nos. 5,019,369, 5,435,989, and 4,441,775, and it would be known to one of skill in the art to incorporate these alternative targeting methods.

Therapeutic or diagnostic compositions of a Complex comprising PDGF Nucleic Acid Ligand and a Non-Immunogenic, High Molecular Weight Compound or Lipophilic Compound, a Lipid Construct comprising a Complex comprised of a PDGF Nucleic Acid Ligand and a Non-Immunogenic, High Molecular Weight Compound or Lipophilic Compound, and a PDGF Nucleic Acid Ligand in association with a Lipid Construct without being part of a Complex may be administered parenterally by injection, although other effective administration forms, such as intraarticular injection, inhalant mists, orally active formulations, transdermal iotophoresis or suppositories, are also envisioned. They may also be applied locally by direct injection, can be released from devices, such as implanted stents or catheters, or delivered directly to the site by an infusion pump. One preferred carrier is physiological saline solution, but it is contemplated that other pharmaceutically acceptable carriers may also be used. In one embodiment, it is envisioned that the carrier and the PDGF Nucleic Acid Ligand Complex constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the PDGF Nucleic Acid Ligand. Such excipients are those substances usually and customarily employed to formulate dosages for parental administration in either unit dose or multi-dose form.

Once the therapeutic or diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to administration. The manner of administering formulations containing PDGF Nucleic Acid Ligand for systemic delivery may be via subcutaneous, intramuscular, intravenous, intranasal or vaginal or rectal suppository.

The advantages of the Complexes and Lipid Constructs of the invention include: i) improving the plasma pharmacokinetics of the Nucleic Acid Ligand; ii) Presenting Nucleic Acid Ligands in a multivalent array with the aim of increasing the avidity of interaction with their targets; iii) combining two or more presenting Nucleic Acid Ligands with different specificities in the same liposome particle; iv) enhancing the delivery of presenting Nucleic Acid Ligands to tumors by taking advantage of the intrinsic tumor targeting properties of liposomes; and v) using the high affinity and specificity of presenting Nucleic Acid Ligands, which is comparable to that of antibodies, to guide liposomal contents to specific targets. presenting Nucleic Acid Ligands are well suited for the kinds of preparations described here since, unlike most proteins, the denaturation of presenting Nucleic Acid Ligands by heat, various molecular denaturants and organic solvents is readily reversible.

The following examples are provided to explain and illustrate the present invention and are not to be taken as limiting of the invention. Example 1 describes the various materials and experimental procedures used in Examples 2-4 for the generation of ssDNA ligands to PDGF and tests associated therewith. Example 2 describes the ssDNA ligands to PDGF and the predicted secondary structure of selected nucleic acid ligands and a shared secondary structure motif. Example 3 describes the minimum sequence necessary for high affinity binding, the sites on the nucleic acid ligands and PDGF that are in contact, inhibition by DNA ligands of PDGF isoforms on cultured cells, and inhibition of mitogenic effects of PDGF in cells by DNA ligands. Example 4 describes substitutions of SELEX-derived ligands with modified nucleotides. Example 5 describes synthesis of PEG-modified PDGF Nucleic Acid Ligands. Example 6 describes stability of modified ligands in serum. Example 7 describes efficacy of a modified ligand (NX31975-40K PEG) in restenosis. Example 8 describes the various materials and method used in Example 9 for testing the inhibition of PDGF in glomerulonephritis. Example 9 describes inhibition of PDGF in glomerulonephritis. Example 10 describes the experimental procedures for evolving 2'-fluoro-2'-deoxypyrimidine RNA ligands to PDGF and the RNA sequences obtained.

EXAMPLE 1

Experimental Procedures

This example provides the general procedures followed and incorporated in Examples 2-4.

Materials

Recombinant human PDGF-AA (Mr=29,000), PDGF-AB (Mr=27,000) and PDGF-BB (Mr=25,000) were purchased from R&D Systems (Minneapolis, Minn.) in lyophilized form, free from carrier protein. All three isoforms were produced in *E. coli* from synthetic genes based on the sequences for the long form of the mature human PDGF A-chain (Betsholtz et al. (1986) Nature 320:695-699) and the naturally occurring mature form of human PDGF B-chain (Johnsson et al. (1984) EMBO J. 3:921-928). Randomized DNA libraries, PCR primers and DNA ligands and 5'-iodo-2'-deoxyuridine-substituted DNA ligands were synthesized by NeXstar Pharmaceuticals, Inc. (Boulder, Colo.) or by Operon Technologies (Alameda, Calif.) using the standard solid phase phosphoramidite method (Sinha et al. (1984) Nucleic Acids Res. 12:4539-4557).

Single stranded DNA (ssDNA) SELEX

Essential features of the SELEX procedure have been described in detail in the SELEX patent applications (see also Tuerk and Gold (1990) Science 249:505; Jellinek et al. (1994) Biochemistry 33:10450; Jellinek et al. (1993) Proc. Natl. Acad. Sci. USA 90:1227), which are incorporated by reference herein. The initial ssDNA library containing a contiguous randomized region of forty nucleotides, flanked by primer annealing regions (Table 1) (SEQ ID NOS: 1-3) of invariant sequence, was synthesized by the solid phase phosphoramidite method using equal molar mixture of the four phosphoramidites to generate the randomized positions. The ssDNA library was purified by electrophoresis on an 8% polyacrylamide/7 M urea gel. The band that corresponds to the full-length DNA was visualized under UV light, excised from the gel, eluted by the crush and soak method, ethanol precipitated and pelleted by centrifugation. The pellet was dried under vacuum and resuspended in phosphate buffered saline supplemented with 1 mM $MgCl_2$(PBSM=10.1 mM $Na_2HPO_4$, 1.8 mM $KH_2PO_4$, 137 mM NaCl and 2.7 mM KCl, 1 mM $MgCl_2$, pH 7.4) buffer. Prior to incubation with the protein, the ssDNA was heated at 90° C. for 2 minutes in PBSM and cooled on ice. The first selection was initiated by incubating approximately 500 pmol ($3\times10^{14}$ molecules) of $5'^{32}P$ end-labeled random ssDNA with PDGF-AB in binding buffer (PBSM containing 0.01% human serum albumin (HSA)). The mixture was incubated at 4° C. overnight, followed by a brief (15 min) incubation at 37° C. The DNA bound to PDGF-AB was separated from unbound DNA by electrophoresis on an 8% polyacrylamide gel (1:30 bis-acrylamide:acrylamide) at 4° C. and at 5 V/cm with 89 mM Tris-borate (pH 8.3) containing 2 mM EDTA as the running buffer. The band that corresponds to the PDGF-ssDNA complex, which runs with about half the electrophoretic mobility of the free ssDNA, was visualized by autoradiography, excised from the gel and eluted by the crush and soak method. In subsequent affinity selections, the ssDNA was incubated with PDGF-AB for 15 minutes at 37° C. in binding buffer and the PDGF-bound ssDNA was separated from the unbound DNA by nitrocellulose filtration, as previously described (Green et al. (1995) Chemistry and Biology 2:683-695). All affinity-selected ssDNA pools were amplified by PCR in which the DNA was subjected to 12-20 rounds of thermal cycling (30 s at 93° C., 10 s at 52° C., 60 s at 72° C.) in 10 mM Tris-Cl (pH 8.4) containing 50 mM KCl, 7.5 mM $MgCl_2$, 0.05 mg/ml bovine serum albumin, 1 mM deoxynucleoside triphosphates, 5 µM primers (Table 1) (SEQ ID NOS: 2, 3) and 0.1 units/µl Taq polymerase. The 5' PCR primer was 5' end-labeled with polynucleotide kinase and [α-$^{32}$P]ATP and the 3' PCR primer was biotinylated at the 5' end using biotin phosphoramidite (Glen Research, Sterling, Va.). Following PCR amplification, streptavidin (Pierce, Rockford, Ill.) was added to the unpurified PCR reaction mixture at a 10-fold molar excess over the biotinylated primer and incubated for 15 min at room temperature. The dsDNA was denatured by adding an equal volume of stop solution (90% formamide, 1% sodium dodecyl sulfate, 0.025% bromophenol blue and xylene cyanol) and incubating for 20 min at room temperature. The radiolabeled strand was separated from the streptavidin-bound biotinylated strand by electrophoresis on 12% polyacrylamide/7M urea gels. The faster migrating radiolabeled (non-biotinylated) ssDNA strand was cut out of the gel and recovered as described above. The amount of ssDNA was estimated from the absorbance at 260 nm using the extinction coefficient of 33 µg/ml/absorbance unit (Sambrook et al. (1989) *Molecular Cloning: A Laboratory Manual*, 2nd Ed. 3 vols., Cold Spring Harbor Laboratory Press, Cold Spring Harbor, N.Y.).

Cloning and Sequencing. The amplified affinity-enriched pool from SELEX round 12 was purified on a 12% polyacrylamide gel and cloned between HindIII and PstI sites in JM109 strain of *E. coli* (Sambrook et al. (1989) *Molecular Cloning: A Laboratory Manual*, 2nd Ed. 3 vols., Cold Spring Harbor Laboratory Press, Cold Spring Harbor). Individual clones were used to prepare plasmids by alkaline lysis. Plasmids were sequenced at the insert region using the forward sequencing primer and Sequenase 2.0 (Amersham, Arlington Heights, Ill.) according to the manufacturer's protocol.

Determination of the apparent equilibrium dissociation constants and the dissociation rate constants. The binding of ssDNA ligands at low concentrations to varying concentrations of PDGF was determined by the nitrocellulose filter binding method as described (Green et al. (1995) Chemistry and Biology 2:683-695). The concentrations of PDGF stock solutions (in PBS) were determined from the absorbance readings at 280 nm using the following $\in_{280}$ values calculated from the amino acid sequences (Gill and von Hippel (1989) Anal. Biochem. 182:319-326): 19,500 M$^{-1}$ cm$^{-1}$ for PDGF-AA, 15,700 M$^{-1}$ cm$^{-1}$ for PDGF-AB and 11,800 M$^{-1}$ cm$^{-1}$ for PDGF-BB. ssDNA for all binding experiments were purified by electrophoresis on 8% (>80 nucleotides) or 12% (<40 nucleotides) polyacrylamide/7 M urea gels. All ssDNA ligands were heated at 90° C. in binding buffer at high dilution (~1 nM) for 2 min and cooled on ice prior to further dilution into the protein solution. The binding mixtures were typically incubated for 15 min at 37° C. before partitioning on nitrocellulose filters.

The binding of DNA ligands (L) to PDGF-AA (P) is adequately described with the bimolecular binding model for which the fraction of bound DNA at equilibrium (q) is given by eq. 1, $$q = (f/2[L]_t)\{[P]_t+[L]_t+K_d-[([P]_t+[L]_t+K_d)^2-4[P]_t[L]_t]^{1/2}\} \quad (1)$$

where $[P]_t$ and $[R]_t$ are total protein and total DNA concentrations, $K_d$ is the equilibrium dissociation constant and f is the efficiency of retention of protein-DNA complexes on nitrocellulose filters (Irvine et al. (1991) J. Mol. Biol. 222: 739-761; Jellinek et al. (1993) Proc. Natl. Acad. Sci. USA 90:11227-11231).

The binding of DNA ligands to PDGF-AB and PDGF-BB is biphasic and can be described by a model in which the DNA ligand is composed of two non-interconverting components ($L_1$ and $L_2$) that bind to the protein with different affinities, described by corresponding dissociation constants, $K_{d1}$ and $K_{d2}$ (Jellinek et al. (1993) Proc. Natl. Acad. Sci. USA 90:11227-11231). In this case, the explicit solution for the fraction of bound DNA (q) is given by eq. 2, $$q = f\left(\frac{X_1 K_{d1}}{1+K_{d1}[P]} + \frac{X_2 K_{d2}}{1+K_{d2}[P]}\right)[P] \quad (2)$$

with $$[P] = \frac{[P]_t}{1 + \frac{X_1 K_{d1}[L]_t}{1+K_{d1}[P]} + \frac{X_2 K_{d2}[L]_t}{1+K_{d2}[P]}}$$

where $X_1$ and $X_2(=1-X_1)$ are the mole fractions of $L_1$ and $L_2$. The $K_d$ values for the binding of DNA ligands to PDGF were calculated by fitting the data points to eq. 1 (for PDGF-AA) or eq. 2 (for PDGF-AB and PDGF-BB) using the non-linear least squares method.

The dissociation rate constants ($k_{off}$) were determined by measuring the amount of $^{32}$P 5'-end labeled minimal ligands (0.17 nM) bound to PDGF-AB (1 nM) as a function of time following the addition of 500-fold excess of unlabeled ligands, using nitrocellulose filter binding as the partitioning method. The $k_{off}$ values were determined by fitting the data points to the first-order rate equation (eq. 3)

$$(q-q_8)/(q_0-q_8) = \exp(-k_{off}t) \quad (3)$$

where q, $q_0$ and $q_8$ represent the fractions of DNA bound to PDGF-AB at any time (t), t=0 and t=8, respectively.

Minimal ligand determinations. To generate a population of 5' end-labeled DNA ligands serially truncated from the 3' end, a primer complementary to the 3' invariant sequence region of a DNA ligand template (truncated primer 5N2, Table 1) (SEQ ID NO: 3) was radiolabeled at the 5' end with [γ$^{32}$P]-ATP and T4 polynucleotide kinase, annealed to the template and extended with Sequenase (Amersham, Arlington Heights, Ill.) and a mixture of all four dNTPs and ddNTPs. Following incubation in binding buffer for 15 min at 37° C., the fragments from this population that retain high affinity binding to PDGF-AB were separated from those with weaker affinity by nitrocellulose filter partitioning. Electrophoretic resolution of the fragments on 8% polyacrylamide/7 M urea gels, before and after affinity selection, allows determination of the 3' boundary. To generate a population of 3' end-labeled DNA ligands serially truncated from the 5' end, the DNA ligands were radiolabeled at the 3' end with [α-$^{32}$P]-cordycepin-5'-triphosphate (New England Nuclear, Boston, Mass.) and T4 RNA ligase (Promega, Madison, Wis.), phosphorylated at the 5' end with ATP and T4 polynucleotide kinase, and partially digested with lambda exonuclease (Gibco BRL, Gaithersburg, Md.). Partial digestion of 10 pmols of 3'-labeled ligand was done in 100 µL volume with 7 mM glycine-KOH (pH 9.4), 2.5 mM MgCl$_2$, 1 µg/ml BSA, 15 µg tRNA, and 4 units of lambda exonuclease for 15 min at 37°. The 5' boundary was determined in an analogous manner to that described for the 3' boundary.

Melting temperature ($T_m$) measurements. Melting profiles for the minimal DNA ligands were obtained on a Cary Model 1E spectrophotometer. Oligonucleotides (320-400 nM) were heated to 95° C. in PBS, PBSM or PBS with 1 mM EDTA and cooled to room temperature prior to the melting profile determination. Melting profiles were generated by heating the samples at the rate of 1° C./min from 15-95° C. and recording the absorbance every 0.1° C. The first derivative of the data points was calculated using the plotting program Kaleida-Graph (Synergy Software, Reading, Pa.). The first derivative values were smoothed using a 55 point smoothing function by averaging each point with 27 data points on each side. The peak of the smoothed first derivative curves was used to estimate the $T_m$ values.

Crosslinking of 5-iodo-2'-deoxyuridine-substituted DNA ligands to PDGF-AB. DNA ligands containing single or multiple substitutions of 5'-iodo-2'-deoxyuridine for thymidine were synthesized using the solid phase phosphoramidite method. To test for the ability to crosslink, trace amounts of 5' $^{32}$P end-labeled ligands were incubated with PDGF-AB (100 nM) in binding buffer at 37° C. for 15 min prior to irradiation. The binding mixture was transferred to a 1 cm path length cuvette thermostated at 37° C. and irradiated at 308 nm for 25-400 s at 20 Hz using a XeCl charged Lumonics Model EX748 excimer laser. The cuvette was positioned 24 cm beyond the focal point of a convergent lens, with the energy at the focal point measuring 175 mjoules/pulse. Following irradiation, aliquots were mixed with an equal volume of formamide loading buffer containing 0.1% SDS and incubated at 95° C. for 5 min prior to resolution of the crosslinked PDGF/ligand complex from the free ligand on 8% polyacrylamide/7 M urea gels.

To identify the protein site of crosslinking for ligand 20t-I4 (SEQ ID NO: 92), binding and irradiation were done on a larger scale. PDGF-AB and 51 $^{32}$P end-labeled ligand, each at 1 μM in PBSM, were incubated and irradiated (300 s) as described above in two 1 ml reaction vessels. The reaction mixtures were combined, ethanol precipitated and resuspended in 0.3 ml of Tris-HCl buffer (100 mM, pH 8.5). The PDGF-AB/ligand crosslinked complex was digested with 0.17 μg/μl of modified trypsin (Boehringer Mannheim) for 20 hours at 37° C. The digest mixture was extracted with phenol/chloroform, chloroform and then ethanol precipitated. The pellet was resuspended in water and an equal volume of formamide loading buffer with 5% (v/v) β-mercaptoethanol (no SDS), incubated at 95° C. for 5 min, and resolved on a 40 cm 8% polyacrylamide/7 M urea gel. The crosslinked tryptic-peptide/ligand that migrated as two closely spaced bands about 1.5 cm above the free ligand band was excised from the gel and eluted by the crush and soak method and ethanol precipitated. The dried crosslinked peptide (about 160 pmoles based on the specific activity) was sequenced by Edman degradation (Midwest Analytical, Inc., St. Louis, Mo.).

Receptor Binding Assay. The binding of $^{125}$I-PDGF-AA and $^{125}$I-PDGF-BB to porcine aortic endothelial (PAE) cells transfected with PDGF α- or β-receptors were performed as described (Heldin et al., (1988) EMBO J. 7:1387-1394). Different concentrations of DNA ligands were added to the cell culture (1.5 cm$^2$) in 0.2 ml of phosphate buffered saline supplemented with 1 mg bovine serum albumin per ml together with $^{125}$I-PDGF-AA (2 ng, 100,000 cpm) or $^{125}$I-PDGF-BB (2 ng, 100,000 cpm). After incubation at 4° C. for 90 min, the cell cultures were washed and cell associated radioactivity determined in a g-counter (Heldin et al., (1988) EMBO J. 7:1387-1394).

[$^3$H]thymidine Incorporation Assay. The incorporation of [$^3$H]thymidine into PAE cells expressing PDGF β-receptor in response to 20 ng/ml of PDGF-BB or 10% fetal calf serum and in the presence of different concentrations of DNA ligands was performed as described (Mori et al. (1991) J. Biol. Chem. 266:21158-21164). After incubation for 24 h at 37° C., $^3$H-radioactivity incorporated into DNA was determined using a β-counter.

EXAMPLE 2 ssDNA Ligands of PDGF

High affinity DNA ligands to PDGF AB were identified by the SELEX process from a library of ~3×10$^{14}$ molecules (500 pmol) of single stranded DNA randomized at forty contiguous positions (Table 1) (SEQ ID NO: 1). The PDGF-bound DNA was separated from unbound DNA by polyacrylamide gel electrophoresis in the first round and by nitrocellulose filter binding in the subsequent rounds. After 12 rounds of SELEX, the affinity-enriched pool bound to PDGF-AB with an apparent dissociation constant ($K_t$) of ~50 pM (data not shown). This represented an improvement in affinity of ~700-fold compared to the initial randomized DNA library. This affinity-enriched pool was used to generate a cloning library from which 39 isolates were sequenced. Thirty-two of these ligands were found to have unique sequences (Table 2) (SEQ ID NOS: 4-35). Ligands that were subjected to the minimal sequence determination are marked with an asterisk (*) next to the clone number. The clone numbers that were found to retain high affinity binding as minimal ligands are italicized. All ligands shown in Table 2 were screened for their ability to bind to PDGF AB using the nitrocellulose filter binding method. To identify the best ligands from this group, the relative affinities for PDGF-AB were determined by measuring the fraction of 5' $^{32}$P end-labeled ligands bound to PDGF-AB over a range of protein concentrations. For the ligands that bound to PDGF-AB with high affinity, the affinity toward PDGF-BB and PDGF-AA was also examined: in all cases, the affinity of ligands for PDGF-AB and PDGF-BB was comparable while the affinity for PDGF-AA was considerably lower (data not shown).

Twenty-one of the thirty-two unique ligands can be grouped into a sequence family shown in Table 3 (SEQ ID NOS: 4, 5, 7-9, 14-24, 26, 31, 32, 34 and 35). The sequences of the initially randomized region (uppercase letters) are aligned according to the consensus three-way helix junction motif. Nucleotides in the sequence-invariant region (lowercase letters) are only shown where they participate in the predicted secondary structure. Several ligands were "disconnected" (equality symbol) in order to show their relatedness to the consensus motif through circular permutation. The nucleotides predicted to participate in base pairing are indicated with underline inverted arrows, with the arrow heads pointing toward the helix junction. The sequences are divided into two groups, A and B, based on the first single stranded nucleotide (from the 5' end) at the helix junction (A or G, between helices II and III). Mismatches in the helical regions are shown with dots under the corresponding letters (G-T and T-G base pairs were allowed). In places where single nucleotide bulges occur, the mismatched nucleotide is shown above the rest of the sequence between its neighbors.

This classification is based in part on sequence homology among these ligands, but in greater part on the basis of a shared secondary structure motif: a three-way helix junction with a three nucleotide loop at the branch point (FIG. 1) (SEQ ID NO: 82). These ligands were subdivided into two groups; for ligands in group A, the loop at the branch point has an invariant sequence AGC and in group B, that sequence is G(T/G)(C/T). The proposed consensus secondary structure motif is supported by base-pairing covariation at non-conserved nucleotides in the helices (Table 4). Since the three-way junctions are encoded in continuous DNA strands, two of the helices end in loops at the distal end from the junction. These loops are highly variable, both in length and in sequence. Furthermore, through circular permutation of the consensus motif, the loops occur in all three helices, although they are most frequent in helices II and III. Together these observations suggest that the regions distal from the helix junction are not important for high affinity binding to PDGF-AB. The highly conserved nucleotides are indeed found near the helix junction (Table 3, FIG. 1).

EXAMPLE 3

Minimal Ligand Determinations

The minimal sequence necessary for high affinity binding was determined for six of the best ligands to PDGF-AB. In general, the information about the 3' and 5' minimal sequence boundaries can be obtained by partially fragmenting the nucleic acid ligand and then selecting for the fragments that retain high affinity for the target. With RNA ligands, the fragments can be conveniently generated by mild alkaline hydrolysis (Tuerk et al. (1990) J. Mol. Biol. 213: 749-761; Jellinek et al. (1994) Biochemistry 33:10450-10456; Jellinek et al. (1995) Biochemistry 34:11363-11372; Green et al. (1995) J. Mol. Biol. 247:60-68). Since DNA is more resistant to base, an alternative method of generating fragments is needed for DNA. To determine the 3' boundary, a population of ligand fragments serially truncated at the 3' end was generated by extending the 5' end-labeled primer annealed to the 3' invariant sequence of a DNA ligand using the dideoxy sequencing method. This population was affinity-selected by nitrocellulose filtration and the shortest fragments (truncated from the 3' end) that retain high affinity binding for PDGF-AB were identified by polyacrylamide gel electrophoresis. The 5' boundary was determined in an analogous manner except that a population of 3' end-labeled ligand fragments serially truncated at the 5' end was generated by limited digestion with lambda exonuclease. The minimal ligand is then defined as the sequence between the two boundaries. It is important to keep in mind that, while the information derived from these experiments is useful, the suggested boundaries are by no means absolute since the boundaries are examined one terminus at the time. The untruncated (radiolabeled) termini can augment, reduce or have no effect on binding (Jellinek et al. (1994) Biochemistry 33:10450-10456).

Of the six minimal ligands for which the boundaries were determined experimentally, two (20t (SEQ ID NO: 83) and 41t (SEQ ID NO: 85); truncated versions of ligands 20 and 41) bound with affinities comparable (within a factor of 2) to their full-length analogs and four had considerably lower affinities. The two minimal ligands that retained high affinity binding to PDGF, 20t and 41t, contain the predicted three-way helix junction secondary structure motif (FIG. 2) (SEQ ID NOS: 83-85). The sequence of the third minimal ligand that binds to PDGF-AB with high affinity, 36t, was deduced from the knowledge of the consensus motif (FIG. 2). In subsequent experiments, we found that the single-stranded region at the 5' end of ligand 20t is not important for high affinity binding. Furthermore, the trinucleotide loops on helices II and III in ligand 36t (GCA and CCA) can be replaced with hexaethylene glycol spacers (infra). These experiments provide further support for the importance of the helix junction region in high affinity binding to PDGF-AB.

Figure 3A:
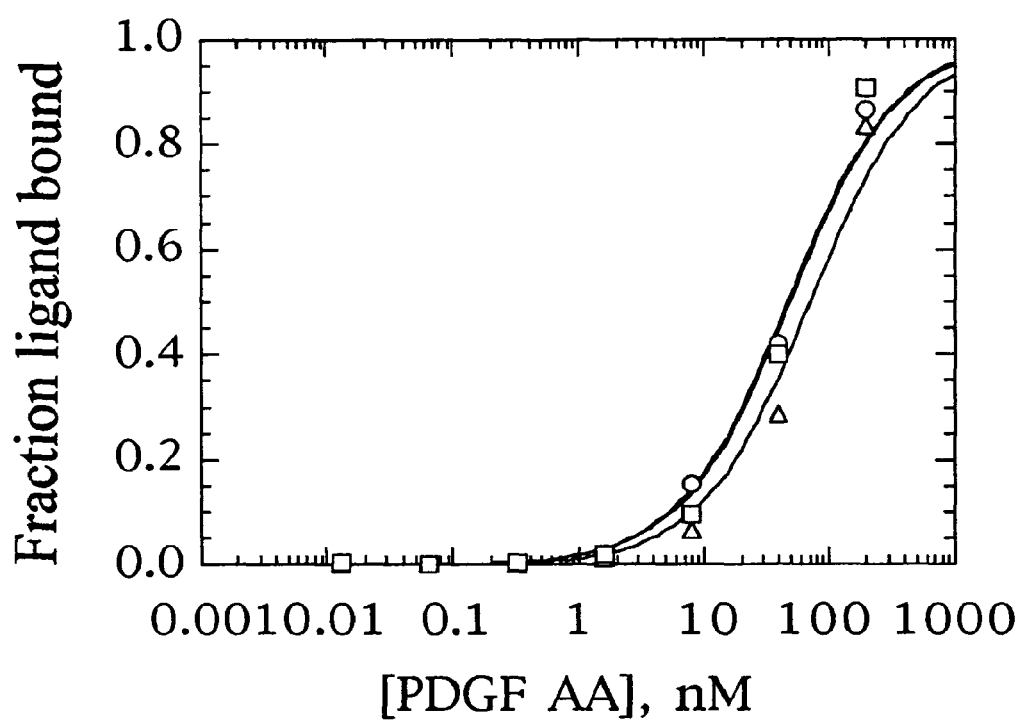
FIGS. 3A-3C show the binding of minimal high affinity DNA ligands to PDGF AA, PDGF AB, and PDGF BB, respectively. The fraction of $^{32}$P 5' end-labeled DNA ligands bound to varying concentrations of PDGF was determined by the nitrocellulose filter binding method. Minimal ligands tested were 20t (o), 36t (?), and 41t (?). Oligonucleotide concentrations in these experiments were ~10 pM (PDGF-AB and PDGF-BB) and ~50 pM (PDGF AA). Data points were fitted to eq. 1 (for binding of the DNA ligands to PDGF-AA) or to eq. 2 (for binding to PDGF AB and BB) using the non-linear least squares method. Binding reactions were done at 37° C. in binding buffer (PBSM with 0.01% HSA).
Figure 3B:
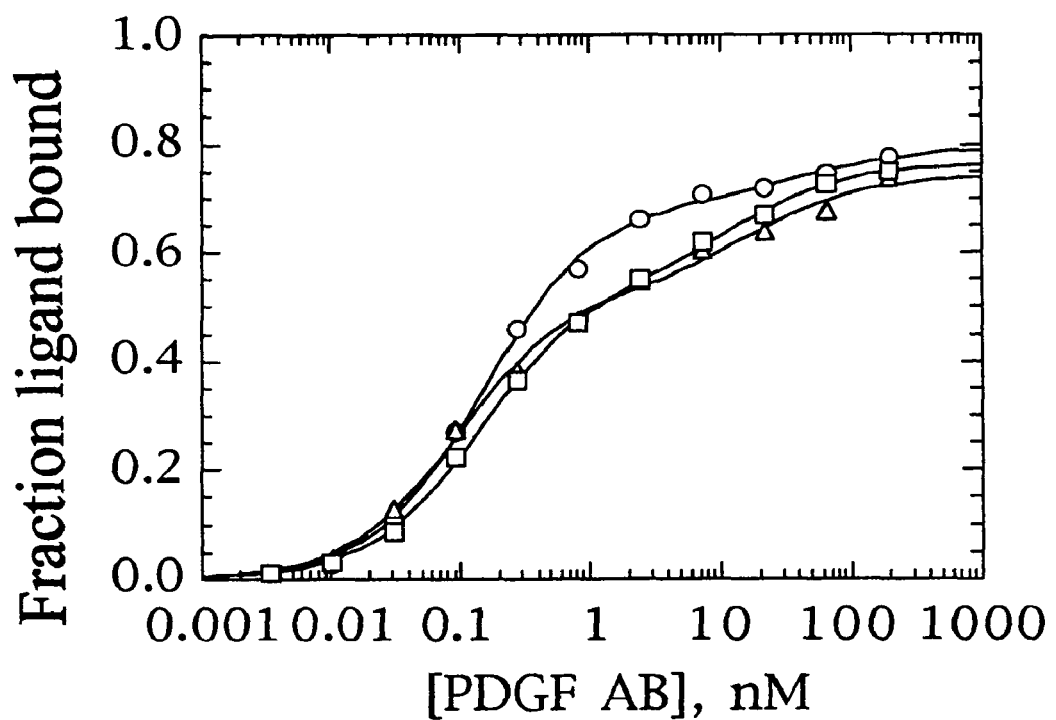
Figure 3C:
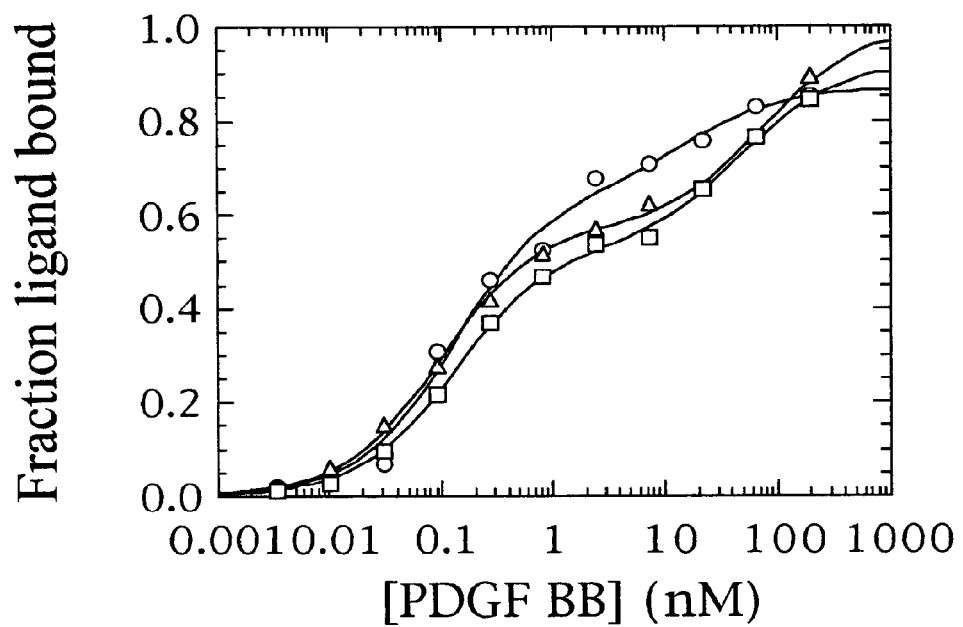

Binding of the Minimal Ligands to PDGF. The binding of minimal ligands 20t, 36t, and 41t to varying concentrations of PDGF-A, PDGF-AB and PDGF-BB is shown in FIGS. 3A-3C. In agreement with the binding properties of their full length analogs, the minimal ligands bind to PDGF-AB and PDGF-BB with substantially higher affinity than to PDGF AA (FIGS. 3A-3C, Table 5). In fact their affinity for PDGF-AA is comparable to that of random DNA (data not shown). The binding to PDGF-A is adequately described with a monophasic binding equation while the binding to PDGF-AB and PDGF-BB is notably biphasic. In previous SELEX experiments, biphasic binding has been found to be a consequence of the existence of separable nucleic acid species that bind to their target protein with different affinities (Jellinek et al. (1995) Biochemistry 34:11363-11372) and unpublished results). The identity of the high and the low affinity fractions is at present not known. Since these DNA ligands described here were synthesized chemically, it is possible that the fraction that binds to PDGF-AB and PDGF-BB with lower affinity represents chemically imperfect DNA. Alternatively, the high and the low affinity species may represent stable conformational isomers that bind to the PDGF B-chain with different affinities. In any event, the higher affinity binding component is the most populated ligand species in all cases (FIGS. 3A-3C). For comparison, a 39-mer DNA ligand that binds to human thrombin with a $K_d$ of 0.5 nM (ligand T39 (SEQ ID NO.: 88)): 5'-CAGTCCGTGGTAGGGCAGGT-TCGGGTGACTTCGTCGAA[3'T], where [3'T] represents a 3'-3' linked thymidine nucleotide added to reduce 3'-exonuclease degradation) and has a predicted stem-loop structure, binds to PDGF-AB with a $K_d$ of 0.23 µM (data not shown).

Figure 4:
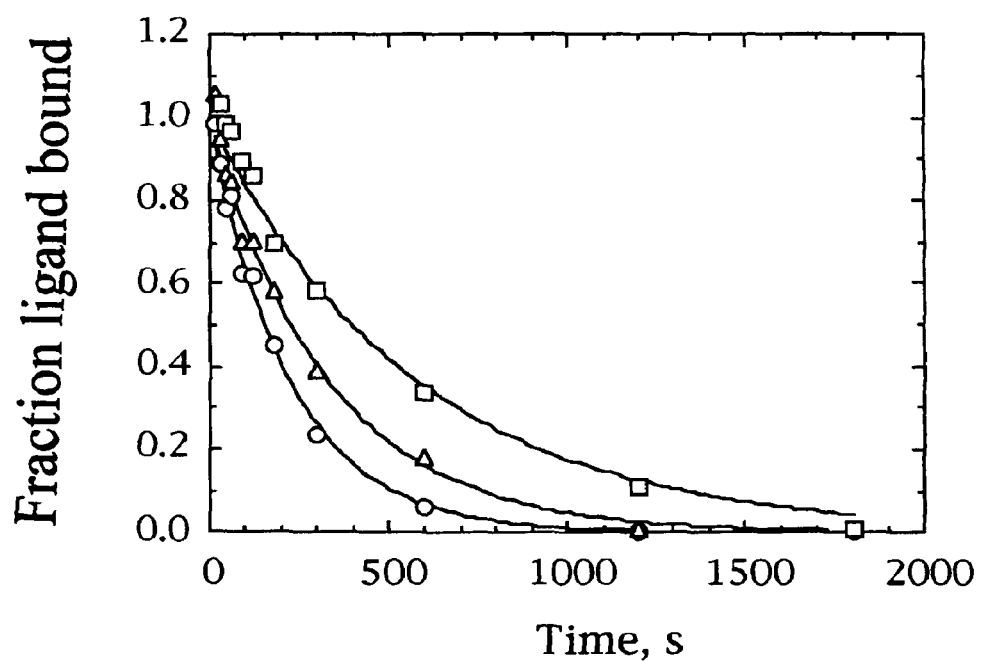
FIG. 4 shows the dissociation rate determination for the high affinity interaction between the minimal DNA ligands and PDGF AB. The fraction of 5' $^{32}$P end-labeled ligands 20t (o), 36t (?), and 41t (?), all at 0.17 nM, bound to PDGF AB (1 nM) was measured by nitrocellulose filter binding at the indicated time points following the addition of a 500-fold excess of the unlabeled competitor. The dissociation rate constant ($k_{off}$) values were determined by fitting the data points to eq 3 in Example 1. The experiments were performed at 37° C. in binding buffer.

Dissociation Rates of the Minimal Ligands. To evaluate the kinetic stability of the PDGF-AB/DNA complexes, the dissociation rates at 37° C. for the complexes of minimal ligands 20t, 36t and 41t with PDGF-AB were determined by measuring the amount of radiolabeled ligands (0.17 nM) bound to PDGF-AB (1 nM) as a function of time following the addition of a large excess of unlabeled ligands (FIG. 4). At these protein and DNA ligand concentrations, only the high affinity fraction of the DNA ligands binds to PDGF-AB.

The following values for the dissociation rate constants were obtained by fitting the data points shown in FIG. 4 to the first-order rate equation. $4.5\pm0.2\times10^{-3}$ s$^{-1}$ ($t_{1/2}$=2.6 min) for ligand 20t, $3.0\pm0.2\times10^{-3}$ s$^{-1}$ ($t_{1/2}$3.8 min) for ligand 36t, and $1.7\pm0.1\times10^{-3}$ s$^{-1}$ ($t_{1/2}$=6.7 min) for ligand 41 t. The association rates calculated for the dissociation constants and dissociation rate constants ($k_{on}$=$k_{off}$/$K_d$) are $3.1\times10^7$M$^{-1}$ s$^{-1}$ for 20t, $3.1\times10^7$M$^{-1}$ s$^{-1}$ for 36t and $1.2\times10^7$M$^{-1}$ s$^{-1}$ for 41t.

Figure 5:
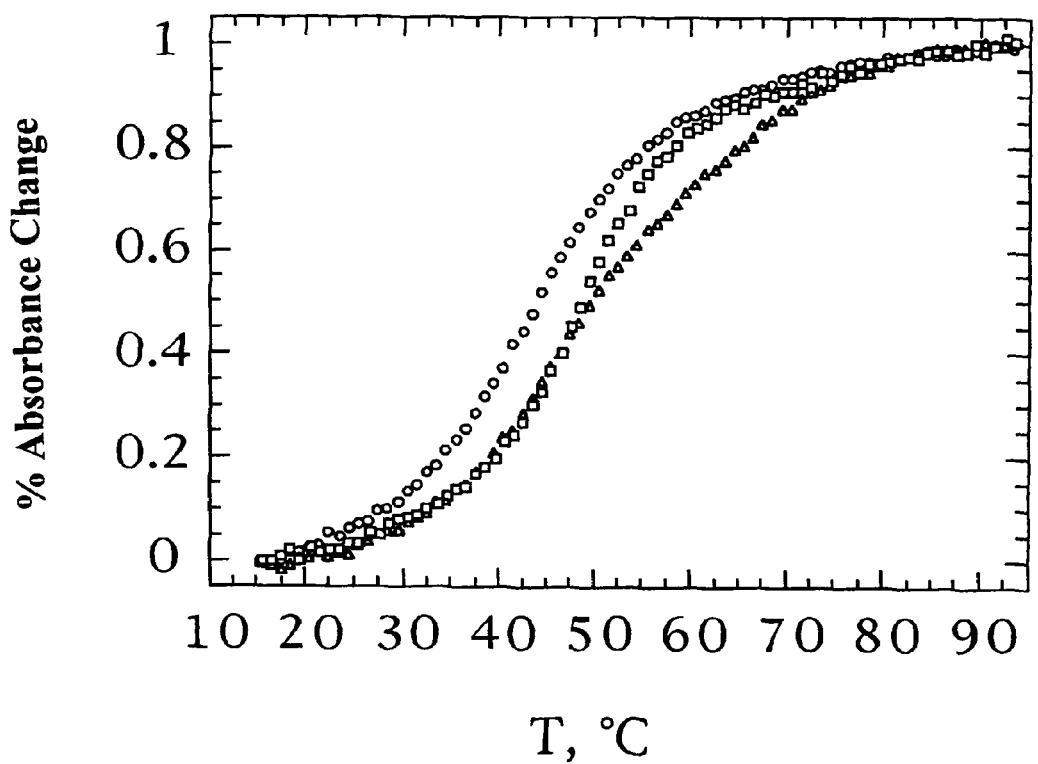
FIG. 5 shows the thermal denaturation profiles for the minimal high affinity DNA ligands to PDGF-AB. The change in absorbance at 260 nm was measured in PBS containing 1 mM $MgCl_2$ as a function of temperature for ligands 20t (o), 36t (?), and 41t (?).

Melting Temperatures of the Minimal Ligands. Melting temperatures ($T_m$'s) were determined for minimal ligands 20t, 36t and 41t from the UV absorption vs. temperature profiles (FIG. 5). At the oligonucleotide concentrations used in these experiments (320-440 nM), only the monomeric species were observed as single bands on non-denaturing polyacrylamide gels. The $T_m$ values were obtained from the first derivative replots of the melting profiles. Ligands 20t and 41 t exhibited monophasic melting with $T_m$ values of 44° C. and 49° C. The melting profile of ligand 36t was biphasic, with the Tm value of 44° C. for the first (major) transition and ~63° C. for the second transition.

Photocrosslinking of 5-Iodo-2'-Deoxyuridine Substituted Minimal DNA Ligands to PDGF-AB. To determine the sites on the DNA ligands and PDGF that are in close contact, a series of photo-crosslinking experiments was performed with 5'-iodo-2'-deoxyuridine (IdU)-substituted DNA ligands 20t, 36t and 41t. Upon monochromatic excitation at 308 nm, 5-iodo- and 5-bromo-substituted pyrimidine nucleotides populate a reactive triplet state following intersystem crossing from the initial n to π* transition. The excited triplet state species then reacts with electron rich amino acid residues (such as Trp, Tyr and His) that are in its close proximity to yield a covalent crosslink. This method has been used extensively in studies of nucleic acid-protein interactions since it allows irradiation with >300 nm light which minimizes photodamage (Willis et al. (1994) Nucleic Acids Res. 22:4947-4952; Stump and Hall (1995) RNA 1:55-63; Willis et al. (1993) Science 262:1255-1257; Jensen et al. (1995) Proc. Natl. Acad. Sci. U.S.A. 92:12220-12224). Analogs of ligands 20t, 36t and 41t were synthesized in which all thymidine residues were replaced with IdU residues using the solid phase phosphoramidite method. The affinity of these IdU-substituted ligands for PDGF-AB was somewhat enhanced compared to the unsubstituted ligands and based on the appearance of bands with slower electrophoretic mobility on 8% polyacrylamide/7 M urea gels, all three 5' end-labeled IdU-substituted ligands crosslinked to PDGF-AB upon irradiation at 308 nm (data not shown). The highest crosslinking efficiency was observed with IdU-substituted ligand 20t. To identify the specific IdU position(s) responsible for the observed crosslinking, seven singly or multiply IdU-substituted analogs of 20t were tested for their ability to photo-crosslink to PDGF-AB: ligands 20t-I1 through 20t-I7 (5'-TGGGAGGGGCGCGT$^1$T$^1$CT$^1$T$^1$CGT$^2$GGT$^3$T$^4$ACT$^5$T$^6$T$^6$T$^6$AGT$^7$CCCCG-3' (SEQ ID NOS.: 89-95) where the numbers indicate IdU substitutions at indicated thymidine nucleotides for the seven ligands). Of these seven ligands, efficient crosslinking to PDGF-AB was observed only with ligand 20t-I4 (SEQ ID NO: 92). The photo-reactive IdU position corresponds to the 3' proximal thymidine in the loop at the helix junction (FIG. 2).

To identify the crosslinked amino acid residue(s) on PDGF-AB, a mixture of 5' end-labeled 20t-I4 and PDGF-AB was incubated for 15 min at 37° C. followed by irradiation at 308 nm. The reaction mixture was then digested with modified trypsin and the crosslinked fragments resolved on an 8% polyacrylamide/7 M urea gel. Edman degradation of the peptide fragment recovered from the band that migrated closest to the free DNA band revealed the amino acid sequence KKPIXKK (SEQ ID NO: 96), where X indicates a modified amino acid that could not be identified with the 20 derivatized amino acid standards. This peptide sequence, where X is phenylalanine, corresponds to amino acids 80-86 in the PDGF-B chain (Johnsson et al. (1984) EMBO J. 3:921-928) which in the crystal structure of PDGF-BB comprises a part of solvent-exposed loop 111 (Oefner et al. (1992) EMBO J. 11:3921-3926). In the PDGF A-chain, this peptide sequence does not occur (Betsholtz et al. (1986) Nature 320:695-699). Together, these data establish a point contact between a specific thymidine residue in ligand 20t and phenylalanine 84 of the PDGF B-chain.

Figure 6:
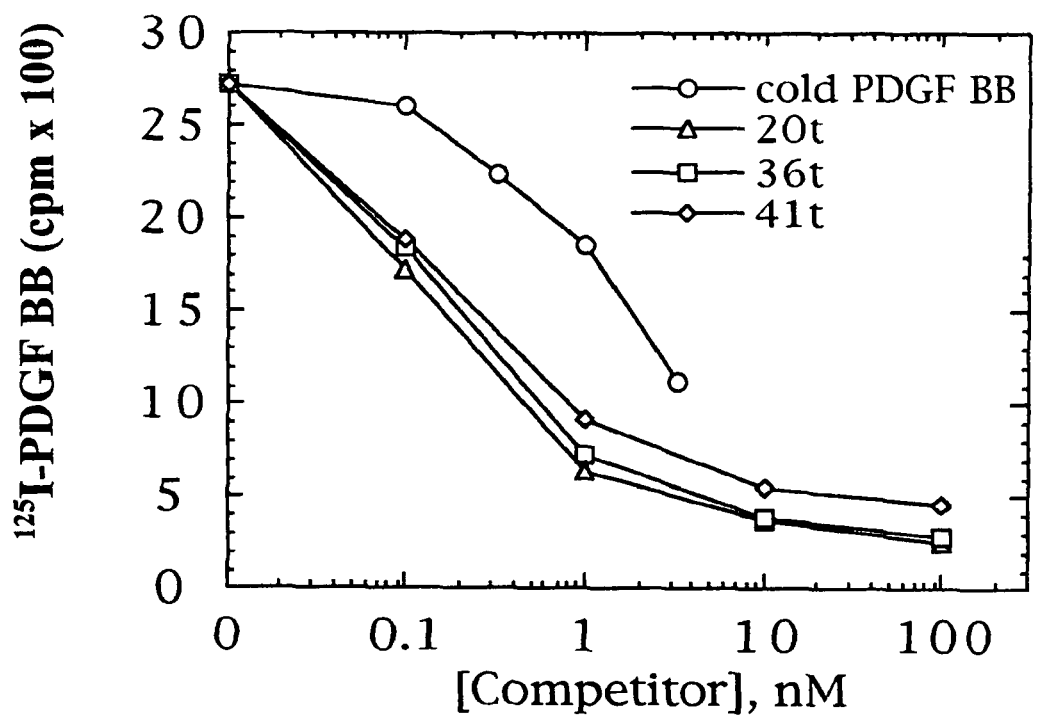
FIG. 6 shows the effect of DNA ligands on the binding of $^{125}$I-PDGF-BB to PDGF a-receptors expressed in PAE cells.

Receptor Binding Assay. In order to determine whether the DNA ligands to PDGF were able to inhibit the effects of PDGF isoforms on cultured cells, the effects on binding of $^{125}$I-labeled PDGF isoforms to PDGF α- and β-receptors stably expressed in porcine aortic endothelial (PAE) cells by transfection were first determined. Ligands 20t, 36t and 41t all efficiently inhibited the binding of $^{125}$I-PDGF-BB to PDGF a-receptors (FIG. 6) or PDGF β-receptors (data not shown), with half maximal effects around 1 nM of DNA ligand. DNA ligand T39 (described supra), directed against thrombin and included as a control, showed no effect. None of the ligands was able to inhibit the binding of $^{125}$I-PDGF-AA to the PDGF α-receptor (data not shown), consistent with the observed specificity of ligands 20t, 36t and 41t for PDGF-BB and PDGF-AB.

Figure 7:
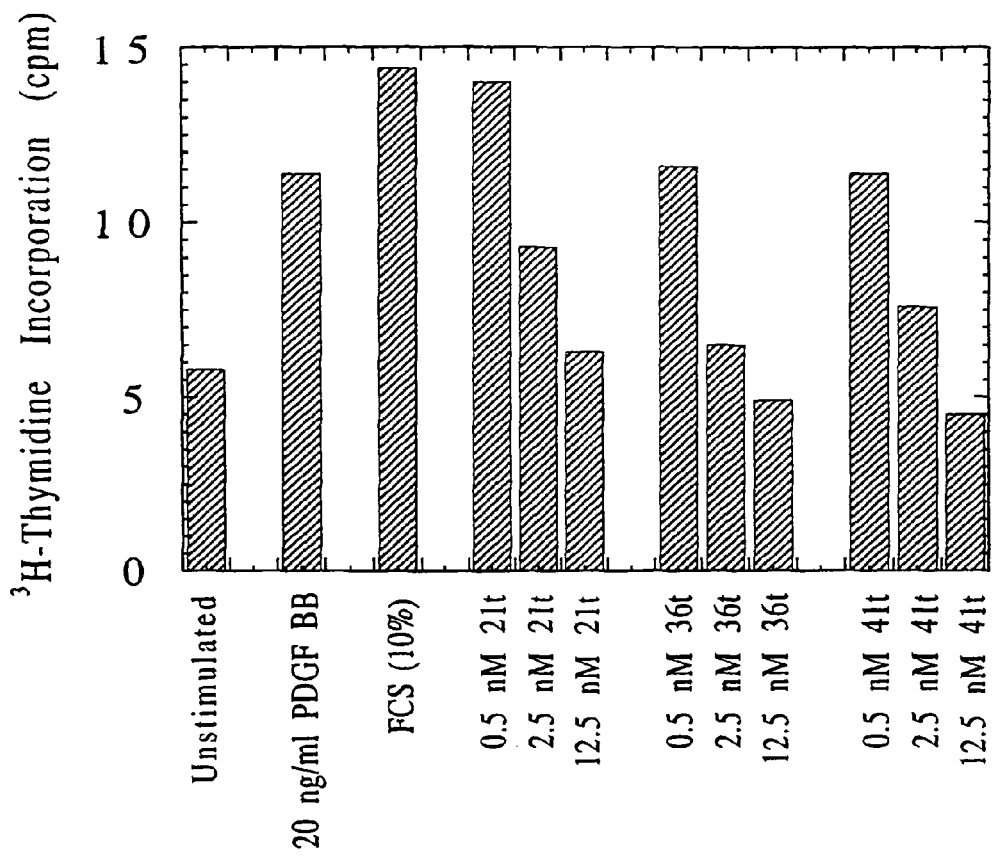
FIG. 7 shows the effect of DNA ligands on the mitogenic effect of PDGF-BB on PAE cells expressing the PDGF β-receptors.

Inhibition of Mitogenic Effects by Minimal Ligands. The ability of the DNA ligands to inhibit the mitogenic effects of PDGF-BB on PAE cells expressing PDGF β-receptors was investigated. As shown in FIG. 7, the stimulatory effect of PDGF-BB on [$^3$H]thymidine incorporation was neutralized by ligands 20t, 36t and 41t. Ligand 36t exhibited half maximal inhibition at the concentration of 2.5 nM; ligands 41t was slightly more efficient and 20t slightly less efficient. The control ligand T39 had no effect. Moreover, none of the ligands inhibited the stimulatory effects of fetal calf serum on [$^3$H]thymidine incorporation in these cells, showing that the inhibitory effects are specific for PDGF.

EXAMPLE 4

Post-SELEX Modifications

The stability of nucleic acids to nucleases is an important consideration in efforts to develop nucleic acid-based therapeutics. Experiments have shown that many, and in some cases most of the nucleotides in SELEX-derived ligands can be substituted with modified nucleotides that resist nuclease digestion, without compromising high affinity binding (Green et al. (1995) Chemistry and Biology 2:683-695; Green et al. (1995) J. Mol. Biol. 247:60-68).

Figure 8A:
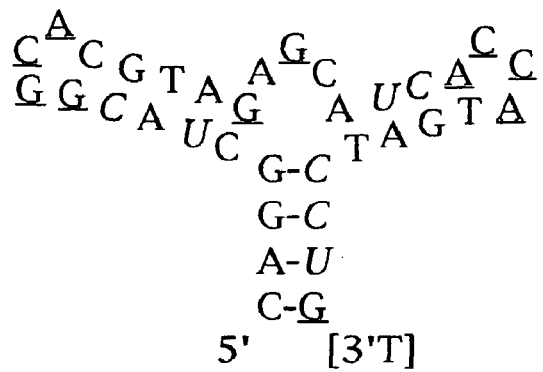
FIGS. 8A-8B show the substitution pattern compatible with high affinity binding to PDGF-AB.
Figure 8B:
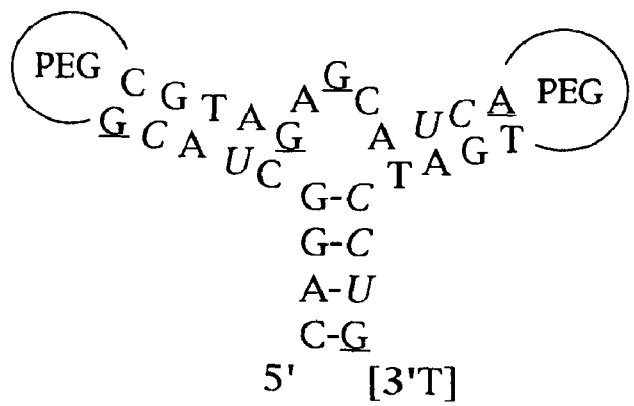

A series of substitution experiments were conducted to identify positions in ligand 36t that tolerate 2'-O-methyl (2'-O-Me) or 2'-fluoro (2'-F) substitution. Tables 6 and 7 and FIGS. 8A and 8B summarize the substitutions examined and their effect on the affinity of the modified ligands for PDGF-AB or PDGF-BB. 2-Fluoropyrimidine nucleoside phosphoramidites were obtained from JBL Scientific (San Louis Obispo, Calif.). 2'-O-Methylpurine phosphoramidites were obtained from PerSeptive Biosystems (Boston, Mass.). All other nucleoside phosphoramidites were from PerSeptive Biosystems (Boston, Mass.). Not all substitution combinations were examined. Nevertheless, these experiments have been used to identify the pattern of 2'-O-Me and 2'-F substitutions that are compatible with high affinity binding to PDGF-AB or PDGF-BB. It is worth noting that trinucleotide loops on helices II and III in ligand 36t (FIGS. 2 and 8B) can be replaced with pentaethylene glycol (18-atom) spacers (Spacer Phosphoramidite 18, Glen Research, Sterling, Va.) (see Example 5 for description of synthesis of pentaethylene glycol-substituted ligand) without compromising high affinity binding to PDGF-AB or -BB. This is in agreement with the notion that the helix junction domain of the ligand represents the core of the structural motif required for high affinity binding. In practical terms, the replacement of six nucleotides with two pentaethylene glycol spacers is advantageous in that it reduces by four the number of coupling steps required for the synthesis of the ligand. In addition to the substitution experiments, four nucleotides from the base of helix I were found that could be deleted without loss of binding affinity (compare for example ligand 36t with 36ta or ligand 1266 with 1295 in Tables 6 and 7).

EXAMPLE 5

Synthesis of Peg-Modified PDGF Nucleic Acid Ligands

A) General Procedure for the Synthesis of NX31975 on Solid Support

Figure 9D:
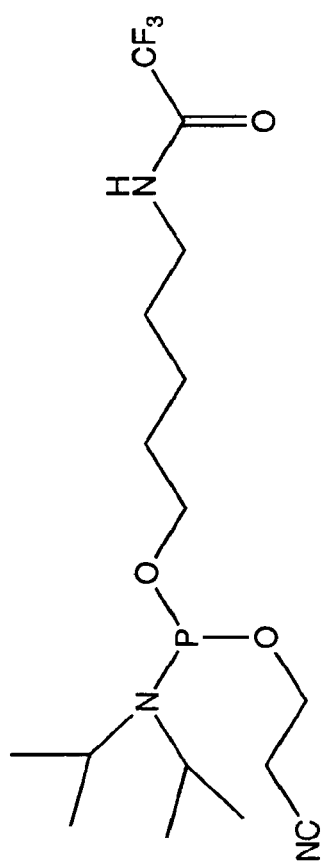
Figure 9E:
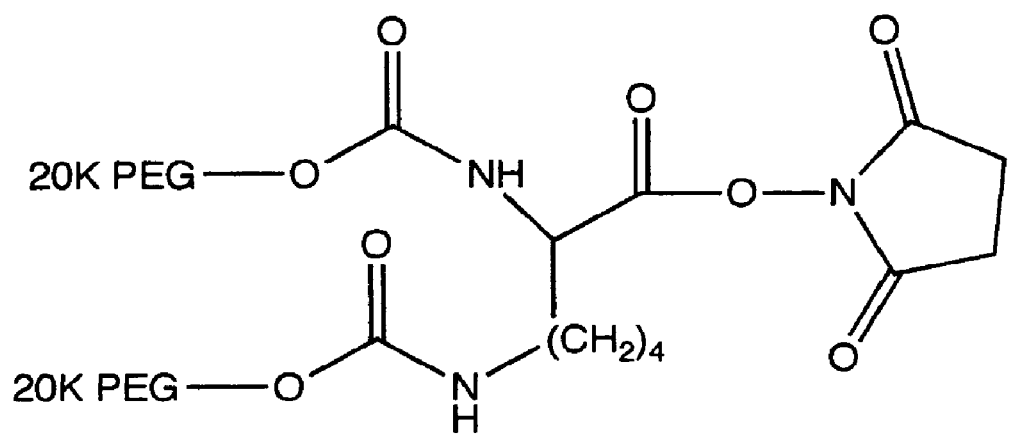

Synthesis was carried out on 1 mmol scale on a millipore 8800 automated synthesizer using standard deoxynucleoside phosphoramidites, 2'-O-methyl-5'-O-DMT-N2-tert-butylphenloxyacetylguanosine-phosphoramidite, 2'-O-methyl-5'-O-DMT-N6-tert-butylphenoxyacetyl-adenosine-phosphoramidite, 2'-deoxy-2'-fluoro-5'-O-DMT-uridine-phosphoramidite, 2'-deoxy-2'-fluoro-5'-O-DMT-N4-acetylcytidine-3-N,N-diisopropyl-(2-cyanoethyl) phosphoramidite, 18-O-DMT-hexaethyleneglycol-1-[N,N- diisopropyl-(2-cyanoethyl)-phosphoramidite] (FIG. 9C), and 5-trifloroacetamidopentane-1-[N,N-diisopropyl-(2-cyanoethyl)-phosphoramidite]. (FIG. 9D). The syntheses were carried out using 4,5-dicyanoimidazole as the activator on controlled pore glass (CPG) support of 600 A pore size, 80-120 mesh, and 60-70 µmol/g loading with 5'-succinyl thymidine.

After the synthesis, the oligos were deprotected with 40% NH$_4$OH, at 55° C. for 16 h. The support was filtered, and washed with water and 1:1 acetonitrile/water and the combined washings were evaporated to dryness. The ammonium counterion on the backbone was exchanged for triethylammonium ion by reverse phase salt exchange and the solvent was evaporated to afford the crude oligo as the triethylammonium salt.

Hexaethylene glycol spacers on the loops are attached to the nucleotides through phosphate linkages. The structures of the 2 loops are shown in FIGS. 9A and 9B. The 5' phosphate group shown is from the hexaethylene glycol phosphoramidite.

B) Conjugation of 40K PEG NHS Ester to the Aminolinker on PDGF Nucleic Acid Ligands The NX31975 crude oligonucleotide containing the 5' primary amino group was dissolved in 100 mM sodium borate buffer (pH 9) to 60 mg/ml concentration. In a separate tube 2 Eq of PEG NHS ester (FIG. 9E) (Shearwater Polymers, Inc.) was dissolved in dry DMF (Ratio of borate: DMF 1:1) and the mixture was warmed to dissolve the PEG NHS ester. Then the oligo solution was quickly added to PEG solution and the mixture was vigorously stirred at room temperature for 10 minutes. About 95% of the oligo conjugated to the PEG NHS ester.

EXAMPLE 6

Stability of Modified Ligands in Serum

Figure 10:
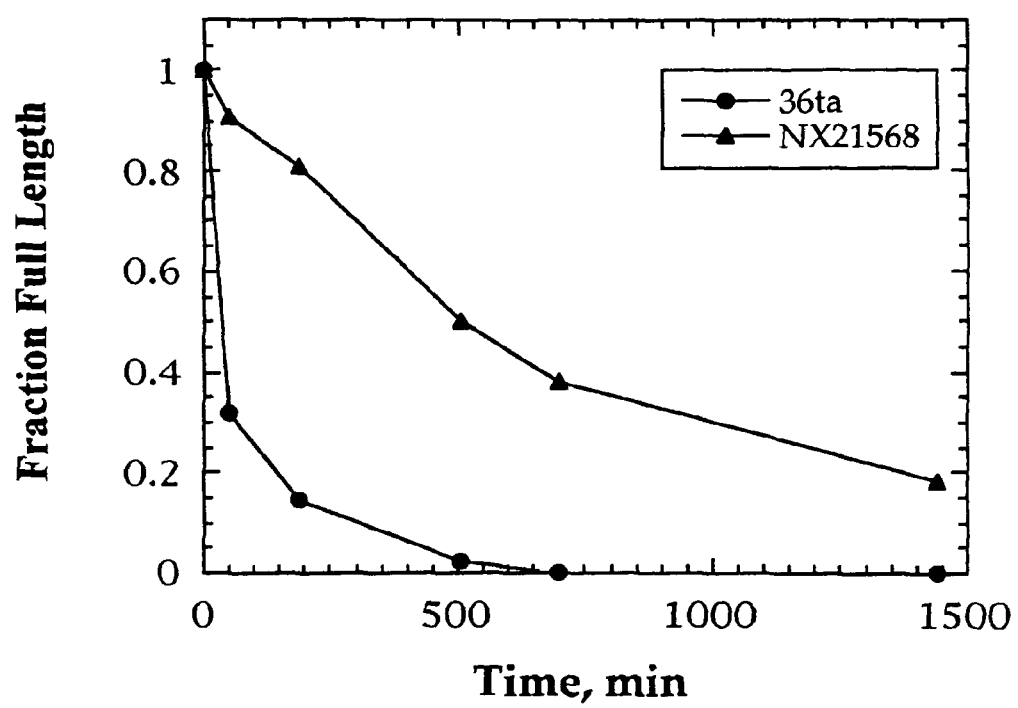
FIG. 10 shows the stabilities of DNA (36ta) and modified DNA (NX21568) Nucleic Acid Ligands in rat serum over time at 37° C. were compared. 36ta and NX21568 are shown by the symbols indicated in the figure.

The stabilities of DNA (36ta) and modified DNA (NX21568) ligands in rat serum at 37° C. were compared. Serum used for these experiments was obtained from a Sprague-Dawley rat and was filtered through 0.45 µm cellulose acetate filter and buffered with 20 mM sodium phosphate buffer. Test ligands (36ta or NX21568) were added to the serum at the final concentration of 500 nM. The final serum concentration was 85% as a result of the addition of buffer and ligand. From the original 900 µl incubation mixture, 100 µl aliquots were withdrawn at various time points and added to 10 µl of 500 mM EDTA (pH 8.0), vortexed and frozen on dry ice and stored at –20° C. until the end of the experiment. The amount of full length oligonucleotide ligand remaining for each of the time points was quantitated by HPLC analysis. To prepare the samples for HPLC injections, 200 µl of a mixture of 30% formamide, 70% 25 mM Tris buffer (pH 8.0) containing 1% acetonitrile was added to 100 µl of thawed time point samples, vortexed for 5 seconds and centrifuged for 20 minutes at 14,000 rpm in an Eppendorf microcentrifuge. The analysis was performed using an anion exchange chromatography column (NuceoPac, Dionex, PA-100, 4×50 mm) applying a LiCl gradient. The amount of full length oligonucleotide remaining at each time point was determined from the peak areas (FIG. 10). With a half-life of about 500 min, the modified ligand (NX21568) exhibited a substantially greater stability in rat serum compared with the DNA ligand (36ta), which was degraded with a half-life of about 35 min (FIG. 10). Thus, the increase in stability in serum results from the 2'-substitutions.

EXAMPLE 7

Efficacy of NX31975-40K PEG in Restenosis

Rat Restenosis Model and Efficacy Results. The plasma residence time of Nucleic Acid Ligands is dramatically improved by the addition of large, inert functional groups such as polyethylene glycol (see for example PCT/US 97/18944). For in vivo efficacy experiments, 40K PEG was conjugated to NX31975 to create NX31975 40K PEG as described in Example 5B (see FIG. 9A for molecular description). Importantly, based on binding experiments, the addition of 40 kDa PEG group at the 5'-end of the ligand does not affect its binding affinity for PDGF-BB.

The effect of selective inhibition of PDGF-B by NX31975-40K PEG was studied in three-month-old male Sprague-Dawley rats (370-450 g). The rats were housed three to a cage with free access to a standard laboratory diet and water. Artificial light was provided 14 hours per day. The experiments were performed in accordance with the institutional guidelines at the Animal Department, Department of Surgery, University Hospital, Uppsala University, Sweden.

A total of 30 rats were randomly allocated to one of two treatment groups: 15 rats in group one received 10 mg/kg body weight of NX31975-40K PEG in phosphate buffered saline (PBS) twice daily delivered by intraperitoneal (i.p.) injections and 15 rats in group two (the control group) received an equal volume of PBS (about 1 ml). The duration of treatment was 14 days. The first injections in both groups were given one hour before arterial injury.

To generate the arterial lesions, all animals were anaesthetized with an i.p. injection of a mixture of one part Fentanyl-fluanisone (Hypnorm vet, fluanisone 10 mg/ml, fentanyl 0.2 mg/ml, Janssen Pharmaceutica, Beerse, Belgium), one part midazolam (Dormicum, Midazolam 5 mg/ml. F. Hoffman-La Roche AG, Basel, Switzerland) and two parts sterile water, 0.33 ml/100 g rat. The distal left common carotid and external carotid arteries were exposed through a midline incision in the neck. The left common carotid artery was traumatized by intraluminal passage of 2F Fogarty embolectomy catheter introduced through the external carotid artery. The catheter was passed three times with the balloon expanded sufficiently with 0.06 ml distilled water to achieve a distension of the carotid itself. The external carotid was ligated after removal of the catheter and the wound was closed. All surgical procedures were performed by a surgeon blinded to the treatment groups.

Fourteen days after the catheter injury, the animals were anesthetized as above. Twenty minutes before the exposure of the abdominal aorta the animals received an intravenous injection of 0.5 ml 0.5% Evans blue dye (Sigma Chemical Co., St. Louis, Mo.) to allow identification of the vessel segment which remained deendothelialized. The carotid arteries were perfused with ice-chilled PBS in situ at 100 mm Hg, via a large cannula placed retrograde in the abdominal aorta until the effluent ran clear via inferior caval vein vent. A distal half of the right and left common carotid arteries, up to the level of the bifurcation, were removed and frozen in liquid nitrogen. Immediately thereafter, the remaining proximal segment was perfusion-fixed through the same aortic cannula at 100 mm Hg pressure with 2.5% glutaraldehyde in phosphate buffer, pH 7.3. Before starting perfusion with PBS, the animals were killed by an overdose of phenobarbital. After approximately 15 minutes of perfusion fixation, the remaining proximal right and left common carotid arteries were retrieved for further preparation, including the aortic arch and innominate artery.

Five sections, approximately 0.5 µm apart, from the middle of the Evans blue stained segment of the left common carotid artery and one section from the contralateral uninjured artery were analyzed per animal with computer-assisted planimetry. The following areas were measured: the area encircled by external elastic lumina (EEL), internal elastic lumina (IEL) and the endoluminal cell layer. Areas for tunical media and tunica intima were calculated. All measurements by an individual blinded to the treatment regimens.

Figure 11:
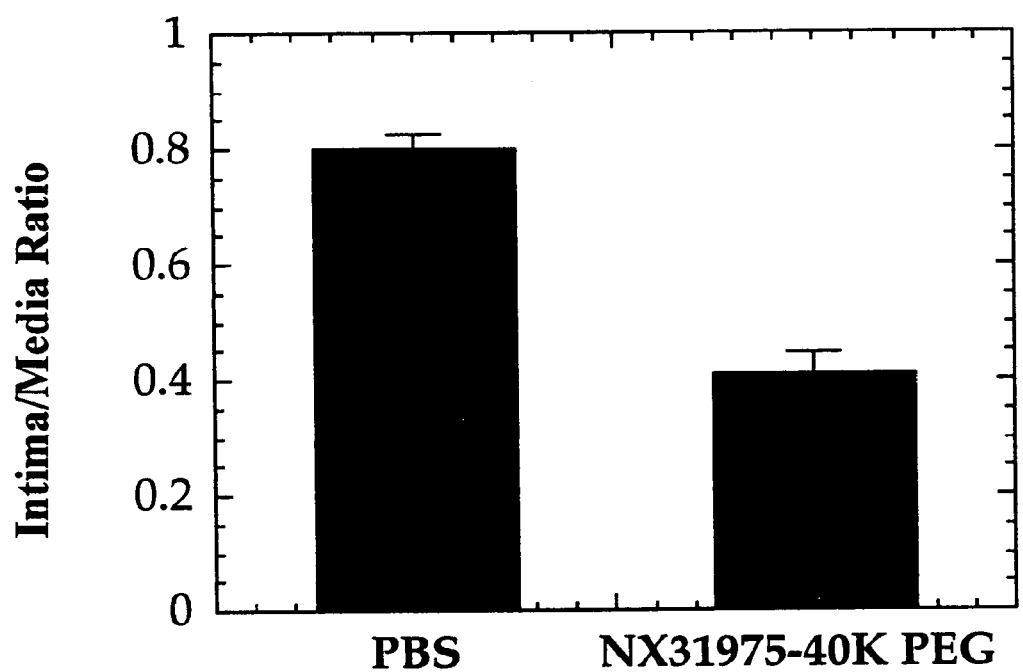
FIG. 11 shows that NX31975-40K PEG significantly inhibited p<0.05) about 50% of the neointima formation in rats based on the intima/media ratio for the control (PBS) and NX31975-40K PEG groups.

Based on values of intima/media ratios for the control and the Nucleic Acid Ligand-treated groups, the PDGF Nucleic Acid Ligand significantly ($p<0.05$) inhibited about 50% of the neointima formation (FIG. 11).

EXAMPLE 8

Antagonism of PDGF in Glomerulonephritis by NX31975-40K PEG

Figure 8C:
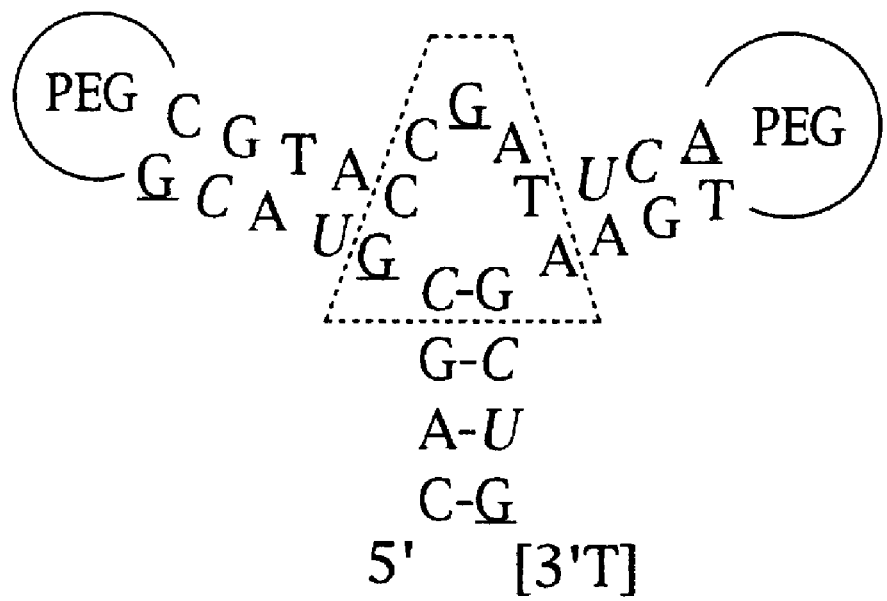

This example provides the general procedures followed and incorporated in Example 9.
Materials and Methods All Nucleic Acid Ligands and their sequence-scrambled controls were synthesized by the solid phase phosphoramidite method on controlled pore glass using an 8800 Milligen DNA Synthesizer and deprotected using ammonium hydroxide at 55° C. for 16 h. The Nucleic Acid Ligand used in experiments described in this example and Example 9 is NX31975 40K PEG (FIG. 9A). NX31975 40K PEG was created by conjugating NX31975 (Table 7) to 40K PEG as described in Example 5. In the sequence-scrambled control Nucleic Acid Ligand, eight nucleotides in the helix junction region of NX31975 were interchanged without formally changing the consensus secondary structure (see FIG. 8C). The binding affinity of the sequence-scrambled control Nucleic Acid Ligand for PDGF BB is ~1 µM, which is 10,000 fold lower compared to NX21617. The sequence-scrambled control Nucleic Acid Ligand was then conjugated to PEG and named NX31976 40K PEG (see FIG. 9B for molecular description). The covalent coupling of PEG to the Nucleic Acid Ligand (or to the sequence-scrambled control) was accomplished as described in Example 5.

Rat PDGF-BB for cross-reactivity binding experiments was derived from *E. coli* transfected with sCR-Script Amp SK(+) plasmid containing the rat PDGF-BB sequence. Rat PDGF-BB sequence was derived rat lung poly A+ RNA (Clonetech, San Diego, Calif.) through RT-PCR using primers that amplify sequence encoding the mature form of PDGF-BB. Rat PDGF-BB protein expression and purification was performed at R&D Systems.
Mesangial Cell Culture Experiments Human mesangial cells were established in culture, characterized and maintained as described previously (Radeke et al. (1994) J. Immunol. 153:1281-1292). To examine the antiproliferative effect of the ligands on the cultured mesangial cells, cells were seeded in 96-well plates (Nunc, Wiesbaden, Germany) and grown to subconfluency. They were then growth-arrested for 48 hours in MCDB 302 medium (Sigma, Deisenhofen, Germany). After 48 hours various stimuli together with either 50 or 10 µg/ml Nucleic Acid Ligand NX31975 40K PEG or 50 or 10 µg/ml sequence-scrambled Nucleic Acid Ligand (NX31976 40K PEG) were added: medium alone, 100 ng/ml human recombinant PDGF-AA, -AB or -BB (kindly provided by J. Hoppe, University of Würzburg, Germany), 100 ng/ml human recombinant epidermal growth factor (EGF; Calbiochem, Bad Soden, Germany) or 100 ng/ml recombinant human fibroblast growth factor-2 (kindly provided by Synergen, Boulder, Colo.). Following 72 hours of incubation, numbers of viable cells were determined using 2,3-bis[2-methoxy-4-nitro-5-sulfophenyl]-2H-tetrazolium-5-carboxanilide (XTT; Sigma) as described (Lonnemann et al. (1995) Kidney Int. 51.837-844).
Experimental Design Anti-Thy 1.1 mesangial proliferative glomerulonephritis was induced in 33 male Wistar rats (Charles River, Sulzfeld, Germany) weighing 150-160 g by injection of 1 mg/kg monoclonal anti-Thy 1.1 antibody (clone OX-7; European Collection of Animal Cell Cultures, Salisbury, England). Rats were treated with Nucleic Acid Ligands or PEG (see below) from day 3 to 8 after disease induction. Treatment consisted of twice daily i.v. bolus injections of the substances dissolved in 400 µl PBS, pH 7.4. The treatment duration was chosen to treat rats from about one day after the onset to the peak of mesangial cell proliferation (Floege et al. (1993) Kidney Int. Suppl. 39:S47-54). Four groups of rats were studied: 1) nine rats, who received NX31975 40K PEG (i.e., a total of 4 mg of the PDGF-B ligand coupled to 15.7 mg 40K PEG); 2) ten rats, who received an equivalent amount of PEG-coupled, scrambled Nucleic Acid Ligand (NX31976 40K PEG); 3) eight rats, who received an equivalent amount (15.7 mg) of 40K PEG alone; 4) six rats, who received 400 µl bolus injections of PBS alone. Renal biopsies for histological evaluation were obtained on days 6 and 9 after disease induction. Twenty-four hour urine collections were performed from days 5 to 6 and 8 to 9 after disease induction. The thymidine analogue 5-bromo-2'-deoxyuridine (BrdU; Sigma, Deisenhofen, Germany; 100 mg/kg body weight) was injected intraperitoneally at 4 hours prior to sacrifice on day 9.

Normal ranges of proteinuria and renal histological parameter (see below) were established in 10 non-manipulated Wistar rats of similar age.
Renal Morphology Tissue for light microscopy and immunoperoxidase staining was fixed in methyl Carnoy's solution (Johnson et al. (1990) Am. J. Pathol. 136:369-374) and embedded in paraffin. Four µm sections were stained with the periodic acid Schiff (PAS) reagent and counterstained with hematoxylin. In the PAS stained sections the number of mitoses within 100 glomerular tufts was determined.
Immunoperoxidase Staining Four mm sections of methyl Carnoy's fixed biopsy tissue were processed by an indirect immunoperoxidase technique as described (Johnson et al. (1990) Am. J. Pathol. 136:369-374). Primary antibodies were identical to those described previously (Burg et al. (1997) Lab. Invest. 76:505-516; Yoshimura et al. (1991) Kidney Int. 40:470-476) and included a murine monoclonal antibody (clone 1A4) to α-smooth muscle actin; a murine monoclonal antibody (clone PGF-007) to PDGF B-chain; a murine monoclonal IgG antibody (clone ED1) to a cytoplasmic antigen present in monocytes, macrophages and dendritic cells; affinity purified polyclonal goat anti-human/bovine type IV collagen IgG preabsorbed with rat erythrocytes; an affinity purified IgG fraction of a polyclonal rabbit anti-rat fibronectin antibody; plus appropriate negative controls as described previously (Burg et al. (1997) Lab. Invest. 76:505-516; Yoshimura et al. (1991) Kidney Int. 40:470-476). Evaluation of all slides was performed by an observer, who was unaware of the origin of the slides.

To obtain mean numbers of infiltrating leukocytes in glomeruli, more than 50 consecutive cross sections of glomeruli containing more than 20 discrete capillary segments were evaluated and mean values per kidney were calculated. For the evaluation of the immunoperoxidase stains for α-smooth muscle actin, PDGF B-chain, type IV collagen and fibronectin each glomerular area was graded semiquantitatively, and the mean score per biopsy was calculated. Each score reflects mainly changes in the extent rather than intensity of staining and depends on the percentage of the glomerular tuft area showing focally enhanced positive staining: I=0-25%, II=25-50%, III=50-75%, IV=>75%. This semiquantitative scoring system is reproducible among different observers and the data are highly correlated with those obtained by computerized morphometry (Kliem et al. (1996) Kidney Int. 49:666-678; Hugo et al. (1996) J. Clin. Invest. 97:2499-2508).

Immunohistochemical Double-Staining

Double immunostaining for the identification of the type of proliferating cells was performed as reported previously (Kliem et al. (1996) Kidney Int. 49:666-678; Hugo et al. (1996) J. Clin. Invest. 97:2499-2508) by first staining the sections for proliferating cells with a murine monoclonal antibody (clone BU-1) against bromo-deoxyuridine containing nuclease in Tris buffered saline (Amersham, Braunschweig, Germany) using an indirect immunoperoxidase procedure. Sections were then incubated with the $IgG_1$ monoclonal antibodies 1A4 against α-smooth muscle actin and ED 1 against monocytes/macrophages. Cells were identified as proliferating mesangial cells or monocytes/macrophages if they showed positive nuclear staining for BrdU and if the nucleus was completely surrounded by cytoplasm positive for α-smooth muscle actin. Negative controls included omission of either of the primary antibodies in which case no double-staining was noted.

In Situ Hybridization for Type IV Collagen mRNA

In situ hybridization was performed on 4 mm sections of biopsy tissue fixed in buffered 10% formalin utilizing a digoxigenin-labelled anti-sense RNA probe for type IV collagen (Eitner et al. (1997) Kidney Int. 51:69-78) as described (Yoshimura et al. (1991) Kidney Int. 40:470-476). Detection of the RNA probe was performed with an alkaline phosphatase coupled anti-digoxigenin antibody (Genius Nonradioactive Nucleic Acid Detection Kit, Boehringer-Mannheim, Mannheim, Germany) with subsequent color development. Controls consisted of hybridization with a sense probe to matched serial sections, by hybridization of the anti-sense probe to tissue sections which had been incubated with RNAse A before hybridization, or by deletion of the probe, antibody or color solution described (Yoshimura et al. (1991) Kidney Int. 40:470-476). Glomerular mRNA expression was semiquantitatively assessed using the scoring system described above.

Miscellaneous Measurements

Urinary protein was measured using the Bio-Rad Protein Assay (Bio-Rad Laboratories GmbH, München, Germany) and bovine serum albumin (Sigma) as a standard.

Statistical Analysis

All values are expressed as means±SD. Statistical significance (defined as $p<0.05$) was evaluated using ANOVA and Bonferroni t-tests.

EXAMPLE 9

For all experiments reported here, the modified DNA Nucleic Acid Ligand was conjugated to 40K PEG as described in Examples 5 and 8 and shown in FIGS. 9A and 9B. Since most Nucleic Acid Ligands have molecular weights ranging between 8 to 12 kDa (the modified PDGF Nucleic Acid Ligand has MW of 10 kDa), the addition of a large inert molecular entity such as PEG dramatically improves the residence times of Nucleic Acid Ligands in vivo (see for example PCT/US 97/18944). Importantly, the addition of the PEG moiety to the 5' end of the Nucleic Acid Ligand has no effect on the binding affinity of the Nucleic Acid Ligand for PDGF-BB ($K_d\#1\times10^{-10}$ M).

Cross-Reactivity of Nucleic Acid Ligands for Rat PDGF-BB

The sequence of PDGF is highly conserved among species, and human and rat PDGF B-chain sequences are 89% identical (Herren et al. (1993) Biochim. Biophys. Acta 1173:294; Lindner et al. (1995) Circ. Res. 76.951). Nevertheless, in view of the high specificity of Nucleic Acid Ligands (Gold et al. (1995) Ann. Rev. Biochem. 64:763-797), the correct interpretation of the in vivo experiments requires understanding of the binding properties of the Nucleic Acid Ligands to rat PDGF B-chain. We have therefore cloned and expressed the mature form of rat PDGF-BB in E. coli. The PDGF Nucleic Acid Ligands bound to rat and human recombinant PDGF-BB with the same high affinity (data not shown).

Figure 12:
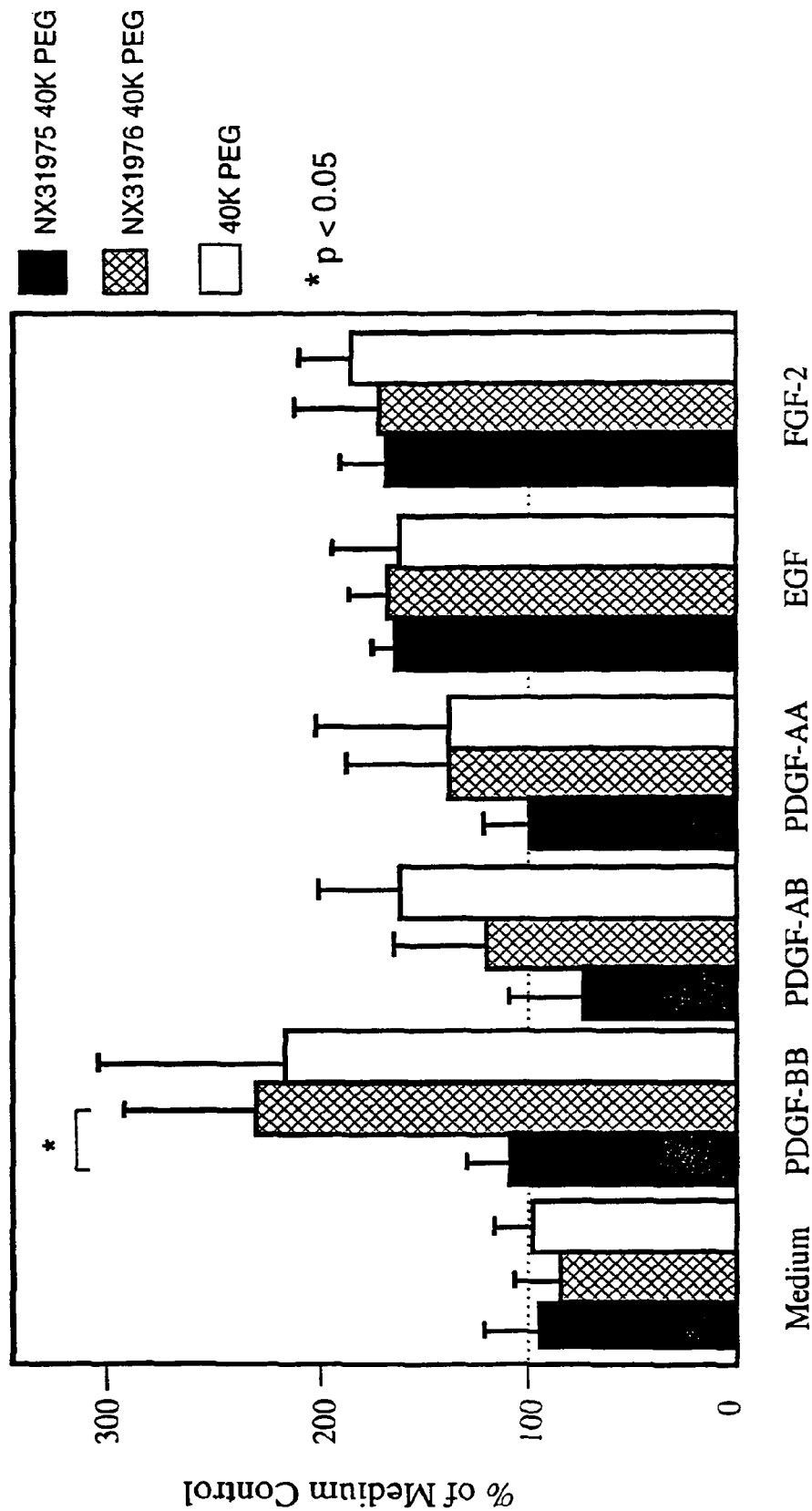
FIG. 12 shows the effects of NX31975 40K PEG on mitogen-stimulated proliferation of mesangial cells in culture (all mitogens were added at 100 ng/ml final concentration). Scrambled Nucleic Acid Ligand NX31976 and 40K PEG were also tested. Data are optical densities measured in the XTT assay and are expressed as percentages of baseline, i.e., cells stimulated with medium plus 200 μg/ml 40K PEG (i.e., the amount equivalent to the PEG attached to 50 μg/ml Nucleic Acid Ligand). Results are means±SD of 5 separate experiments (n=3 in the case of medium plus 40K PEG; statistical evaluation was therefore confined to NX31975 and scrambled Nucleic Acid Ligand groups).

PDGF B-Chain DNA-Ligand Specifically Inhibits Mesangial Cell Proliferation In Vitro In growth arrested mesangial cells, the effects of NX31975 40K PEG or the scrambled Nucleic Acid Ligand (NX31976 40K PEG) on growth factor induced proliferation were tested. Stimulated growth rates of the cells were not affected by the addition of scrambled Nucleic Acid Ligand (FIG. 12). Fifty μg/ml of NX31975 40K PEG significantly reduced PDGF-BB induced mesangial cell growth (FIG. 12). PDGF-AB and -AA induced mesangial cell growth also tended to be lower with NX31975 40K PEG, but these differences failed to reach statistical significance (FIG. 12). In contrast, no effects of NX31975 40K PEG on either EGF or FGF-2 induced growth were noted. Similar effects were noted if the Nucleic Acid Ligands were used at a concentration of 10 μg/ml (data not shown).

Effects of PDGF B-Chain DNA-Ligand in Rats with Anti-Thy 1.1 Nephritis

Following the injection of anti-Thy 1.1 antibody, PBS treated animals developed the typical course of the nephritis, which is characterized by early mesangiolysis and followed by a phase of mesangial cell proliferation and matrix accumulation on days 6 and 9 (Floege et al. (1993) Kidney Int. Suppl. 39:S47-54). No obvious adverse effects were noted following the repeated injection of Nucleic Acid Ligands or PEG alone, and all rats survived and appeared normal until the end of the study.

In PAS stained renal sections the mesangioproliferative changes on days 6 and 9 after disease induction were severe and indistinguishable among rats receiving PBS, PEG alone or the scrambled Nucleic Acid Ligand (data not shown). Histological changes were markedly reduced and almost normalized in the NX31975 40K PEG ligand treated group In order to (semi-)quantitatively evaluate the mesangioproliferative changes, various parameters were analyzed:

a) Reduction of Mesangial Cell Proliferation

Figure 13A:
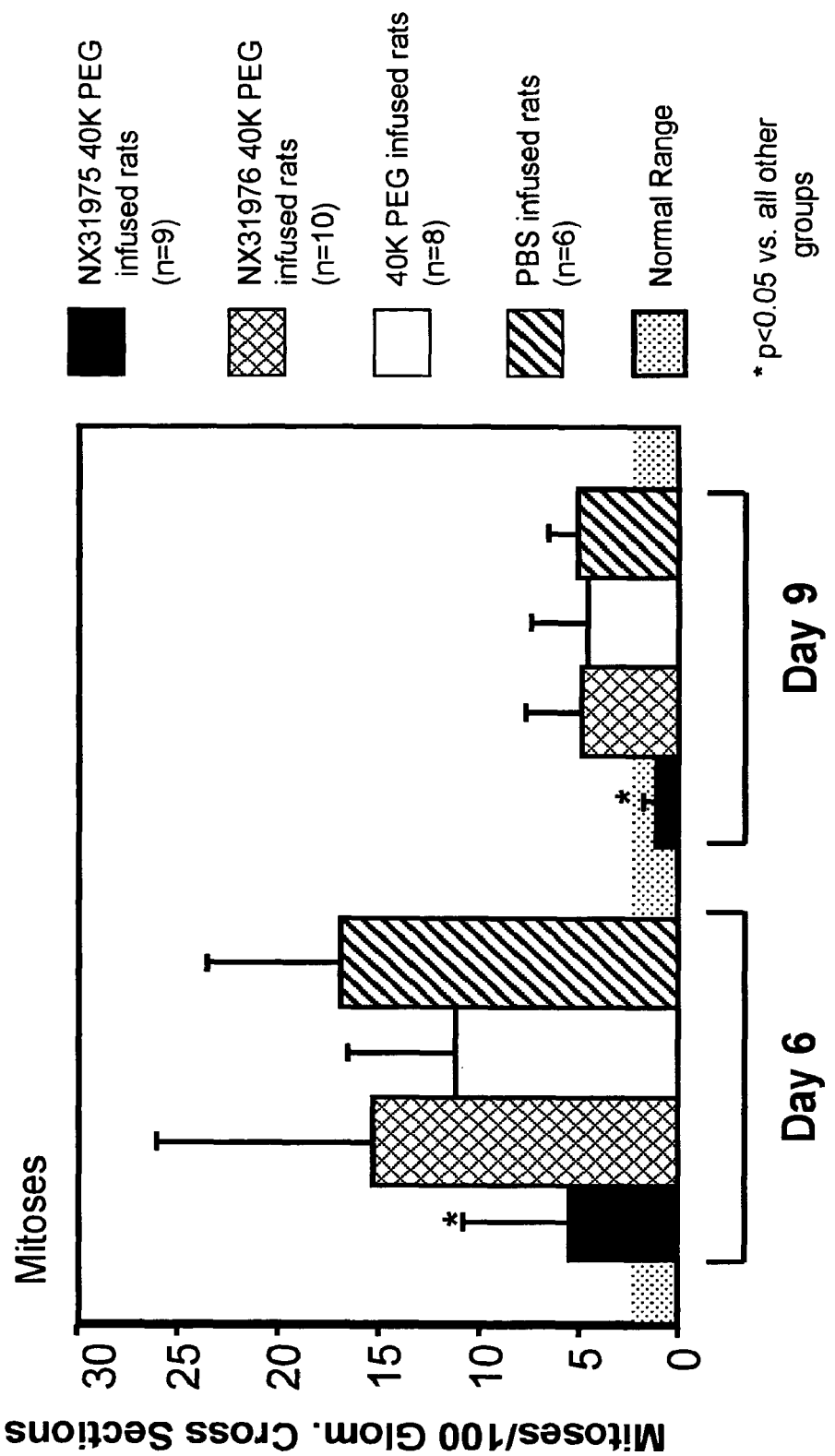
FIGS. 13A-13E show effects of NX31975 40K PEG on glomerular cell proliferation (FIG. 13A), expression of glomerular PDGF B-chain (FIG. 13B), proteinuria in rats with anti-Thy 1.1 nephritis (FIG. 13C), mesangial cell activation (as assessed by glomerular de novo expression of α-smooth muscle actin) (FIG. 13D), and monocyte/macrophage influx (FIG. 13E). NX31975 40K PEG is shown as black, NX31976 40K PEG is shown as cross-hatched, 40K PEG is shown as white, PBS is shown as hatched, and the normal range is shown as stippled.
Figure 13B:
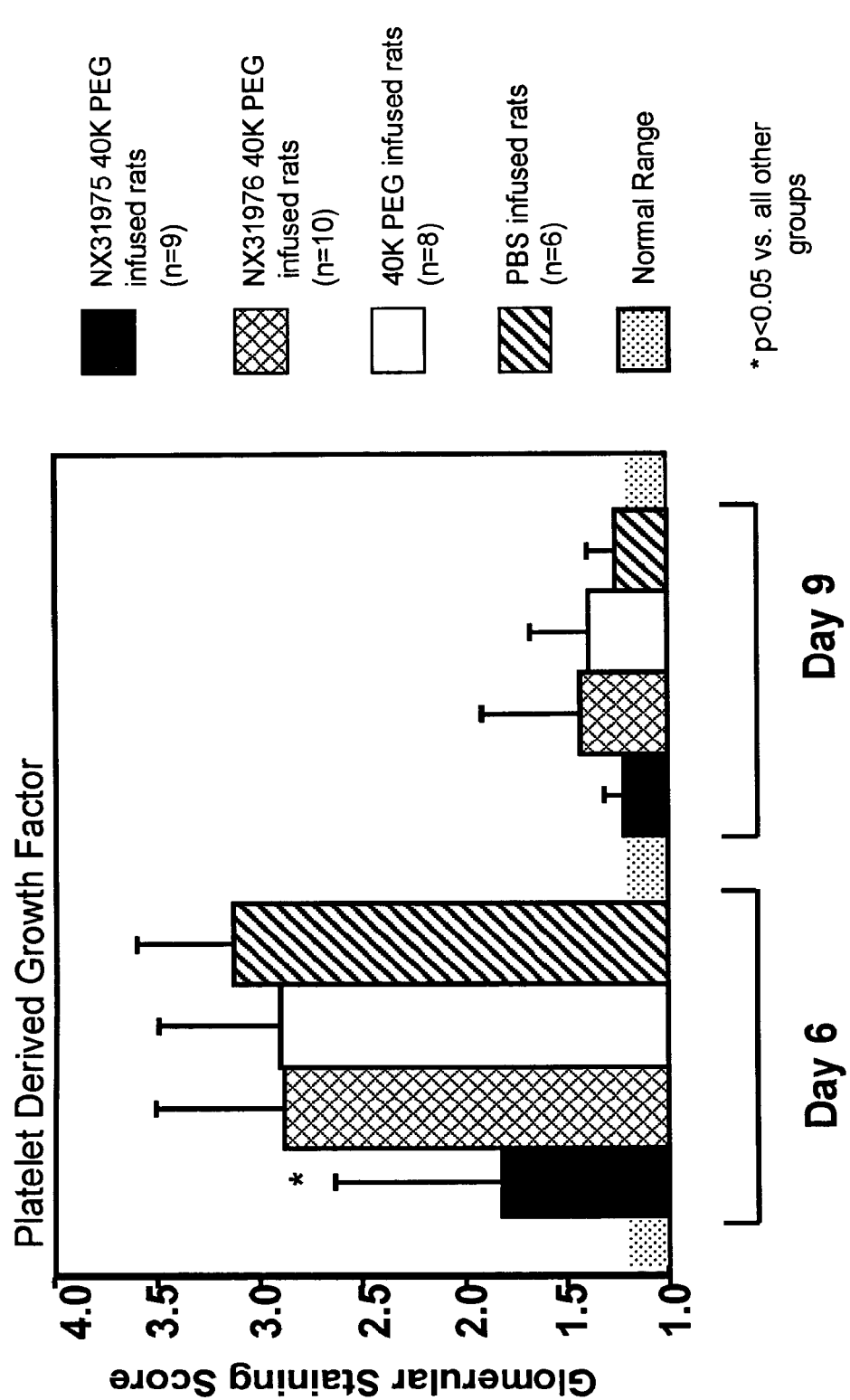

Glomerular cell proliferation, as assessed by counting the number of glomerular mitoses, was not significantly different between the three control groups on days 6 and 9 (FIG. 13A). As compared to rats receiving the scrambled Nucleic Acid Ligand, treatment with PDGF-B ligand led to a reduction of glomerular mitoses by 64% on day 6 and by 78% on day 9 (FIG. 13A). To assess the treatment effects on mesangial cells, the renal sections for α-smooth muscle actin were immunostained, which is expressed by activated mesangial cells only (Johnson et al. (1991) J. Clin. Invest. 87:847-858). Again, there were no significant differences between the three control groups on days 6 and 9. However, the immunostaining scores of α-smooth muscle actin were significantly reduced on day 6 and 9 in the NX31975 40K PEG treated group (FIG. 13D). To specifically determine whether mesangial cell proliferation was reduced, NX31975 40K PEG treated rats and scrambled Nucleic Acid Ligand treated rats were double immunostained for a cell proliferation marker (BrdU) and α-smooth muscle actin. The data confirmed a marked decrease of proliferating mesangial cells on day 9 after disease induction: 2.2±0.8 BrdU-/α-smooth muscle actin positive cells per glomerular cross section in PDGF-B aptamer treated rats versus 43.3±12.4 cells in rats receiving the scrambled Nucleic Acid Ligand, i.e., a 95% reduction of mesangial cell proliferation. In contrast, no effect of the PDGF-B aptamer was noted on proliferating monocytes/macrophages on day 9 after disease induction (PDGF-B aptamer treated rates: 2.8±1.1 BrdU+/ED-1+ cells per 100 glomerular cross sections; scrambled aptamer treated rats: 2.7±1.8).

b) Reduced Expression of Endogenous PDGF B-Chain

By immunohistochemistry, the glomerular PDGF B-chain expression was markedly upregulated in all three control groups (FIG. 13B), similar to previous observations (Yoshimura et al. (1991) Kidney Int. 40:470-476). In the NX31975 40K PEG treated group the glomerular overexpression of PDGF B-chain was significantly reduced in parallel with the reduction of proliferating mesangial cells (FIG. 13B).

c) Reduction of Glomerular Monocyte/Macrophage Influx

Figure 13C:
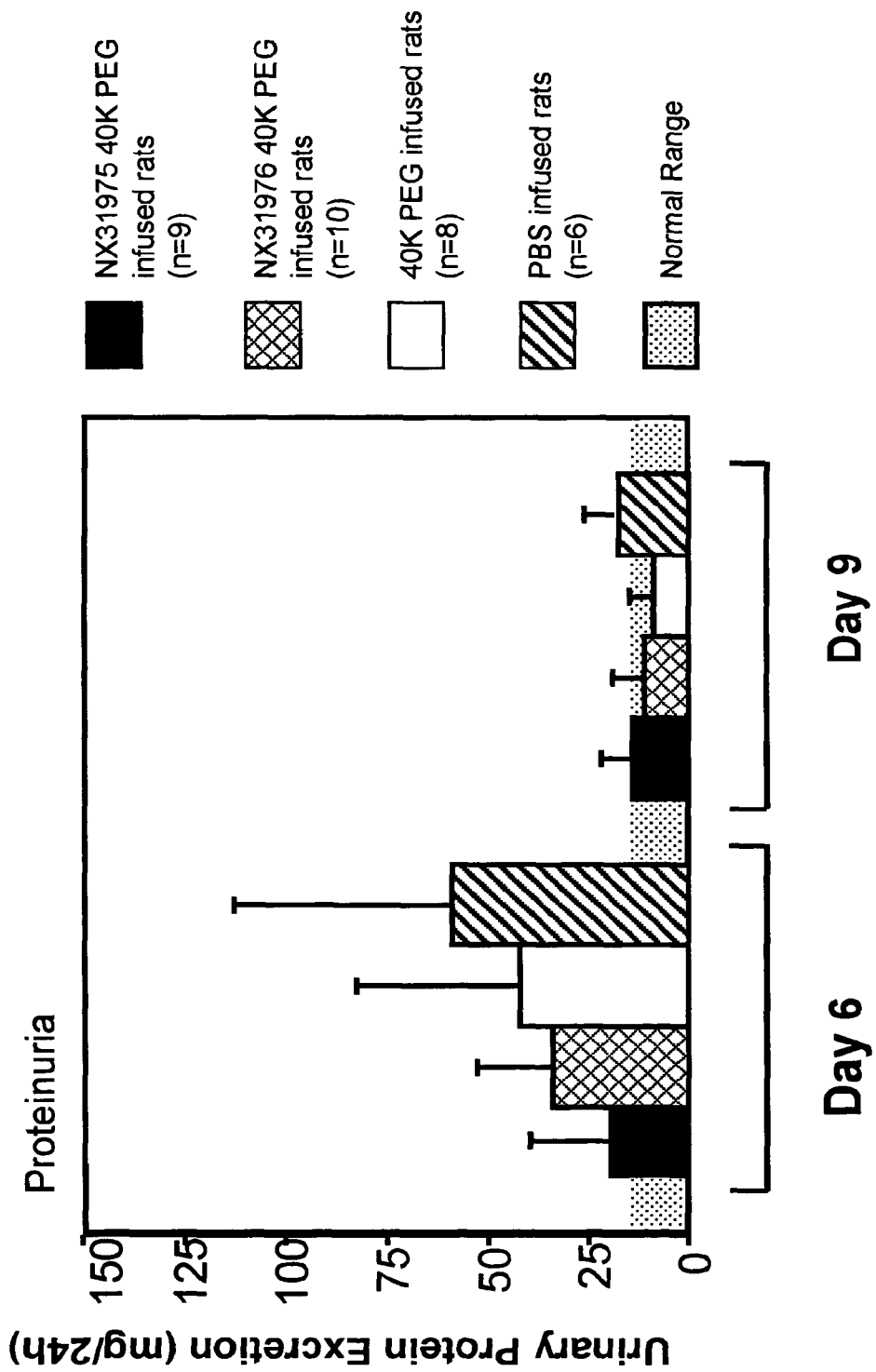
Figure 13D:
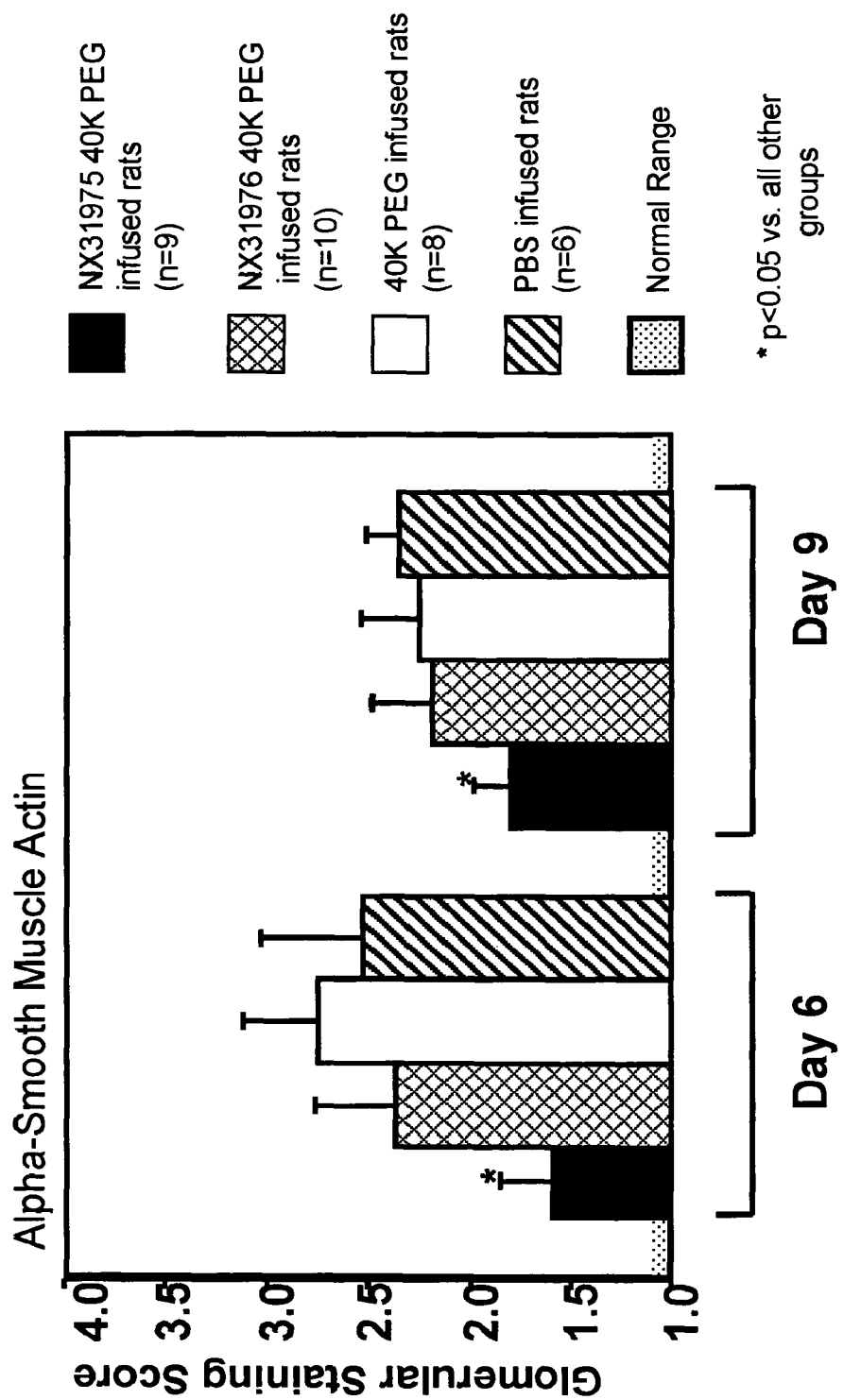
Figure 13E:
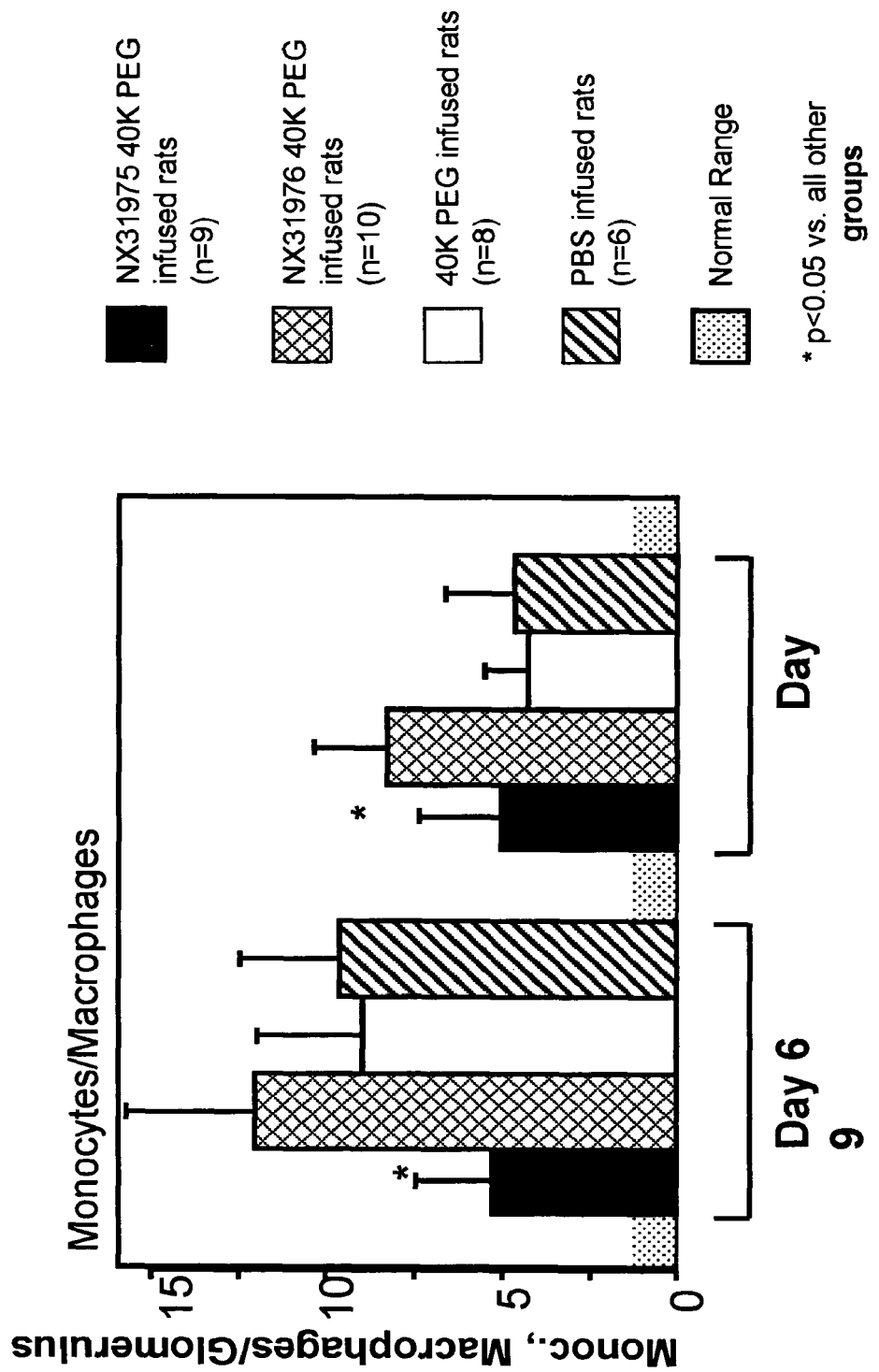

The glomerular monocyte/macrophage influx was significantly reduced in the NX31975 40K PEG treated rats as compared to rats receiving scrambled Nucleic Acid Ligand on days 6 and 9 after disease induction (FIG. 13E).

d) Effects on Proteinuria

Moderate proteinuria of up to 147 mg/24 hrs was present on day 6 after disease induction in the 3 control groups (FIG. 13C). Treatment with NX31975 40K PEG reduced the mean proteinuria on day 6, but this failed to reach statistical significance (FIG. 13C). Proteinuria on day 9 after disease induction was low and similar in all four groups (FIG. 13C).

e) Reduction of Glomerular Matrix Production and Accumulation

Figure 14A:
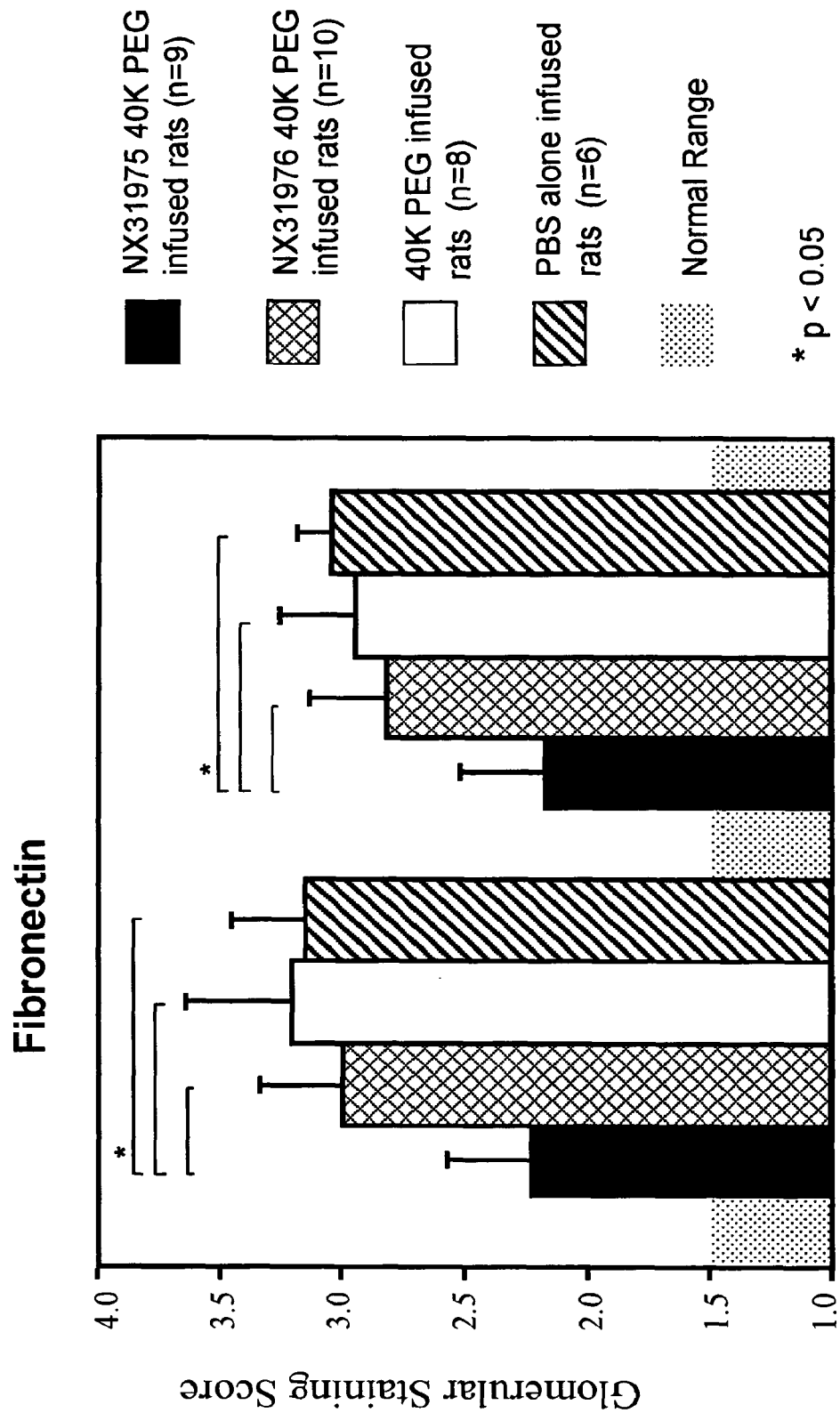
FIG. 14A-C show the effects of NX31975 40K PEG on glomerular matrix accumulation. Glomerular immunostaining scores for fibronectin and type IV collagen as well as glomerular scores for type IV collagen mRNA expression (in situ hydridization) are shown. NX31975 40K PEG is shown as black, NX31976 40K PEG is shown as cross-hatched, 40K PEG is shown as white, PBS is shown as hatched, and the normal range is shown as stippled.
Figure 14B:
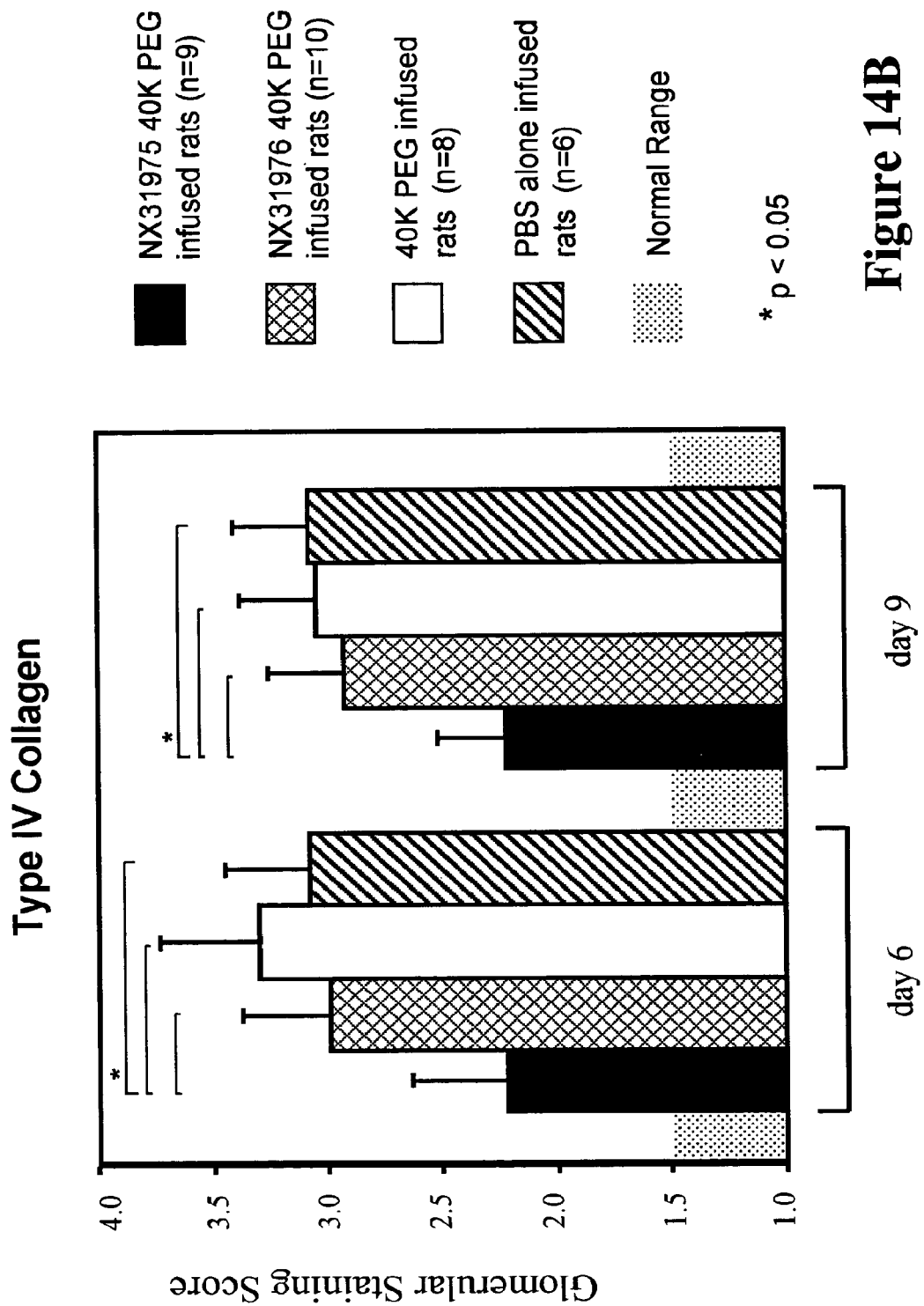
Figure 14C:
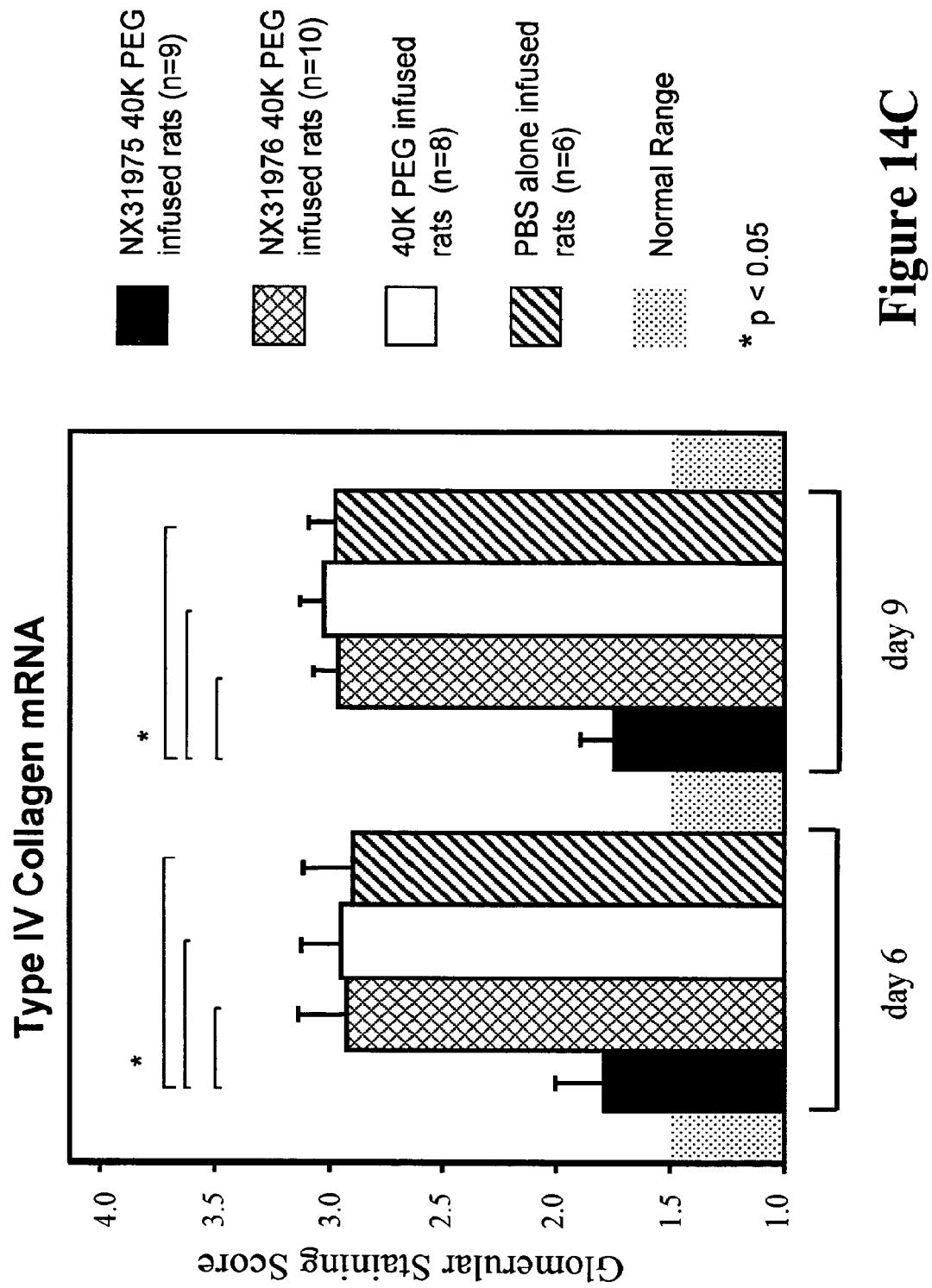

By immunohistochemistry, marked glomerular accumulation of type IV collagen and fibronectin was noted in all three control groups (FIG. 14). The overexpression of both glomerular type IV collagen and fibronectin was significantly reduced NX31975 40K PEG treated rats (FIG. 14). In the latter, glomerular staining scores approached those observed in normal rats (FIG. 14). By in situ hybridization, the decreased glomerular expression of type IV collagen in NX31975 40K PEG treated rats was shown to be associated with decreased glomerular synthesis of this collagen type (FIG. 14).

EXAMPLE 10

Experimental Procedure for Evolving 2'-Fluoro-2'-Deoxypyrimidine RNA Ligands to PDGF and RNA Sequences Obtained 2'-Fluoro-2'-Deoxypyrimidine RNA SELEX SELEX with 2'-fluoro-2'-deoxypyrimidine RNA targeting PDGF AB was done essentially as described previously (vide supra, and Jellinek et al., 1993, 1994: supra) using the primer template set as shown in Table 8 (SEQ ID NOS: 36-38). Briefly, the 2'-fluoro-2'-deoxypyrimidine RNA for affinity selections was prepared by in vitro transcription from synthetic DNA templates using T7 RNA polymerase (Milligan et al. (1987) Nucl. Acids Res. 15:8783). The conditions for in vitro transcription described in detail previously (Jellinek et al. (1994) supra) were used, except that higher concentration (3 mM) of the 2'-fluoro-2'-deoxypyrimidine nucleoside triphosphates (2'-F-UTP and 2'-F-CTP) was used compared to ATP and GTP (1 mM). Affinity selections were done by incubating PDGF AB with 2'-fluoro-2'-deoxypyrimidine RNA for at least 15 min at 37° C. in PBS containing 0.01% human serum albumin. Partitioning of free RNA from protein-bound RNA was done by nitrocellulose filtration as described (Jellinek et al., 1993, 1994: supra). Reverse transcription of the affinity-selected RNA and amplification by PCR were done as described previously (Jellinek et al. (1994) supra). Nineteen rounds of SELEX were performed, typically selecting between 1-12% of the input RNA. For the first eight rounds of selection, suramin (3-15 µM) was included in the selection buffer to increase the selection pressure. The affinity-enriched pool (round 19) was cloned and sequenced as described (Schneider et al. (1992) supra). Forty-six unique sequences have been identified, and the sequences are shown in Table 9 (SEQ ID NOS: 39-81). The unique-sequence ligands were screened for their ability to bind PDGF AB with high affinity. While random 2'-fluoropyrimidine RNA (Table 8) bound to PDGF with a dissociation constant (Kd) of 35±7 nM, many of the affinity-selected ligands bound to PDGF AB with ~100-fold higher affinities. Among the unique ligands, clones 9 ($K_d$=91±16 pM), 11 ($K_d$=120±21 pM), 16 (K=116±34 pM), 23 ($K_d$=173±38 pM), 25 ($K_d$=80±22 pM), 37 ($K_d$=97±29 pM) 38 ($K_d$=74±39 pM), and 40 ($K_d$=91±32 pM) exhibited the highest affinity for PDGF AB (binding of all of these ligands to PDGF AB is biphasic and the $K_d$ for the higher affinity binding component is given).

TABLE 1

Starting DNA and PCR primers for the ssDNA SELEX experiment.

| | SEQ ID NO. |
|---|---|
| Starting ssDNA:<br>5'-ATCCGCCTGATTAGCGATACT[-40N-]ACTTGAGCAAAATCACCTGCAGGGG-3' | 1 |
| PCR Primer 3N2*:<br>5'-BBBCCCCTGCAGGTGATTTTGCTCAAGT-3' | 2 |
| PCR Primer 5N2**:<br>5'-CCGAAGCTTAATACGACTCACTATAGGG<u>ATCCGCCTGATTAGCGATACT</u>-3' | 3 |

*B = biotin phosphoramidite (e.g., Glen Research, Sterling, VA)
**For rounds 10, 11, and 12, the truncated PCR primer 5N2 (underlined) was used to amplify the template.

TABLE 2

Unique Sequences of the ssDNA high affinity ligands to PDGF.
5'-ATCCGCCTGATTAGCGATACT [40N] ACTTGAGCAAAATCACCTGCAGGGG-3'

| | | SEQ ID NO |
|---|---|---|
| *14 | AGGCTTGACAAAGGGCACCATGGCTTAGTGGTCCTAGT | 4 |
| *41 | CAGGGCACTGCAAGCAATTGTGGTCCCAATGGGCTGAGT | 5 |
| 6 | CCAGGCAGTCATGGTCATTGTTTACAGTCGTGGAGTAGGT | 6 |
| 23 | AGGTGATCCCTGCAAAGGCAGGATAACGTCCTGAGCATC | 7 |
| 2 | ATGTGATCCCTGCAGAGGGAGGANACGTCTGAGCATC | 8 |
| 34 | CACGTGATCCCATAAGGGCTGCGCAAAATAGCAGAGCATC | 9 |
| 8 | GGTGGACTAGAGGGCAGCAAACGATCCTTGGTTAGCGTCC | 10 |
| 1 | GGTGCGACGAGGCTTACACAAACGTACACGTTTCCCCGC | 11 |
| 5 | TGTCGGAGCAGGGGCGTACGAAAACTTTACAGTTCCCCCG | 12 |
| *40 | AGTGGAACAGGGCACGGAGAGTCAAACTTTGGTTTCCCCC | 13 |
| 47 | GTGGGTAGGGATCGGTGGATGCCTCGTCACTTCTAGTCCC | 14 |
| 18 | GGGCGCCCTAAACAAAGGGTGGTCACTTCTAGTCCCAGGA | 15 |
| 30 | TCCGGGCTCGGGATTCGTGGTCACTTTCAGTCCCGGATATA | 16 |
| *20 | ATGGGAGGGCGCGTTCTTCGTGGTTACTTTTAGTCCCG | 17 |
| 35 | ACGGGAGGGCACGTTCTTCGTGGTTACTTTTAGTCCCG | 18 |
| 13 | GCTCGTAGGGGCGATTCTTTCGCCGTTACTTCCAGTCCT | 19 |
| 16 | GAGGCATGTTAACATGAGCATCGTCTCACGATCCTCAGCC | 20 |
| *36 | CCACAGGCTACGGCACGTAGAGCATCACCATGATCCTGTG | 21 |
| 50 | GCGGGCATGGCACATGAGCATCTCTGATCCCGCAATCCTC | 22 |
| 4 | ACCGGGCTACTTCGTAGAGCATCTCTGATCCCGGTGCTCG | 23 |
| 44 | AAAGGGCGAACGTAGGTCGAGGCATCCATTGGATCCCTTC | 24 |
| 24 | ACGGGCTCTGTCACTGTGGCACTAGCAATAGTCCCGTCGC | 25 |
| 7 | GGGCAGACCTTCTGGACGAGCATCACCTATGTGATCCCG | 26 |
| *26 | AGAGGGGAAGTAGGCTGCCTGACTCGAGAGAGTCCTCCCG | 27 |
| 19 | AGGGGTGCGAAACACATAATCCTCGCGGATTCCCATCGCT | 28 |
| 48 | GGGGGGGCAATGGCGGTACCTCTGGTCCCCTAAATAC | 29 |
| 46 | GCGGCTCAAAGTCCTGCTACCCGCAGCACATCTGTGGTC | 30 |
| 25 | TTGGGCGTGAATGTCCACGGGTACCTCCGGTCCCAAAGAG | 31 |
| 31 | TCCGCGCAAGTCCCTGGTAAAGGGCAGCCCTAACTGGTC | 32 |
| 12 | CAAGTTCCCCACAAGACTGGGGCTGTTCAAACCGCTAGTA | 33 |
| 15 | CAAGTAGGGCGCGACACACGTCCGGGCACCTAAGGTCCCA | 34 |
| *38 | AAAGTCGTGCAGGGTCCCCTGGAAGCATCTCCGATCCCAG | 35 |

*Indicates a boundary experiment was performed.
Italics indicate the clones that were found to retain high affinity binding as minimal ligands.

TABLE 3

```
                                    HELIX I
                         HELIX II         HELIX III
SEQ ID NO:  Group A
    8         2                =AGGG---AGGA--TACG------TCTG-AGC-ATCac3'  5'ATGTGAT-CCCTGCAG=
   23         4            ACCGGG---CTAC--TTC-------GTAG-AGC-ATC----TCT-----GAT-CCCGGTGCTCG
   26         7             tGGG---CGACC-TTCT-----GGACG-AGC-ATCAC--CTAT--GTGAT-CCCG
   20        16            ctGAGG---CATG--TTAA------CATG-AGC-ATCGT--CTC---ACGAT-CCTCAGCC
   21        36            CCACAGG---CTACG-GCA------CGTAG-AGC-ATCA---CCA----TGAT-CCTGTG
   35        38     AAAGTCGTGCAGGG---TCC---CCT--------GGA-AGC-ATC----TCC-----GAT-CCCAGactt
   24        44            AAAGGG---CGAAC-GTA------GGTCG-AGGCATCC---ATT----GGAT-CCCTTC
   22        50             GCGGG---CATG--GCA------CATG-AGC-ATC----TCT-----GAT-CCCGCAATCCTC
    7        23                =AGG---CAGGATAAC-----GTCCTG-AGC-ATCac3'  5'AGGTGATCCCTGCAA=
    9        34                =GGG---CTGC--GCAAAATA--GCAG-AGC-ATCac3'  5'CACGTGAT-CCCATAA=

SEQ ID NO:  Group B
   19        13            GCTCGTAGG---GGGCGA-TTCTT----TCGCC-GTT-ACT----TCC-----AGT-CCTac
    4        14             tactAGG---CTT--GACA--------AAG-GGC-ACCAT--GGCTTAGTGGT-CCTAGTa
   34        15         ctCAAGTAGGG---CGGAC-ACAC-----GTCCG-GGC-ACC----TAA----GGT-CCCAacttgag
   15        18              ctGGG---CGCCCTAAACAA--AGGGTG-GTC-ACT----TCT-----AGT-CCCAGGA
   17        20            ATGGGAGGG---CGCG--TTCTT-----CGTG-GTT-ACT----TTT-----AGT-CCCG
   31        25              ctTTGGG---CGTG--AATGTC----CACG-GGT-ACC----TCC-----GGT-CCCAAAGAG
   16        30              TCCGGG---CTCGG-GAT-------TCGTG-GTC-ACT----TTC-----AGT-CCCGGATATA
   32        31                                          5'TCCGCGCAAGT-CCCTGGTAA=
                              =AGGG---CAG---CCCTAA-----CTG-GTC-acttgagc3'
   18        35            ACGGGAGGG---CACG--TTCTT-----CGTG-GTT-ACT----TTT-----AGT-CCCG
    5        41                =GGG---CTGAGTa3'   5'tactCAG-GGC-ACTGCAAGCAATTGTGGT-CCCAAT=
   14        47            GTGGGTGGGATCGGGG--ATG-------CCTC-GTC-ACT----TCT-----AGT-CCCact
```

TABLE 4

Frequency of base pairs in the helical regions of the consensus motif shown in FIG. 1.

| Position[a] | Base pair[b] | | | | | | |
|---|---|---|---|---|---|---|---|
| | AT | TA | GC | CG | TG | GT | other |
| I-1 | 0 | 0 | 21 | 0 | 0 | 0 | 0 |
| I-2 | 0 | 0 | 21 | 0 | 0 | 0 | 0 |
| I-3 | 5 | 0 | 16 | 0 | 0 | 0 | 0 |
| I-4 | 3 | 5 | 1 | 4 | 1 | 0 | 7 |
| I-5 | 2 | 3 | 3 | 4 | 0 | 0 | 9 |
| II-1 | 0 | 1 | 2 | 17 | 0 | 0 | 1 |
| II-2 | 5 | 5 | 5 | 1 | 0 | 4 | 1 |
| II-3 | 3 | 4 | 7 | 6 | 0 | 0 | 1 |
| II-4 | 3 | 0 | 8 | 5 | 0 | 0 | 4 |
| III-1 | 21 | 0 | 0 | 0 | 0 | 0 | 0 |
| III-2 | 0 | 10 | 0 | 11 | 0 | 0 | 0 |
| III-3 | 0 | 7 | 0 | 13 | 1 | 0 | 0 |

[a]Helices are numbered with roman numerals as shown in FIG. 1. Individual base pairs are numbered with Arabic numerals starting with position 1 at the helix junction and increasing with increased distance from the junction.
[b]The TG and GT base pairs to the Watson-Crick base pairs for this analysis were included. There is a total of 21 sequences in the set.

TABLE 5

Affinities of the minimal DNA ligands to PDGF AA, PDGF AB and PDGF BB.

| | $K_d$, nM | | |
|---|---|---|---|
| Ligand | PDGF AA[a] | PDGF AB[b] | PDGF BB[b] |
| 20t | 47 ± 4 | 0.147 ± 0.011 | 0.127 ± 0.031 |
| 36t | 72 ± 12 | 0.094 ± 0.011 | 0.093 ± 0.009 |
| 41t | 49 ± 8 | 0.138 ± 0.009 | 0.129 ± 0.011 |

[a]Data points shown in FIG. 3A were fitted to eq 1 (Example 1).
[b]Data points in FIGS. 3B and 3C were fitted to eq. 2. The dissociation constant ($K_d$) values shown are for the higher affinity binding component. The mole fraction of DNA that binds to PDGF AB or PDGF BB as the high affinity component ranges between 0.58 to 0.88. The $K_d$ values for the lower affinity interaction range between 13 to 78 nM.

TABLE 6

Relative affinity for PDGF-AB of ligand 36t variants.

| Ligand | SEQ ID NO | Composition* | $Kd^{ligand}/Kd^{36t}$** |
|---|---|---|---|
| 36t | 84 | CACAGGCTACGGCACGTAGAGCATCACCATGATCCTGTG[3'T] | 1.0 |
| 1073 | 97 | CACAGGCTACGGCACGTAGAGCATCACCATGATCCTGUG[3'T] | 11.8 |
| 1074 | 98 | CACAGGCTACGGCACGUAGAGCATCACCATGATCCTGTG[3'T] | 3.1 |
| 1075 | 99 | CACAGGCTACGGCACGTAGAGCATCACCAUGATCCTGTG[3'T] | 10 |
| 1076 | 100 | CACAGGCTACGGCACGUAGAGCATCACCAUGATCCTGTG[3'T] | 440 |
| 1145 | 101 | CACAGGCTACGGCACGTAGAGCATCACCATGATCCTGTG[3'T] | 0.27 |
| 1148 | 102 | CACAGGCUACGGCACGTAGAGCATCACCATGATCCTGTG[3'T] | 281 |
| 1144 | 103 | CACAGGCTACGGCACGTAGAGCATCACCATGAUCCUGTG[3'T] | 994 |
| 1142 | 104 | CACAGGCTACGGCACGUAGAGCAUCACCATGATCCTGTG[3'T] | 12.9 |
| 1149 | 105 | CACAGGCTACGGCACGTAGAGCATCACCATGATCCTGTG[3'T] | 2.9 |
| EV1 | 106 | CACAGGCTACGGCACGTAGAGCATCACCATGATCCTGTG[3'T] | 35.1 |
| EV2 | 107 | CACAGGCTACGGCACGUAGAGCATCACCATGATCCTGTG[3'T] | 5.3 |
| EV3 | 108 | CACAGGCTACGGCACGTAGAGCATCACCATGATCCTGTG[3'T] | 1.5 |
| EV4 | 109 | CACAGGCTACGGCACGTAGAGCATCACCATGATCCTGTG[3'T] | 4.5 |
| EV5 | 110 | CACAGGCTACGGCACGTAGAGCATCACCATGATCCUGUG[3'T] | 2.3 |
| 1157 | 111 | CACAGGCTACGGCACGTAGAGCATCACCATGATCCTGTG[3'T] | 1.0 |
| 1160 | 112 | CACAGGCTACGGCACGTAGAGCATCACCATGATCCTGTG[3'T] | 1.4 |
| 1161 | 113 | CACAGGCTACGGCACGTAGAGCATCACCATGATCCTGTG[3'T] | 0.22 |

TABLE 6-continued

Relative affinity for PDGF-AB of ligand 36t variants.

| Ligand | SEQ ID NO | Composition* | Kd$^{ligand}$/Kd$^{36t}$** |
|---|---|---|---|
| 1162 | 114 | CACAGGCTACGGCACGTAGAGCATCACCATGAT*C*CTGTG[³'T] | 0.52 |
| 1165 | 115 | CACAGGCTACGGCACGTAGAGCATCACCATGATC*C*TGTG[³'T] | 0.61 |
| 1164 | 116 | CACAGGC*U*ACGGCACGTAGAGCATCACCATGATCCTGTG[³'T] | 0.45 |
| 1166 | 117 | CACAGGCTACGGCACG*U*AGAGCATCACCATGATCCTGTG[³'T] | 0.76 |
| 1159 | 118 | CACAGGCTACGGCACGTAGAGCA*U*CACCATGATCCTGTG[³'T] | 0.37 |
| 1163 | 119 | CACAGGCTACGGCACGTAGAGCATCACCA*U*GATCCTGTG[³'T] | 1.3 |
| 1158 | 120 | CACAGGCTACGGCACGTAGAGCATCACCATGA*U*CCTGTG[³'T] | 2.4 |
| 1255 | 121 | CACAGGC*U*ACGGCACG*U*AGAGC*AU*CACCATGA*UCCU*GTG[³'T] | 24.2 |
| 1257 | 122 | CACAGGCTACGGCACGTAGAGCATCACCATGATCCTGUG[³'T] | 1.3 |
| 1265 | 123 | CACAGGCTACGGCACGTAGAGCATCACCATGATCCUGUG[³'T] | 1.4 |
| 1266 | 124 | CACAGGC*U*ACGGCACGTAGAGCA*UC*ACCATGATCC*UGUG*[³'T] | 1.0 |
| 1267 | 125 | CACAGGCTACGGCACGTAGAGCATCACCATGATCC*U*GUG[³'T] | 4.2 |
| 1269 | 126 | CACAGGC*U*ACGGCACGTAGAGCATCACCATGATCC*U*GUG[³'T] | 0.87 |
| 1295 | 127 | CAGGC"ACGGCACGTAGAGCA*U*CACCATGATCC*U*GUG[³'T] | 0.9 |
| 1296 | 128 | CAGGC*U*-CGGCACG-AGAGCA*U*CACCATGATCC*U*GUG[³'T] | 2.1 |
| 1297 | 129 | CAGGC*U*-CGGCACG-AGAGCA*UC*-CCA-GAT*CC*UG[³'T] | 2.9 |
| 1303 | 130 | CAGGCUACGGCACGTAGAGCAUCACCATGATCCUG[³'T] | 5.8 |
| 1304 | 131 | CAGGCUACGGCACGTAGAGCAUCACCATGATCCUG[³'T] | 607 |
| 1305 | 132 | CAGGCUACGGCACGTAGAGCAUCACCATGATCCUG[³'T] | 196 |
| 1306 | 133 | CAGGCUACGGCACGTAGAGCAUCACCATGATCCUG[³'T] | 4.4 |
| 1327 | 134 | CAGGC*U*ACGGCACGTAGAGCAU*C*ACCATGAT*CC*UG[³'T] | 0.63 |
| 1328 | 135 | CAGGC*U*ACGGCACGTAGAGCAU*C*ACCATGAT*CC*UG[³'T] | 2.2 |
| 1329 | 136 | CAGGC*U*ACGGCACGTAGAGCAU*C*ACCATGAT*CC*UG[³'T] | 0.72 |
| 1369 | 137 | CAGGC*U*ACGGCACGTAGAGCAU*C*ACCATGAT*CC*UG[³'T] | 0.37 |
| 1374 | 138 | CAGGC*U*ACGGCACGTAGAGCAU*C*ACCATGAT*CC*UG[³'T] | 1.5 |
| 1358 | 139 | CAGGC*U*ACG-S-CGTAGAGCAU*C*A-S-TGAT*CC*UG[³'T] | 0.54 |
| 1441 | 140 | CAGGC*U*ACG-S-CGTAGAGCAU*C*A-S-TGAT*CC*UG[³'T] | 0.33 |

*A, C, G, T = deoxy-A,C,G,T; A, C, G, U = 2'-OMe-A,C,G,U; *C*, *U* = 2'-fluoro-C,U; S = hexa-ethyleneglycol spacer; [3'T] = inverted (3'-3') T.
**Kd$^{36t}$ value of 0.178 ± 88 pM used for the calculation is average, with standard deviation, of four independent measurements (94 ± 11, 16 ± 24, 155 ± 30 and 302 ± 32 pM).

TABLE 7

Relative affinity for PDGF-BB of ligand 36ta variants.
The effect of various substitutions on the affinity of ligand 36ta for PDGF-BB.

| Ligand | Composition* | Kd$^{ligand}$/Kd$^{36ta}$** | SEQ. ID NO. |
|---|---|---|---|
| 36ta | CAGGCTACGGCACGTAGAGCATCACCATGATCCTG[³'T] | 1.0 | 141 |
| NX21568 | CAGGC*U*ACG-S-CGTAGAGCAU*C*A-S-TGAT*CC*UG[³'T] | 0.63 | 142 |
| NX21617 | [L1]CAGGC*U*ACG-S-CGTAGAGCAU*C*A-S-TGAT*CC*UG[³'T] | 0.54 | 143 |

TABLE 7-continued

Relative affinity for PDGF-BB of ligand 36ta variants.
The effect of various substitutions on the affinity of ligand 36ta for PDGF-BB.

| Ligand | Composition* | $Kd^{ligand}/Kd^{36ta}$** | SEQ. ID NO. |
|---|---|---|---|
| NX21618 | [L1]CAGGCUACG-S-CGTAGAGCAUCA-S-TGAUCCTG[3'T] | 418 | 144 |
| NX31975 | [L2] CAGGCUACG-S-CGTAGAGCAUCA-S-TGATCCUG[3'T] | 0.54 | 148 |
| NX31976 | [L2] CAGCGUACG-S-CGTACCGATUCA-S-TGAACUG[3'T] | | 149 |

*A, C, G, T = deoxy-A,C,G,T; A,G = 2'-OMe-A,G; *C*, *U* = 2'-F-C,U; S = hexaethyleneglycol spacer (from Spacer Phosphoramidite 18, Glen Research, Sterling, VA); [3'T] = inverted (3'-3') T; [L1] = dT amine (Glen Research, Sterling, VA); [L2] = pentyl amino linker.
**$Kd^{36ta}$ = 0.159 ± 13 pM.

TABLE 8

Starting RNA and PCR primers for the 2'-fluoropyrimidine RNA SELEX experiment.

| | SEQ ID NO |
|---|---|
| Starting 2'-fluoropyrimidine RNA:<br>Starting RNA:<br>5'-GGGAGACAAGAAUAACGCUCAA[-50 N-]UUCGACAGGAGGCUCACAACAGGC-3' | 36 |
| PCR Primer 1:<br>5'-TAATACGACTCACTATAGGGAGACAAGAATAACGCTCAA-3' | 37 |
| PCR Primer 2:<br>5'-GCCTGTTGTGAGCCTCCTGTCGAA-3' | 38 |

TABLE 9

Sequences of the evolved region of 2'-fluoropyrimidine RNA high affinity ligands to PDGF AB. Sequences of the fixed region (Table 8) are not shown.

| | | SEQ ID NO. |
|---|---|---|
| 1 | CGGUGGCAUUUCUUCACUUCCUUCUCGCUUUCUCGCGUUGGGCNCGA | 39 |
| 2 | CCAACCUUCUGUCGGCGUUGCUUUUUGGACGGCACUCAGGCUCCA | 40 |
| 3 | UCGAUCGGUUGUGUGCCGGACAGCCUUAACCAGGGCUGGGACCGAGGCC | 41 |
| 4 | CUGAGUAGGGGAGGAAGUUGAAUCAGUUGUGGCGCCUCUCAUUCGC | 42 |
| 5 | CAGCACUUUCGCUUUUCAUCAUUUUUUCUUUCCACUGUUGGGCGCGGAA | 43 |
| 6 | UCAGUGCUGGCGUCAUGUCUCGAUGGGGAUUUUUCUUCAGCACUUUGCCA | 44 |
| 7 | UCUACUUUCCAUUUCUCUUUUCUUCUCACGAGCGGGUUUCCAGUGAACCA | 45 |
| 8 | CGAUAGUGACUACGAUGACGAAGGCCGCGGGUUGGAUGCCCGCAUUGA | 46 |
| 10 | GUCGAUACUGGCGACUUGCUCCAUUGGCCGAUUAACGAUUCGGUCAG | 47 |
| 13 | GUGCAAACUUAACCCGGGAACCGCGCGUUUCGAUCGACUUUCCUUUCCA | 48 |
| 15 | AUUCCGCGUUCCGAUUAAUCCUGUGCUCGGAAAUCGGUAGCCAUAGUGCA | 49 |
| 16 | CGAACGAGGAGGGAGUGGCAAGGGAUGGUUGGAUAGGCUCUACGCUCA | 50 |
| 17 | GCGAAACUGGCGACUUGCUCCAUUGGCCGAUAUAACGAUUCGGUUCAU | 51 |
| 18 | CGAACGAGGAGGGAGUCGCAAGGGAUGGUUGGAUAGGCUCUACGCUCAA | 52 |
| 19 | CGAGAAGUGACUACGAUGACGAAGGCCGCGGGUUGAAUCCCUCAUUGA | 53 |
| 20 | AAGCAACGAGACCUGACGCCUGAUGUGACUGUGCUUGCACCCGAUUCUG | 54 |

TABLE 9-continued Sequences of the evolved region of 2'-fluoropyrimidine
RNA high affinity ligands to PDGF AB. Sequences
of the fixed region (Table 8) are not shown.

| | | SEQ ID NO. |
|---|---|---|
| 21 | GUGAUUCUCAUUCUCAAUGCUUUCUCACAACUUUUUCCACUUCAGCGUGA | 55 |
| 22 | AAGCAACGAGACUCGACGCCUGAUGUGACUGUGCUUGCACCCGAUUCU | 56 |
| 23 | UCGAUCGGUUGUGUGCCGGACAGCUUUGACCAUGAGCUGGGACCGAGGCC | 57 |
| 24 | NGACGNGUGGACCUGACUAAUCGACUGAUCAAAGAUCCCGCCCAGAUGGG | 58 |
| 26 | CACUGCGACUUGCAGAAGCCUUGUGUGGCGGUACCCCCUUUGGCCUCG | 59 |
| 27 | GGUGGCAUUUCUUCAUUUUCCUUCUCGCUUUCUCCGCCGUUGGGCGCG | 60 |
| 29 | CCUGAGUAGGGGGGAAAGUUGAAUCAGUUGUGGCGCUCUACUCAUUCGCC | 61 |
| 30 | GUCGAAACUGGCGACUUGCUCCAUUGGCCGAUAUAACGAUUCGGUUCA | 62 |
| 31 | GCGAUACUGGCGACUUGCUCCAUUGGCCGAUAUAACGAUUCGGCUCAG | 63 |
| 32 | ACGUGGGGCACAGGACCGAGAGUCCCUCCGGCAAUAGCCGCUACCCCACC | 64 |
| 33 | CACAGCCUNANAGGGGGGAAGUUGAAUCAGUUGUGGCGCUCUACUCAUUCGC | 65 |
| 34 | ANGGGNUAUGGUGACUUGCUCCAUUGGCCGAUAUAACGAUUCGGUCAG | 66 |
| 35 | CCUGCGUAGGGNGGGAAGUUGAAUCAGUUGUGGCGCUCUACUCAUUCGCC | 67 |
| 39 | CGAACGAGGAGGGAGUGGCAAGGGAUGGUUGGAUAGGCUCUACGCUCA | 68 |
| 41 | GUGCAAACUUAACCCGGGAACCGCGCGUUUCGAUUCGCUUUCCNUAUUCCA | 69 |
| 42 | CGAACGAGGAGGGAGUGGCAAGGGACGGUNNAUAGGCUCUACGCUCA | 70 |
| 43 | UCGGUGUGGCUCAGAAACUGACACGCGUGAGCUUCGCACACAUCUGC | 71 |
| 44 | UAUCGCUUUUCAUCAAUUCCACUUUUUCACUCUNAACUUGGGCGUGCA | 72 |
| 45 | GUGCAAACUUAACCCGGGAACCGCGCGUUUCGAUCCUGCAUCCUUUUUCC | 73 |
| 46 | UCGNUCGGUUGUGUGCCGGCAGCUUUGUCCAGCGUUGGGCCGAGGCC | 74 |
| 47 | AGUACCCAUCUCAUCUUUUCCUUUCCUUUCUUCAAGGCACAUUGAGGGU | 75 |
| 49 | CCUGAGUAGGGGGGAAGUUGAACCAGUUGUGGCNGCCUACUCAUUCNCCA | 76 |
| 51 | CCNNCCUNCUGUCGGCGCUUGUCUUUUUGGACGGGCAACCCAGGGCUC | 77 |
| 52 | CCAACCUNCUGUCGGCGCUUGUCUUUUUGGACGAGCAACUCAAGGCUCGU | 78 |
| 53 | CCAGCGCAGAUCCCGGGCUGAAGUGACUGCCGGCAACGGCCGCUCCA | 79 |
| 54 | UUCCCGUAACAACUUUUCAUUUUCACUUUUCAUCCAACCAGUGAGCAGCA | 80 |
| 55 | UAUCGCUUUCAUCAAAUUCCACUCCUUCACUUCUUUAACUUGGGCGUGCA | 81 |

SEQUENCE LISTING (1) GENERAL INFORMATION:

(iii) NUMBER OF SEQUENCES: 149

(2) INFORMATION FOR SEQ ID NO: 1:

(i) SEQUENCE CHARACTERISTICS:
      (A) LENGTH: 86 base pairs
      (B) TYPE: nucleic acid
      (C) STRANDEDNESS: single (D) TOPOLOGY: linear (ii) MOLECULE TYPE: DNA (xi) SEQUENCE DESCRIPTION: SEQ ID NO: 1:

ATCCGCCTGA TTAGCGATAC TNNNNNNNNN NNNNNNNNNN NNNNNNNNNN          50

NNNNNNNNNN NACTTGAGCA AAATCACCTG CAGGGG                         86

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

CCCCTGCAGG TGATTTTGCT CAAGT                                     25

(2) INFORMATION FOR SEQ ID NO: 3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CCGAAGCTTA ATACGACTCA CTATAGGGAT CCGCCTGATT AGCGATACT           49

(2) INFORMATION FOR SEQ ID NO: 4:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ATCCGCCTGA TTAGCGATAC TAGGCTTGAC AAAGGGCACC ATGGCTTAGT          50

GGTCCTAGTA CTTGAGCAAA ATCACCTGCA GGGG                           84

(2) INFORMATION FOR SEQ ID NO: 5:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

ATCCGCCTGA TTAGCGATAC TCAGGGCACT GCAAGCAATT GTGGTCCCAA          50

TGGGCTGAGT ACTTGAGCAA AATCACCTGC AGGGG                          85

(2) INFORMATION FOR SEQ ID NO: 6:

(i) SEQUENCE CHARACTERISTICS:
        (A) LENGTH: 86 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO: 6:

ATCCGCCTGA TTAGCGATAC TCCAGGCAGT CATGGTCATT GTTTACAGTC        50

GTGGAGTAGG TACTTGAGCA AAATCACCTG CAGGGG                       86

(2) INFORMATION FOR SEQ ID NO: 7:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

ATCCGCCTGA TTAGCGATAC TAGGTGATCC CTGCAAAGGC AGGATAACGT        50

CCTGAGCATC ACTTGAGCAA AATCACCTGC AGGGG                        85

(2) INFORMATION FOR SEQ ID NO: 8:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ATCCGCCTGA TTAGCGATAC TATGTGATCC CTGCAGAGGG AGGANACGTC   50

TGAGCATCAC TTGAGCAAAA TCACCTGCAG GGG                          83

(2) INFORMATION FOR SEQ ID NO: 9:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

ATCCGCCTGA TTAGCGATAC TCACGTGATC CCATAAGGGC TGCGCAAAAT        50

AGCAGAGCAT CACTTGAGCA AAATCACCTG CAGGGG                       86

(2) INFORMATION FOR SEQ ID NO: 10:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

ATCCGCCTGA TTAGCGATAC TGGTGGACTA GAGGGCAGCA AACGATCCTT        50

GGTTAGCGTC CACTTGAGCA AAATCACCTG CAGGGG                       86
```

(2) INFORMATION FOR SEQ ID NO: 11:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

```
ATCCGCCTGA TTAGCGATAC TGGTGCGACG AGGCTTACAC AAACGTACAC        50

GTTTCCCCGC ACTTGAGCAA AATCACCTGC AGGGG                        85
```

(2) INFORMATION FOR SEQ ID NO: 12:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

```
ATCCGCCTGA TTAGCGATAC TTGTCGGAGC AGGGGCGTAC GAAAACTTTA        50

CAGTTCCCCC GACTTGAGCA AAATCACCTG CAGGGG                       86
```

(2) INFORMATION FOR SEQ ID NO: 13:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

```
ATCCGCCTGA TTAGCGATAC TAGTGGAACA GGGCACGGAG AGTCAAACTT        50

TGGTTTCCCC CACTTGAGCA AAATCACCTG CAGGGG                       86
```

(2) INFORMATION FOR SEQ ID NO: 14:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

```
ATCCGCCTGA TTAGCGATAC TGTGGGTAGG GATCGGTGGA TGCCTCGTCA        50

CTTCTAGTCC CACTTGAGCA AAATCACCTG CAGGGG                       86
```

(2) INFORMATION FOR SEQ ID NO: 15:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

```
ATCCGCCTGA TTAGCGATAC TGGGCGCCCT AAACAAAGGG TGGTCACTTC          50

TAGTCCCAGG AACTTGAGCA AAATCACCTG CAGGGG                         86

(2) INFORMATION FOR SEQ ID NO: 16:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

ATCCGCCTGA TTAGCGATAC TTCCGGGCTC GGGATTCGTG GTCACTTTCA          50

GTCCCGGATA TAACTTGAGC AAAATCACCT GCAGGGG                        87

(2) INFORMATION FOR SEQ ID NO: 17:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

ATCCGCCTGA TTAGCGATAC TATGGGAGGG CGCGTTCTTC GTGGTTACTT          50

TTAGTCCCGA CTTGAGCAAA ATCACCTGCA GGGG                           84

(2) INFORMATION FOR SEQ ID NO: 18:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ATCCGCCTGA TTAGCGATAC TACGGGAGGG CACGTTCTTC GTGGTTACTT          50

TTAGTCCCGA CTTGAGCAAA ATCACCTGCA GGGG                           84

(2) INFORMATION FOR SEQ ID NO: 19:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

ATCCGCCTGA TTAGCGATAC TGCTCGTAGG GGGCGATTCT TTCGCCGTTA          50

CTTCCAGTCC TACTTGAGCA AAATCACCTG CAGGGG                         86

(2) INFORMATION FOR SEQ ID NO: 20:

(i) SEQUENCE CHARACTERISTICS:
        (A) LENGTH: 86 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 20:

ATCCGCCTGA TTAGCGATAC TGAGGCATGT TAACATGAGC ATCGTCTCAC          50

GATCCTCAGC CACTTGAGCA AAATCACCTG CAGGGG                         86

(2) INFORMATION FOR SEQ ID NO: 21:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

ATCCGCCTGA TTAGCGATAC TCCACAGGCT ACGGCACGTA GAGCATCACC          50

ATGATCCTGT GACTTGAGCA AAATCACCTG CAGGGG                         86

(2) INFORMATION FOR SEQ ID NO: 22:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

ATCCGCCTGA TTAGCGATAC TGCGGGCATG GCACATGAGC ATCTCTGATC          50

CCGCAATCCT CACTTGAGCA AAATCACCTG CAGGGG                         86

(2) INFORMATION FOR SEQ ID NO: 23:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

ATCCGCCTGA TTAGCGATAC TACCGGGCTA CTTCGTAGAG CATCTCTGAT          50

CCCGGTGCTC GACTTGAGCA AAATCACCTG CAGGGG                         86

(2) INFORMATION FOR SEQ ID NO: 24:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

ATCCGCCTGA TTAGCGATAC TAAAGGGCGA ACGTAGGTCG AGGCATCCAT          50

TGGATCCCTT CACTTGAGCA AAATCACCTG CAGGGG                         86

(2) INFORMATION FOR SEQ ID NO: 25:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 25:

ATCCGCCTGA TTAGCGATAC TACGGGCTCT GTCACTGTGG CACTAGCAAT            50

AGTCCCGTCG CACTTGAGCA AAATCACCTG CAGGGG                           86

(2) INFORMATION FOR SEQ ID NO: 26:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 26:

ATCCGCCTGA TTAGCGATAC TGGGCAGACC TTCTGGACGA GCATCACCTA            50

TGTGATCCCG ACTTGAGCAA ATCACCTGC AGGGG                             85

(2) INFORMATION FOR SEQ ID NO: 27:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

ATCCGCCTGA TTAGCGATAC TAGAGGGGAA GTAGGCTGCC TGACTCGAGA            50

GAGTCCTCCC GACTTGAGCA AAATCACCTG CAGGGG                           86

(2) INFORMATION FOR SEQ ID NO: 28:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

ATCCGCCTGA TTAGCGATAC TAGGGGTGCG AAACACATAA TCCTCGCGGA            50

TTCCCATCGC TACTTGAGCA AAATCACCTG CAGGGG                           86

(2) INFORMATION FOR SEQ ID NO: 29:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 29:

ATCCGCCTGA TTAGCGATAC TGGGGGGGCA ATGGCGGTAC CTCTGGTCCC            50

```
CTAAATACAC TTGAGCAAAA TCACCTGCAG GGG                                    83

(2) INFORMATION FOR SEQ ID NO: 30:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

ATCCGCCTGA TTAGCGATAC TGCGGCTCAA AGTCCTGCTA CCCGCAGCAC                  50

ATCTGTGGTC ACTTGAGCAA ATCACCTGC AGGGG                                   85

(2) INFORMATION FOR SEQ ID NO: 31:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

ATCCGCCTGA TTAGCGATAC TTTGGGCGTG AATGTCCACG GGTACCTCCG                  50

GTCCCAAAGA GACTTGAGCA AAATCACCTG CAGGGG                                 86

(2) INFORMATION FOR SEQ ID NO: 32:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

ATCCGCCTGA TTAGCGATAC TTCCGCGCAA GTCCCTGGTA AAGGGCAGCC                  50

CTAACTGGTC ACTTGAGCAA AATCACCTGC AGGGG                                  85

(2) INFORMATION FOR SEQ ID NO: 33:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

ATCCGCCTGA TTAGCGATAC TCAAGTTCCC CACAAGACTG GGGCTGTTCA                  50

AACCGCTAGT AACTTGAGCA AAATCACCTG CAGGGG                                 86

(2) INFORMATION FOR SEQ ID NO: 34:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO: 34:

ATCCGCCTGA TTAGCGATAC TCAAGTAGGG CGCGACACAC GTCCGGGCAC        50

CTAAGGTCCC AACTTGAGCA AAATCACCTG CAGGGG                       86

(2) INFORMATION FOR SEQ ID NO: 35:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

ATCCGCCTGA TTAGCGATAC TAAAGTCGTG CAGGGTCCCC TGGAAGCATC        50

TCCGATCCCA GACTTGAGCA AAATCACCTG CAGGGG                       86

(2) INFORMATION FOR SEQ ID NO: 36:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 36:

GGGAGACAAG AAUAACGCUC AANNNNNNNN NNNNNNNNNN NNNNNNNNNN        50

NNNNNNNNNN NNNNNNNNNN NNUUCGACAG GAGGCUCACA ACAGGC            96

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 37:

TAATACGACT CACTATAGGG AGACAAGAAT AACGCTCAA                    39

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 38:

GCCTGTTGTG AGCCTCCTGT CGAA                                    24

(2) INFORMATION FOR SEQ ID NO: 39:

(i) SEQUENCE CHARACTERISTICS:
        (A) LENGTH: 93 base pairs
        (B) TYPE: nucleic acid
        (C) STRANDEDNESS: single
        (D) TOPOLOGY: linear

```
    (ii) MOLECULE TYPE: RNA (ix) FEATURE:
         (D) OTHER INFORMATION:  All pyrimidines are 2'-F modified (xi) SEQUENCE DESCRIPTION: SEQ ID NO: 39:

GGGAGACAAG AAUAACGCUC AACGGUGGCA UUUCUUCACU UCCUUCUCGC          50

UUUCUCGCGU UGGGCNCGAU UCGACAGGAG GCUCACAACA GGC                93

(2) INFORMATION FOR SEQ ID NO: 40:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All pyrimidines are 2'-F modified (xi) SEQUENCE DESCRIPTION: SEQ ID NO: 40:

GGGAGACAAG AAUAACGCUC AACCAACCUU CUGUCGGCGU UGCUUUUUGG          50

ACGGCACUCA GGCUCCAUUC GACAGGAGGC UCACAACAGG C                  91

(2) INFORMATION FOR SEQ ID NO: 41:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All pyrimidines are 2'-F modified (xi) SEQUENCE DESCRIPTION: SEQ ID NO: 41:

GGGAGACAAG AAUAACGCUC AAUCGAUCGG UUGUGUGCCG GACAGCCUUA          50

ACCAGGGCUG GGACCGAGGC CUUCGACAGG AGGCUCACAA CAGGC              95

(2) INFORMATION FOR SEQ ID NO: 42:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All pyrimidines are 2'-F modified (xi) SEQUENCE DESCRIPTION: SEQ ID NO: 42:

GGGAGACAAG AAUAACGCUC AACUGAGUAG GGGAGGAAGU UGAAUCAGUU          50

GUGGCGCCUC UCAUUCGCUU CGACAGGAGG CUCACAACAG GC                 92

(2) INFORMATION FOR SEQ ID NO: 43:

(i) SEQUENCE CHARACTERISTICS:
        (A) LENGTH: 95 base pairs
        (B) TYPE: nucleic acid
        (C) STRANDEDNESS: single
        (D) TOPOLOGY: linear
```

(ii) MOLECULE TYPE: RNA (ix) FEATURE:
            (D) OTHER INFORMATION: All pyrimidines are 2'-F modified (xi) SEQUENCE DESCRIPTION: SEQ ID NO: 43:

GGGAGACAAG AAUAACGCUC AACAGCACUU UCGCUUUUCA UCAUUUUUC      50

UUUCCACUGU UGGGCGCGGA AUUCGACAGG AGGCUCACAA CAGGC          95

(2) INFORMATION FOR SEQ ID NO: 44:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 44:

GGGAGACAAG AAUAACGCUC AAUCAGUGCU GGCGUCAUGU CUCGAUGGGG     50

AUUUUUCUUC AGCACUUUGC CAUUCGACAG GAGGCUCACA ACAGGC         96

(2) INFORMATION FOR SEQ ID NO: 45:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 45:

GGGAGACAAG AAUAACGCUC AAUCUACUUU CCAUUUCUCU UUUCUUCUCA     50

CGAGCGGGUU UCCAGUGAAC CAUUCGACAG GAGGCUCACA ACAGGC         96

(2) INFORMATION FOR SEQ ID NO: 46:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 46:

GGGAGACAAG AAUAACGCUC AACGAUAGUG ACUACGAUGA CGAAGGCCGC     50

GGGUUGGAUG CCCGCAUUGA UUCGACAGGA GGCUCACAAC AGGC           94

(2) INFORMATION FOR SEQ ID NO: 47:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-F modified (xi) SEQUENCE DESCRIPTION: SEQ ID NO: 47:

GGGAGACAAG AAUAACGCUC AAGUCGAUAC UGGCGACUUG CUCCAUUGGC         50

CGAUUAACGA UUCGGUCAGU UCGACAGGAG GCUCACAACA GGC                93

(2) INFORMATION FOR SEQ ID NO: 48:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-F modified (xi) SEQUENCE DESCRIPTION: SEQ ID NO: 48:

GGGAGACAAG AAUAACGCUC AAGUGCAAAC UUAACCCGGG AACCGCGCGU         50

UUCGAUCGAC UUUCCUUUCC AUUCGACAGG AGGCUCACAA CAGGC              95

(2) INFORMATION FOR SEQ ID NO: 49:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-F modified (xi) SEQUENCE DESCRIPTION: SEQ ID NO: 49:

GGGAGACAAG AAUAACGCUC AAAUUCCGCG UUCCGAUUAA UCCUGUGCUC         50

GGAAAUCGGU AGCCAUAGUG CAUUCGACAG GAGGCUCACA ACAGGC             96

(2) INFORMATION FOR SEQ ID NO: 50:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-F modified (xi) SEQUENCE DESCRIPTION: SEQ ID NO: 50:

GGGAGACAAG AAUAACGCUC AACGAACGAG GAGGGAGUGG CAAGGGAUGG         50

UUGGAUAGGC UCUACGCUCA UUCGACAGGA GGCUCACAAC AGGC               94

(2) INFORMATION FOR SEQ ID NO: 51:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 51:

GGGAGACAAG AAUAACGCUC AAGCGAAACU GGCGACUUGC UCCAUUGGCC         50

GAUAUAACGA UUCGGUUCAU UUCGACAGGA GGCUCACAAC AGGC              94

(2) INFORMATION FOR SEQ ID NO: 52:
    (i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 52:

GGGAGACAAG AAUAACGCUC AACGAACGAG GAGGGAGUCG CAAGGGAUGG         50

UUGGAUAGGC UCUACGCUCA AUUCGACAGG AGGCUCACAA CAGGC             95

(2) INFORMATION FOR SEQ ID NO: 53:
    (i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 53:

GGGAGACAAG AAUAACGCUC AACGAGAAGU GACUACGAUG ACGAAGGCCG         50

CGGGUUGAAU CCCUCAUUGA UUCGACAGGA GGCUCACAAC AGGC              94

(2) INFORMATION FOR SEQ ID NO: 54:
    (i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 54:

GGGAGACAAG AAUAACGCUC AAAAGCAACG AGACCUGACG CCUGAUGUGA         50

CUGUGCUUGC ACCCGAUUCU GUUCGACAGG AGGCUCACAA CAGGC             95

(2) INFORMATION FOR SEQ ID NO: 55:
    (i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 55:

GGGAGACAAG AAUAACGCUC AAGUGAUUCU CAUUCUCAAU GCUUUCUCAC            50

AACUUUUUCC ACUUCAGCGU GAUUCGACAG GAGGCUCACA CAGGC                95

(2) INFORMATION FOR SEQ ID NO: 56:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 56:

GGGAGACAAG AAUAACGCUC AAAAGCAACG AGACUCGACG CCUGAUGUGA            50

CUGUGCUUGC ACCCGAUUCU UUCGACAGGA GGCUCACAAC AGGC                 94

(2) INFORMATION FOR SEQ ID NO: 57:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 57:

GGGAGACAAG AAUAACGCUC AAUCGAUCGG UUGUGUGCCG GACAGCUUUG            50

ACCAUGAGCU GGGACCGAGG CCUUCGACAG GAGGCUCACA ACAGGC                96

(2) INFORMATION FOR SEQ ID NO: 58:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 58:

GGGAGACAAG AAUAACGCUC AANGACGNGU GGACCUGACU AAUCGACUGA            50

UCAAAGAUCC CGCCCAGAUG GGUUCGACAG GAGGCUCACA ACAGGC                96

(2) INFORMATION FOR SEQ ID NO: 59:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 59:

GGGAGACAAG AAUAACGCUC AACACUGCGA CUUGCAGAAG CCUUGUGUGG          50

CGGUACCCCC UUUGGCCUCG UUCGACAGGA GGCUCACAAC AGGC                94

(2) INFORMATION FOR SEQ ID NO: 60:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 60:

GGGAGACAAG AAUAACGCUC AAGGUGGCAU UCUUCAUUU UCCUUCUCGC           50

UUUCUCCGCC GUUGGGCGCG UUCGACAGGA GGCUCACAAC AGGC                94

(2) INFORMATION FOR SEQ ID NO: 61:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 61:

GGGAGACAAG AAUAACGCUC AACCUGAGUA GGGGGGAAAG UUGAAUCAGU          50

UGUGGCGCUC UACUCAUUCG CCUUCGACAG GAGGCUCACA ACAGGC              96

(2) INFORMATION FOR SEQ ID NO: 62:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 62:

GGGAGACAAG AAUAACGCUC AAGUCGAAAC UGGCGACUUG CUCCAUUGGC          50

CGAUAUAACG AUUCGGUUCA UUCGACAGGA GGCUCACAAC AGGC                94

(2) INFORMATION FOR SEQ ID NO: 63:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 63:

GGGAGACAAG AAUAACGCUC AAGCGAUACU GGCGACUUGC UCCAUUGGCC           50

GAUAUAACGA UUCGGCUCAG UUCGACAGGA GGCUCACAAC AGGC                94

(2) INFORMATION FOR SEQ ID NO: 64:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 64:

GGGAGACAAG AAUAACGCUC AAACGUGGGG CACAGGACCG AGAGUCCCUC           50

CGGCAAUAGC CGCUACCCCA CCUUCGACAG GAGGCUCACA ACAGGC              96

(2) INFORMATION FOR SEQ ID NO: 65:

(i) SEQUENCE CHARACTERISTICS:
            (A) LENGTH: 98 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 65:

GGGAGACAAG AAUAACGCUC AACACAGCCU NANAGGGGGG AAGUUGAAUC           50

AGUUGUGGCG CUCUACUCAU UCGCUUCGAC AGGAGGCUCA CAACAGGC            98

(2) INFORMATION FOR SEQ ID NO: 66:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 66:

GGGAGACAAG AAUAACGCUC AAANGGGNUA UGGUGACUUG CUCCAUUGGC           50

CGAUAUAACG AUUCGGUCAG UUCGACAGGA GGCUCACAAC AGGC                94

(2) INFORMATION FOR SEQ ID NO: 67:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 67:

GGGAGACAAG AAUAACGCUC AACCUGCGUA GGGNGGGAAG UUGAAUCAGU            50

UGUGGCGCUC UACUCAUUCG CCUUCGACAG GAGGCUCACA ACAGGC                96

(2) INFORMATION FOR SEQ ID NO: 68:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 68:

GGGAGACAAG AAUAACGCUC AACGAACGAG GAGGGAGUGG CAAGGGAUGG            50

UUGGAUAGGC UCUACGCUCA UUCGACAGGA GGCUCACAAC AGGC                  94

(2) INFORMATION FOR SEQ ID NO: 69:

(i) SEQUENCE CHARACTERISTICS:
            (A) LENGTH: 97 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 69:

GGGAGACAAG AAUAACGCUC AAGUGCAAAC UUAACCCGGG AACCGCGCGU            50

UUCGAUUCGC UUUCCNUAUU CCAUUCGACA GGAGGCUCAC AACAGGC               97

(2) INFORMATION FOR SEQ ID NO: 70:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 70:

GGGAGACAAG AAUAACGCUC AACGAACGAG GAGGGAGUGG CAAGGGACGG            50

UNNAUAGGCU CUACGCUCAU UCGACAGGAG GCUCACAACA GGC                   93

(2) INFORMATION FOR SEQ ID NO: 71:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 71:

GGGAGACAAG AAUAACGCUC AAUCGGUGUG GCUCAGAAAC UGACACGCGU          50

GAGCUUCGCA CACAUCUGCU UCGACAGGAG GCUCACAACA GGC                93

(2) INFORMATION FOR SEQ ID NO: 72:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 72:

GGGAGACAAG AAUAACGCUC AAUAUCGCUU UUCAUCAAUU CCACUUUUUC          50

ACUCUNUAAC UUGGGCGUGC AUUCGACAGG AGGCUCACAA CAGGC              95

(2) INFORMATION FOR SEQ ID NO: 73:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 73:

GGGAGACAAG AAUAACGCUC AAGUGCAAAC UUAACCCGGG AACCGCGCGU          50

UUCGAUCCUG CAUCCUUUUU CCUUCGACAG GAGGCUCACA ACAGGC             96

(2) INFORMATION FOR SEQ ID NO: 74:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 74:

GGGAGACAAG AAUAACGCUC AAUCGNUCGG UUGUGUGCCG GCAGCUUUGU          50

CCAGCGUUGG GCCGAGGCCU UCGACAGGAG GCUCACAACA GGC                93

(2) INFORMATION FOR SEQ ID NO: 75:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 75:

GGGAGACAAG AAUAACGCUC AAAGUACCCA UCUCAUCUUU UCCUUUCCUU          50

UCUUCAAGGC ACAUUGAGGG UUUCGACAGG AGGCUCACAA CAGGC               95

(2) INFORMATION FOR SEQ ID NO: 76:

(i) SEQUENCE CHARACTERISTICS:
            (A) LENGTH: 97 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 76:

GGGAGACAAG AAUAACGCUC AACCUGAGUA GGGGGGGAAG UUGAACCAGU          50

UGUGGCNGCC UACUCAUUCN CCAUUCGACA GGAGGCUCAC AACAGGC             97

(2) INFORMATION FOR SEQ ID NO: 77:

(i) SEQUENCE CHARACTERISTICS:
            (A) LENGTH: 94 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 77:

GGGAGACAAG AAUAACGCUC AACCNNCCUN CUGUCGGCGC UUGUCUUUUU          50

GGACGGGCAA CCCAGGGCUC UUCGACAGGA GGCUCACAAC AGGC                94

(2) INFORMATION FOR SEQ ID NO: 78:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 78:

GGGAGACAAG AAUAACGCUC AACCAACCUN CUGUCGGCGC UUGUCUUUUU          50

GGACGAGCAA CUCAAGGCUC GUUUCGACAG GAGGCUCACA ACAGGC              96

(2) INFORMATION FOR SEQ ID NO: 79:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 79:

GGGAGACAAG AAUAACGCUC AACCAGCGCA GAUCCCGGGC UGAAGUGACU         50

GCCGGCAACG GCCGCUCCAU UCGACAGGAG GCUCACAACA GGC               93

(2) INFORMATION FOR SEQ ID NO: 80:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 80:

GGGAGACAAG AAUAACGCUC AAUUCCCGUA ACAACUUUUC AUUUUCACUU         50

UUCAUCCAAC CAGUGAGCAG CAUUCGACAG GAGGCUCACA ACAGGC             96

(2) INFORMATION FOR SEQ ID NO: 81:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 81:

GGGAGACAAG AAUAACGCUC AAUAUCGCUU UCAUCAAAUU CCACUCCUUC         50

ACUUCUUUAA CUUGGGCGUG CAUUCGACAG GAGGCUCACA ACAGGC             96

(2) INFORMATION FOR SEQ ID NO: 82:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: N at positions 1 and 23 is any base
                pair.

(ix) FEATURE:
            (D) OTHER INFORMATION: N at positions 5 and 10 is any base
                pair.

(ix) FEATURE:
            (D) OTHER INFORMATION: N at positions 6 and 9 is any base
                pair.

(ix) FEATURE:
            (D) OTHER INFORMATION: N at positions 7 and 8 is any base
                pair.

(xi) SEQUENCE DESCRIPTION: SEQ ID NO: 82:

```
NGGCNNNNNNN GRKYAYYRRT CCN                                                   23

(2) INFORMATION FOR SEQ ID NO: 83:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION:  Nucleotide 38 is an inverted
             orientation T (3'-3'-linked)

(xi) SEQUENCE DESCRIPTION: SEQ ID NO: 83:

TGGGAGGGCG CGTTCTTCGT GGTTACTTTT AGTCCCGT                                     38

(2) INFORMATION FOR SEQ ID NO: 84:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION:  Nucleotide 40 is an inverted
             orientation T (3'-3'-linked)

(xi) SEQUENCE DESCRIPTION: SEQ ID NO: 84:

CACAGGCTAC GGCACGTAGA GCATCACCAT GATCCTGTGT                                   40

(2) INFORMATION FOR SEQ ID NO: 85:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION:  Nucleotide 45 is an inverted
             orientation T (3'-3'-linked)

(xi) SEQUENCE DESCRIPTION: SEQ ID NO: 85:

TACTCAGGGC ACTGCAAGCA ATTGTGGTCC CAATGGGCTG AGTAT                             45

(2) INFORMATION FOR SEQ ID NO: 86:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION:  C at positions 11, 25 and 26 is 2'-O-
             Methyl-2'-deoxycytidine.

(ix) FEATURE:
         (D) OTHER INFORMATION:  G at positions 9, 10, 17, 19 and 35 is
             2'-O-Methyl-2'-deoxyguanosine.

(ix) FEATURE:
         (D) OTHER INFORMATION:  A at positions 12, 24 and 27 is 2'-O-
```

-continued

Methyl-2'-deoxyadenosine.

(ix) FEATURE:
       (D) OTHER INFORMATION: U at positions 6, 22 and 34 is 2'-
           fluoro-2'-deoxyuridine.

(ix) FEATURE:
       (D) OTHER INFORMATION: C at positions 8, 23, 32 and 33 is 2'-
           fluoro-2'-deoxycytidine.

(ix) FEATURE:
       (D) OTHER INFORMATION: Nucleotide 36 is an inverted
           orientation T (3'-3'-linked).

(xi) SEQUENCE DESCRIPTION: SEQ ID NO: 86:

CAGGCUACGG CACGTAGAGC AUCACCATGA TCCUGT                                   36

(2) INFORMATION FOR SEQ ID NO: 87:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (ix) FEATURE:
       (D) OTHER INFORMATION: G at positions 9, 15, 17 and 31 is 2'-
           O-methyl-2'-deoxyguanosine.

(ix) FEATURE:
       (D) OTHER INFORMATION: A at position 22 is 2'-O-methyl-2'-
           deoxyadenine.

(ix) FEATURE:
       (D) OTHER INFORMATION: U at positions 6, 20 and 30 is 2'-
           fluoro-2'-deoxyuridine.

(ix) FEATURE:
       (D) OTHER INFORMATION: C at positions 8, 21, 28 and 29 is 2'-
           fluoro-2'-deoxycytidine.

(ix) FEATURE:
       (D) OTHER INFORMATION: N at positions 10 and 23 is
           hexaethylene glycol phosphoramidite spacer.

(ix) FEATURE:
       (D) OTHER INFORMATION: Nucleotide 32 is an inverted
           orientation T (3'-3'-linked).

(xi) SEQUENCE DESCRIPTION: SEQ ID NO: 87:

CAGGCUACGN CGTAGAGCAU CANTGATCCU GT                                       32

(2) INFORMATION FOR SEQ ID NO: 88:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (ix) FEATURE:
       (D) OTHER INFORMATION: Nucleotide 39 is an inverted
           orientation T (3'-3'-linked).

(xi) SEQUENCE DESCRIPTION: SEQ ID NO: 88:

CAGTCCGTGG TAGGGCAGGT TGGGGTGACT TCGTGGAAT                                39

(2) INFORMATION FOR SEQ ID NO: 89:

(i) SEQUENCE CHARACTERISTICS:

(A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at positions 13, 14, 16 and 17 is
            substituted with IdU.

(xi) SEQUENCE DESCRIPTION: SEQ ID NO: 89:

TGGGAGGGCG CGTTCTTCGT GGTTACTTTT AGTCCCG                                     37

(2) INFORMATION FOR SEQ ID NO: 90:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at position 20 is substituted with
            IdU.

(xi) SEQUENCE DESCRIPTION: SEQ ID NO: 90:

TGGGAGGGCG CGTTCTTCGT GGTTACTTTT AGTCCCG                                     37

(2) INFORMATION FOR SEQ ID NO: 91:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at position 23 is substituted with
            IdU.

(xi) SEQUENCE DESCRIPTION: SEQ ID NO: 91:

TGGGAGGGCG CGTTCTTCGT GGTTACTTTT AGTCCCG                                     37

(2) INFORMATION FOR SEQ ID NO: 92:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at position 24 is substituted with
            IdU.

(xi) SEQUENCE DESCRIPTION: SEQ ID NO: 92:

TGGGAGGGCG CGTTCTTCGT GGTTACTTTT AGTCCCG                                     37

(2) INFORMATION FOR SEQ ID NO: 93:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at position 27 is substituted with
            IdU.

(xi) SEQUENCE DESCRIPTION: SEQ ID NO: 93:

TGGGAGGGCG CGTTCTTCGT GGTTACTTTT AGTCCCG                                         37

(2) INFORMATION FOR SEQ ID NO: 94:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at positions 28-30 is substituted
            with IdU.

(xi) SEQUENCE DESCRIPTION: SEQ ID NO: 94:

TGGGAGGGCG CGTTCTTCGT GGTTACTTTT AGTCCCG                                         37

(2) INFORMATION FOR SEQ ID NO: 95:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  T at position 33 is substituted with
            IdU.

(xi) SEQUENCE DESCRIPTION: SEQ ID NO: 95:

TGGGAGGGCG CGTTCTTCGT GGTTACTTTT AGTCCCG                                         37

(2) INFORMATION FOR SEQ ID NO: 96:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (ix) FEATURE:
        (D) OTHER INFORMATION:  Xaa at position 5 is a modified amino
            acid that could not be identified.

(xi) SEQUENCE DESCRIPTION: SEQ ID NO: 96:

Lys Lys Pro Ile Xaa Lys Lys
                5

(2) INFORMATION FOR SEQ ID NO: 97:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
            (D) OTHER INFORMATION:  C at positions 1 and 3 is 2'-O-Methyl-
                2'-deoxycytidine.

(ix) FEATURE:
            (D) OTHER INFORMATION:  A at position 2 is 2'-O-Methyl-2'-
                deoxyadenosine.

(ix) FEATURE:
            (D) OTHER INFORMATION:  G at positions 37 and 39 is 2'-O-
                Methyl-2'-deoxyguanosine.

(ix) FEATURE:
            (D) OTHER INFORMATION:  U at position 38 is 2'-O-Methyl-2'-
                deoxyuridine.

(ix) FEATURE:
            (D) OTHER INFORMATION:  Nucleotide 40 is an inverted
                orientation T (3'-3'-linked).

(xi) SEQUENCE DESCRIPTION: SEQ ID NO: 97:

CACAGGCTAC GGCACGTAGA GCATCACCAT GATCCTGUGT                              40

(2) INFORMATION FOR SEQ ID NO: 98:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  C at positions 10, 13 and 15 is 2'-O-
            Methyl-2'-deoxycytidine.

(ix) FEATURE:
        (D) OTHER INFORMATION:  G at positions 11, 12 and 16 is 2'-O-
            Methyl-2'-deoxyguanosine.

(ix) FEATURE:
        (D) OTHER INFORMATION:  A at position 14 is 2'-O-Methyl-2'-
            deoxyadenosine.

(ix) FEATURE:
        (D) OTHER INFORMATION:  U at position 17 is 2'-O-Methyl-2'-
            deoxyuridine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 98:

CACAGGCTAC GGCACGUAGA GCATCACCAT GATCCTGTGT                              40

(2) INFORMATION FOR SEQ ID NO: 99:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  A at positions 26 and 29 is 2'-O-
            Methyl-2'-deoxyadenosine.

(ix) FEATURE:
        (D) OTHER INFORMATION:  C at positions 27 and 28 is 2'-O-
            Methyl-2'-deoxycytidine.

(ix) FEATURE:
        (D) OTHER INFORMATION:  U at position 30 is 2'-O-Methyl-2'-

```
        deoxyuridine.
    (ix) FEATURE:
        (D) OTHER INFORMATION:  Nucleotide 40 is an inverted
            orientation T (3'-3'-linked).

(xi) SEQUENCE DESCRIPTION: SEQ ID NO: 99:

CACAGGCTAC GGCACGTAGA GCATCACCAU GATCCTGTGT                                40

(2) INFORMATION FOR SEQ ID NO: 100:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  C at positions 1, 3, 10, 13, 15, 27,
            and 28 is 2'-O-Methyl-2'-deoxycytidine.

(ix) FEATURE:
        (D) OTHER INFORMATION:  A at positions 2, 14, 26 and 29 is 2'-
            O-Methyl-2'-deoxyadenosine.

(ix) FEATURE:
        (D) OTHER INFORMATION:  G at positions 11, 12 and 16 is 2'-O-
            Methyl-2'-deoxyguanosine.

(ix) FEATURE:
        (D) OTHER INFORMATION:  U at positions 17 and 30 is 2'-O-
            Methyl-2'-deoxyuridine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 100:

CACAGGCTAC GGCACGUAGA GCATCACCAU GATCCTGTGT                                40

(2) INFORMATION FOR SEQ ID NO: 101:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  C at positions 25, 27 and 28 is 2'-O-
            Methyl-2'-deoxycytidine.

(ix) FEATURE:
        (D) OTHER INFORMATION:  A at positions 26 and 29 is 2'-O-
            Methyl-2'-deoxyadenosine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 101:

CACAGGCTAC GGCACGTAGA GCATCACCAT GATCCTGTGT                                40

(2) INFORMATION FOR SEQ ID NO: 102:

(i) SEQUENCE CHARACTERISTICS:
        (A) LENGTH: 40 base pairs
        (B) TYPE: nucleic acid
        (C) STRANDEDNESS: single
        (D) TOPOLOGY: linear
```

(ii) MOLECULE TYPE: DNA (ix) FEATURE:
(D) OTHER INFORMATION: A at positions 4 and 9 is 2'-O-Methyl-2'-deoxyadenosine.

(ix) FEATURE:
(D) OTHER INFORMATION: G at positions 5 and 6 is 2'-O-Methyl-2'-deoxyguanosine.

(ix) FEATURE:
(D) OTHER INFORMATION: C at position 7 is 2'-O-Methyl-2'-deoxycytidine.

(ix) FEATURE:
(D) OTHER INFORMATION: U at position 8 is 2'-O-Methyl-2'-deoxyuridine.

(ix) FEATURE:
(D) OTHER INFORMATION: Nucleotide 40 is an inverted orientation T (3'-3'-linked).

(xi) SEQUENCE DESCRIPTION: SEQ ID NO: 102:

CACAGGCUAC GGCACGTAGA GCATCACCAT GATCCTGTGT                40

(2) INFORMATION FOR SEQ ID NO: 103:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: G at position 31 is 2'-O-Methyl-2'-deoxyguanosine.

(ix) FEATURE:
(D) OTHER INFORMATION: A at position 32 is 2'-O-Methyl-2'-deoxyadenosine.

(ix) FEATURE:
(D) OTHER INFORMATION: U at positions 33 and 36 is 2'-O-Methyl-2'-deoxyuridine.

(ix) FEATURE:
(D) OTHER INFORMATION: C at positions 34 and 35 is 2'-O-Methyl-2'-deoxycytidine.

(ix) FEATURE:
(D) OTHER INFORMATION: Nucleotide 40 is an inverted orientation T (3'-3'-linked).

(xi) SEQUENCE DESCRIPTION: SEQ ID NO: 103:

CACAGGCTAC GGCACGTAGA GCATCACCAT GAUCCUGTGT                40

(2) INFORMATION FOR SEQ ID NO: 104:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: U at positions 17 and 24 is 2'-O-Methyl-2'-deoxyuridine.

(ix) FEATURE:
(D) OTHER INFORMATION: A at position 23 is 2'-O-Methyl-2'-deoxyadenosine.

(ix) FEATURE:
            (D) OTHER INFORMATION:  Nucleotide 40 is an inverted
                orientation T (3'-3'-linked).

(xi) SEQUENCE DESCRIPTION: SEQ ID NO: 104:

CACAGGCTAC GGCACGUAGA GCAUCACCAT GATCCTGTGT                                40

(2) INFORMATION FOR SEQ ID NO: 105:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION:  G at positions 19 and 21 is 2'-O-
                Methyl-2'-deoxyguanosine.

(ix) FEATURE:
            (D) OTHER INFORMATION:  A at position 20 is 2'-O-Methyl-2'-
                deoxyadenosine.

(ix) FEATURE:
            (D) OTHER INFORMATION:  C at position 22 is 2'-O-Methyl-2'-
                deoxycytidine.

(ix) FEATURE:
            (D) OTHER INFORMATION:  Nucleotide 40 is an inverted
                orientation T (3'-3'-linked).

(xi) SEQUENCE DESCRIPTION: SEQ ID NO: 105:

CACAGGCTAC GGCACGTAGA GCATCACCAT GATCCTGTGT                                40

(2) INFORMATION FOR SEQ ID NO: 106:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION:  A at position 20 is 2'-O-Methyl-2'-
                deoxyadenosine.

(ix) FEATURE:
            (D) OTHER INFORMATION:  G at position 21 is 2'-O-Methyl-2'-
                deoxyguanosine.

(ix) FEATURE:
            (D) OTHER INFORMATION:  C at position 22 is 2'-O-Methyl-2'-
                deoxycytidine.

(ix) FEATURE:
            (D) OTHER INFORMATION:  Nucleotide 40 is an inverted
                orientation T (3'-3'-linked).

(xi) SEQUENCE DESCRIPTION: SEQ ID NO: 106:

CACAGGCTAC GGCACGTAGA GCATCACCAT GATCCTGTGT                                40

(2) INFORMATION FOR SEQ ID NO: 107:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (ix) FEATURE:
        (D) OTHER INFORMATION:  G at positions 12 and 16 is 2'-O-
            Methyl-2'-deoxyguanosine.

(ix) FEATURE:
        (D) OTHER INFORMATION:  C at positions 13 and 15 is 2'-O-
            Methyl-2'-deoxycytidine.

(ix) FEATURE:
        (D) OTHER INFORMATION:  A at position 14 is 2'-O-Methyl-2'-
            deoxyadenosine.

(ix) FEATURE:
        (D) OTHER INFORMATION:  U at position 17 is 2'-O-Methyl-2'-
            deoxyuridine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 107:

CACAGGCTAC GGCACGUAGA GCATCACCAT GATCCTGTGT                              40

(2) INFORMATION FOR SEQ ID NO: 108:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  C at positions 10 and 13 is 2'-O-
            Methyl-2'-deoxycytidine.

(ix) FEATURE:
        (D) OTHER INFORMATION:  G at positions 11 and 12 is 2'-O-
            Methyl-2'-deoxyguanosine.

(ix) FEATURE:
        (D) OTHER INFORMATION:  A at position 14 is 2'-O-Methyl-2'-
            deoxyadenosine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 108:

CACAGGCTAC GGCACGTAGA GCATCACCAT GATCCTGTGT                              40

(2) INFORMATION FOR SEQ ID NO: 109:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  C at positions 1 and 3 is 2'-O-
            Methyl-2'-deoxycytidine.

(ix) FEATURE:
        (D) OTHER INFORMATION:  A at positions 2 and 4 is 2'-O-
            Methyl-2'-deoxyadenosine.

(ix) FEATURE:
        (D) OTHER INFORMATION:  Nucleotide 40 is an inverted
            orientation T (3'-3'-linked).

(xi) SEQUENCE DESCRIPTION: SEQ ID NO: 109:

CACAGGCTAC GGCACGTAGA GCATCACCAT GATCCTGTGT                40

(2) INFORMATION FOR SEQ ID NO: 110:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: U at positions 36 and 38 is 2'-O-
             Methyl-2'-deoxyuridine.

(ix) FEATURE:
         (D) OTHER INFORMATION: G at positions 37 and 39 is 2'-O-
             Methyl-2'-deoxyguanosine.

(ix) FEATURE:
         (D) OTHER INFORMATION: Nucleotide 40 is an inverted
             orientation T (3'-3'-linked).

(xi) SEQUENCE DESCRIPTION: SEQ ID NO: 110:

CACAGGCTAC GGCACGTAGA GCATCACCAT GATCCUGUGT                40

(2) INFORMATION FOR SEQ ID NO: 111:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ix) FEATURE:
         (D) OTHER INFORMATION: C at position 7 is 2'-fluoro-2'-
             deoxycytidine.

(ix) FEATURE:
         (D) OTHER INFORMATION: Nucleotide 40 is an inverted
             orientation T (3'-3'-linked).

(xi) SEQUENCE DESCRIPTION: SEQ ID NO: 111:

CACAGGCTAC GGCACGTAGA GCATCACCAT GATCCTGTGT                40

(2) INFORMATION FOR SEQ ID NO: 112:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ix) FEATURE:
         (D) OTHER INFORMATION: C at position 22 is 2'-fluoro-2'-
             deoxycytidine.

(ix) FEATURE:
         (D) OTHER INFORMATION: Nucleotide 40 is an inverted
             orientation T (3'-3'-linked).

(xi) SEQUENCE DESCRIPTION: SEQ ID NO: 112:

CACAGGCTAC GGCACGTAGA GCATCACCAT GATCCTGTGT                40

(2) INFORMATION FOR SEQ ID NO: 113:

(i) SEQUENCE CHARACTERISTICS:
         (A) LENGTH: 40 base pairs
         (B) TYPE: nucleic acid
         (C) STRANDEDNESS: single (D) TOPOLOGY: linear (ix) FEATURE:
        (D) OTHER INFORMATION: C at position 25 is 2'-fluoro-2'-
            deoxycytidine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 113:

CACAGGCTAC GGCACGTAGA GCATCACCAT GATCCTGTGT                              40

(2) INFORMATION FOR SEQ ID NO: 114:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: C at position 34 is 2'-fluoro-2'-
            deoxycytidine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 114:

CACAGGCTAC GGCACGTAGA GCATCACCAT GATCCTGTGT                              40

(2) INFORMATION FOR SEQ ID NO: 115:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: C at position 35 is 2'-fluoro-2'-
            deoxycytidine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 115:

CACAGGCTAC GGCACGTAGA GCATCACCAT GATCCTGTGT                              40

(2) INFORMATION FOR SEQ ID NO: 116:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: U at position 8 is 2'-fluoro-2'-
            deoxyuridine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 116:

CACAGGCUAC GGCACGTAGA GCATCACCAT GATCCTGTGT                              40

(2) INFORMATION FOR SEQ ID NO: 117:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION:   U at position 17 is 2'-fluoro-2'-
                deoxyuridine.

(ix) FEATURE:
            (D) OTHER INFORMATION:   Nucleotide 40 is an inverted
                orientation T (3'-3'-linked).

(xi) SEQUENCE DESCRIPTION: SEQ ID NO: 117:

CACAGGCTAC GGCACGUAGA GCATCACCAT GATCCTGTGT                              40

(2) INFORMATION FOR SEQ ID NO: 118:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION:   U at position 24 is 2'-fluoro-2'-
                deoxyuridine.

(ix) FEATURE:
            (D) OTHER INFORMATION:   Nucleotide 40 is an inverted
                orientation T (3'-3'-linked).

(xi) SEQUENCE DESCRIPTION: SEQ ID NO: 118:

CACAGGCTAC GGCACGTAGA GCAUCACCAT GATCCTGTGT                              40

(2) INFORMATION FOR SEQ ID NO: 119:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION:   U at position 30 is 2'-fluoro-2'-
                deoxyuridine.

(ix) FEATURE:
            (D) OTHER INFORMATION:   Nucleotide 40 is an inverted
                orientation T (3'-3'-linked).

(xi) SEQUENCE DESCRIPTION: SEQ ID NO: 119:

CACAGGCTAC GGCACGTAGA GCATCACCAU GATCCTGTGT                              40

(2) INFORMATION FOR SEQ ID NO: 120:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION:   U at position 33 is 2'-fluoro-2'-
                deoxyuridine.

(ix) FEATURE:
            (D) OTHER INFORMATION:   Nucleotide 40 is an inverted
                orientation T (3'-3'-linked).

(xi) SEQUENCE DESCRIPTION: SEQ ID NO: 120:

CACAGGCTAC GGCACGTAGA GCATCACCAT GAUCCTGTGT                              40

(2) INFORMATION FOR SEQ ID NO: 121:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: C at positions 7, 22, 25, 34 and 35 is
            2'-fluoro-2'-deoxycytidine.

(ix) FEATURE:
        (D) OTHER INFORMATION: U at positions 8, 17, 24, 33 and 36 is
            2'-fluoro-2'-deoxyuridine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 121:

CACAGGCUAC GGCACGUAGA GCAUCACCAT GAUCCUGTGT                    40

(2) INFORMATION FOR SEQ ID NO: 122:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: C at positions 10, 13, 27 and 28 is
            2'-O-Methyl-2'-deoxycytidine.

(ix) FEATURE:
        (D) OTHER INFORMATION: G at positions 11, 12, 37 and 39 is
            2'-O-Methyl-2'-deoxyguanosine.

(ix) FEATURE:
        (D) OTHER INFORMATION: A at positions 14, 26 and 29 is 2'-O-
            Methyl-2'-deoxyadenosine.

(ix) FEATURE:
        (D) OTHER INFORMATION: C at position 34 is 2'-fluoro-2'-
            deoxycytidine.

(ix) FEATURE:
        (D) OTHER INFORMATION: U at position 38 is 2'-O-Methyl-2'-
            deoxyuridine.

(ix) FEATURE:
        (D) OTHER INFORMATION: Nucleotide 40 is an inverted
            orientation T (3'-3'-linked).

(xi) SEQUENCE DESCRIPTION: SEQ ID NO: 122:

CACAGGCTAC GGCACGTAGA GCATCACCAT GATCCTGUGT                    40

(2) INFORMATION FOR SEQ ID NO: 123:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (D) OTHER INFORMATION: C at positions 10, 13, 25, 27 and 28
            is 2'-O-Methyl-2'-deoxycytidine.

(ix) FEATURE:
        (D) OTHER INFORMATION: G at positions 11, 12, 37 and 39 is
            2'-O-Methyl-2'-deoxyguanosine.

(ix) FEATURE:
                (D) OTHER INFORMATION: A at positions 14, 26 and 29 is 2'-O-
                    Methyl-2'-deoxyadenosine.

(ix) FEATURE:
                (D) OTHER INFORMATION: C at position 34 is 2'-fluoro-2'-
                    deoxycytidine.

(ix) FEATURE:
                (D) OTHER INFORMATION: U at positions 36 and 38 is 2'-O-
                    Methyl-2'-deoxyuridine.

(ix) FEATURE:
                (D) OTHER INFORMATION: Nucleotide 40 is an inverted
                    orientation T (3'-3'-linked).

(xi) SEQUENCE DESCRIPTION: SEQ ID NO: 123:

CACAGGCTAC GGCACGTAGA GCATCACCAT GATCCUGUGT                                       40

(2) INFORMATION FOR SEQ ID NO: 124:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION: U at positions 8 and 24 is 2'-fluoro-
                2'-deoxyuridine.

(ix) FEATURE:
            (D) OTHER INFORMATION: C at positions 10, 13, 27 and 28 is
                2'-O-Methyl-2'-deoxycytidine.

(ix) FEATURE:
            (D) OTHER INFORMATION: G at positions 11, 12, 37 and 39 is
                2'-O-Methyl-2'-deoxyguanosine.

(ix) FEATURE:
            (D) OTHER INFORMATION: A at positions 14, 26 and 29 is 2'-O-
                Methyl-2'-deoxyadenosine.

(ix) FEATURE:
            (D) OTHER INFORMATION: C at positions 25, 34 and 35 is 2'-
                fluoro-2'-deoxycytidine.

(ix) FEATURE:
            (D) OTHER INFORMATION: U at positions 36 and 38 is 2'-O-
                Methyl-2'-deoxyuridine.

(ix) FEATURE:
            (D) OTHER INFORMATION: Nucleotide 40 is an inverted
                orientation T (3'-3'-linked).

(xi) SEQUENCE DESCRIPTION: SEQ ID NO: 124:

CACAGGCUAC GGCACGTAGA GCAUCACCAT GATCCUGUGT                                       40

(2) INFORMATION FOR SEQ ID NO: 125:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (D) OTHER INFORMATION: C at positions 10, 13, 25, 27 and 28
                is 2'-O-Methyl-2'-deoxycytidine.

(ix) FEATURE:
            (D) OTHER INFORMATION: G at positions 11, 12, 37 and 39 is
                2'-O-Methyl-2'-deoxyguanosine.

(ix) FEATURE:
            (D) OTHER INFORMATION: A at positions 14, 26 and 29 is 2'-O-

-continued

Methyl-2'-deoxyadenosine.

(ix) FEATURE:
(D) OTHER INFORMATION: C at positions 34 and 35 is 2'-fluoro-2'-deoxycytidine.

(ix) FEATURE:
(D) OTHER INFORMATION: U at positions 36 and 38 is 2'-O-Methyl-2'-deoxyuridine.

(ix) FEATURE:
(D) OTHER INFORMATION: Nucleotide 40 is an inverted orientation T (3'-3'-linked).

(xi) SEQUENCE DESCRIPTION: SEQ ID NO: 125:

CACAGGCTAC GGCACGTAGA GCATCACCAT GATCCUGUGT                40

(2) INFORMATION FOR SEQ ID NO: 126:

(i) SEQUENCE CHARACTERISTICS:
(A) LENGTH: 40 base pairs
(B) TYPE: nucleic acid
(C) STRANDEDNESS: single
(D) TOPOLOGY: linear (ix) FEATURE:
(D) OTHER INFORMATION: U at position 8 is 2'-fluoro-2'-deoxyuridine.

(ix) FEATURE:
(D) OTHER INFORMATION: C at positions 10, 13, 25, 27 and 28 is 2'-O-Methyl-2'-deoxycytidine.

(ix) FEATURE:
(D) OTHER INFORMATION: G at positions 11, 12, 37 and 39 is 2'-O-Methyl-2'-deoxyguanosine.

(ix) FEATURE:
(D) OTHER INFORMATION: A at positions 14, 26 and 29 is 2'-O-Methyl-2'-deoxyadenosine.

(ix) FEATURE:
(D) OTHER INFORMATION: C at position 34 is 2'-fluoro-2'-deoxycytidine.

(ix) FEATURE:
(D) OTHER INFORMATION: U at positions 36 and 38 is 2'-O-Methyl-2'-deoxyuridine.

(ix) FEATURE:
(D) OTHER INFORMATION: Nucleotide 40 is an inverted orientation T (3'-3'-linked).

(xi) SEQUENCE DESCRIPTION: SEQ ID NO: 126:

CACAGGCUAC GGCACGTAGA GCATCACCAT GATCCUGUGT                40

(2) INFORMATION FOR SEQ ID NO: 127:

(i) SEQUENCE CHARACTERISTICS:
(A) LENGTH: 36 base pairs
(B) TYPE: nucleic acid
(C) STRANDEDNESS: single
(D) TOPOLOGY: linear (ix) FEATURE:
(D) OTHER INFORMATION: U at positions 6 and 22 is 2'-fluoro-2'-deoxyuridine.

(ix) FEATURE:
(D) OTHER INFORMATION: C at positions 8, 11, 25 and 26 is 2'-O-Methyl-2'-deoxycytidine.

(ix) FEATURE:
(D) OTHER INFORMATION: G at positions 9, 10, and 35 is 2'-O-Methyl-2'-deoxyguanosine.

(ix) FEATURE:
            (D) OTHER INFORMATION: A at positions 12, 24 and 27 is 2'-O-
                Methyl-2'-deoxyadenosine.

(ix) FEATURE:
            (D) OTHER INFORMATION: C at positions 23, 32 and 33 is 2'-
                fluoro-2'-deoxycytidine.

(ix) FEATURE:
            (D) OTHER INFORMATION: U at position 34 is 2'-O-Methyl-2'-
                deoxyuridine.

(ix) FEATURE:
            (D) OTHER INFORMATION: Nucleotide 36 is an inverted
                orientation T (3'-3'-linked).

(xi) SEQUENCE DESCRIPTION: SEQ ID NO: 127:

CAGGCUACGG CACGTAGAGC AUCACCATGA TCCUGT                                    36

(2) INFORMATION FOR SEQ ID NO: 128:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ix) FEATURE:
         (D) OTHER INFORMATION: U at positions 6 and 20 is 2'-fluoro-
             2'-deoxyuridine.

(ix) FEATURE:
         (D) OTHER INFORMATION: C at positions 7, 10, 23 and 24 is 2'-
             O-Methyl-2'-deoxycytidine.

(ix) FEATURE:
         (D) OTHER INFORMATION: G at positions 8, 9, and 33 is 2'-O-
             Methyl-2'-deoxyguanosine.

(ix) FEATURE:
         (D) OTHER INFORMATION: A at positions 11, 22 and 25 is 2'-O-
             Methyl-2'-deoxyadenosine.

(ix) FEATURE:
         (D) OTHER INFORMATION: C at positions 21, 30 and 31 is 2'-
             fluoro-2'-deoxycytidine.

(ix) FEATURE:
         (D) OTHER INFORMATION: U at position 32 is 2'-O-Methyl-2'-
             deoxyuridine.

(ix) FEATURE:
         (D) OTHER INFORMATION: Nucleotide 34 is an inverted
             orientation T (3'-3'-linked).

(xi) SEQUENCE DESCRIPTION: SEQ ID NO: 128:

CAGGCUCGGC ACGAGAGCAU CACCATGATC CUGT                                      34

(2) INFORMATION FOR SEQ ID NO: 129:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ix) FEATURE:
         (D) OTHER INFORMATION: U at positions 6 and 20 is 2'-fluoro-
             2'-deoxyuridine.

(ix) FEATURE:
         (D) OTHER INFORMATION: C at positions 7, 10, 22 and 23 is 2'-
             O-Methyl-2'-deoxycytidine.

(ix) FEATURE:
         (D) OTHER INFORMATION: G at positions 8, 9, and 31 is 2'-O-

Methyl-2'-deoxyguanosine.

(ix) FEATURE:
 (D) OTHER INFORMATION: A at positions 11 and 24 is 2'-O-Methyl-2'-deoxyadenosine.

(ix) FEATURE:
 (D) OTHER INFORMATION: C at positions 21, 28 and 29 is 2'-fluoro-2'-deoxycytidine.

(ix) FEATURE:
 (D) OTHER INFORMATION: U at position 30 is 2'-O-Methyl-2'-deoxyuridine.

(ix) FEATURE:
 (D) OTHER INFORMATION: Nucleotide 32 is an inverted orientation T (3'-3'-linked).

(xi) SEQUENCE DESCRIPTION: SEQ ID NO: 129:

CAGGCUCGGC ACGAGAGCAU CCCAGATCCU GT          32

(2) INFORMATION FOR SEQ ID NO: 130:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ix) FEATURE:
  (D) OTHER INFORMATION: C at positions 8, 11, 23, 25, 26, 32 and 33 is 2'-O-Methyl-2'-deoxycytidine.

(ix) FEATURE:
  (D) OTHER INFORMATION: G at positions 9, 10, and 35 is 2'-O-Methyl-2'-deoxyguanosine.

(ix) FEATURE:
  (D) OTHER INFORMATION: A at positions 12, 24 and 27 is 2'-O-Methyl-2'-deoxyadenosine.

(ix) FEATURE:
  (D) OTHER INFORMATION: U at position 6 is 2'-fluoro-2'-deoxyuridine.

(ix) FEATURE:
  (D) OTHER INFORMATION: U at positions 22 and 34 is 2'-O-Methyl-2'-deoxyuridine.

(ix) FEATURE:
  (D) OTHER INFORMATION: Nucleotide 36 is an inverted orientation T (3'-3'-linked).

(xi) SEQUENCE DESCRIPTION: SEQ ID NO: 130:

CAGGCUACGG CACGUAGAGC AUCACCAUGA TCCUGT          36

(2) INFORMATION FOR SEQ ID NO: 131:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ix) FEATURE:
  (D) OTHER INFORMATION: C at positions 5, 8, 11, 23, 25, 26, 32 and 33 is 2'-O-Methyl-2'-deoxycytidine.

(ix) FEATURE:
  (D) OTHER INFORMATION: U at positions 6, 22 and 34 is 2'-O-Methyl-2'-deoxyuridine.

(ix) FEATURE:
  (D) OTHER INFORMATION: A at positions 7, 12, 24 and 27 is 2'-O-Methyl-2'-deoxyadenosine.

(ix) FEATURE:
            (D) OTHER INFORMATION:  G at positions 9, 10, and 35 is 2'-O-
                Methyl-2'-deoxyguanosine.

(ix) FEATURE:
            (D) OTHER INFORMATION:  Nucleotide 36 is an inverted
                orientation T (3'-3'-linked).

(xi) SEQUENCE DESCRIPTION: SEQ ID NO: 131:

CAGGCUACGG CACGTAGAGC AUCACCATGA TCCUGT                                        36

(2) INFORMATION FOR SEQ ID NO: 132:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ix) FEATURE:
            (D) OTHER INFORMATION:  C at positions 5, 8, 11, 23, 25, 26,
                32 and 33 is 2'-O-Methyl-2'-deoxycytidine.

(ix) FEATURE:
            (D) OTHER INFORMATION:  U at positions 6, 22 and 34 is 2'-O-
                Methyl-2'-deoxyuridine.

(ix) FEATURE:
            (D) OTHER INFORMATION:  A at positions 12, 18, 24 and 27 is
                2'-O-Methyl-2'-deoxyadenosine.

(ix) FEATURE:
            (D) OTHER INFORMATION:  G at positions 9, 10, and 35 is 2'-O-
                Methyl-2'-deoxyguanosine.

(ix) FEATURE:
            (D) OTHER INFORMATION:  Nucleotide 36 is an inverted
                orientation T (3'-3'-linked).

(xi) SEQUENCE DESCRIPTION: SEQ ID NO: 132:

CAGGCUACGG CACGTAGAGC AUCACCATGA TCCUGT                                        36

(2) INFORMATION FOR SEQ ID NO: 133:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ix) FEATURE:
            (D) OTHER INFORMATION:  C at positions 5, 8, 11, 23, 25, 26,
                32 and 33 is 2'-O-Methyl-2'-deoxycytidine.

(ix) FEATURE:
            (D) OTHER INFORMATION:  U at positions 6, 22 and 34 is 2'-O-
                Methyl-2'-deoxyuridine.

(ix) FEATURE:
            (D) OTHER INFORMATION:  G at positions 9, 10, 19 and 35 is 2'-
                O-Methyl-2'-deoxyguanosine.

(ix) FEATURE:
            (D) OTHER INFORMATION:  A at positions 12, 24 and 27 is 2'-O-
                Methyl-2'-deoxyadenosine.

(ix) FEATURE:
            (D) OTHER INFORMATION:  Nucleotide 36 is an inverted
                orientation T (3'-3'-linked).

(xi) SEQUENCE DESCRIPTION: SEQ ID NO: 133:

CAGGCUACGG CACGTAGAGC AUCACCATGA TCCUGT                                        36

(2) INFORMATION FOR SEQ ID NO: 134:

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION:  U at positions 6 and 22 is 2'-fluoro-
            2'-deoxyuridine.

(ix) FEATURE:
        (D) OTHER INFORMATION:  C at positions 8, 11, 25 and 26 is 2'-
            O-Methyl-2'-deoxycytidine.

(ix) FEATURE:
        (D) OTHER INFORMATION:  G at positions 9, 10, 19 and 35 is 2'-
            O-Methyl-2'-deoxyguanosine.

(ix) FEATURE:
        (D) OTHER INFORMATION:  A at positions 12, 24 and 27 is 2'-O-
            Methyl-2'-deoxyadenosine.

(ix) FEATURE:
        (D) OTHER INFORMATION:  C at positions 23, 32 and 33 is 2'-
            fluoro-2'-deoxycytidine.

(ix) FEATURE:
        (D) OTHER INFORMATION:  U at position 34 is 2'-O-Methyl-2'-
            deoxyuridine.

(ix) FEATURE:
        (D) OTHER INFORMATION:  Nucleotide 36 is an inverted
            orientation T (3'-3'-linked).

(xi) SEQUENCE DESCRIPTION: SEQ ID NO: 134:

CAGGCUACGG CACGTAGAGC AUCACCATGA TCCUGT                                     36

(2) INFORMATION FOR SEQ ID NO: 135:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION:  U at positions 6 and 22 is 2'-fluoro-
            2'-deoxyuridine.

(ix) FEATURE:
        (D) OTHER INFORMATION:  C at positions 8, 11, 20, 25 and 26 is
            2'-O-Methyl-2'-deoxycytidine.

(ix) FEATURE:
        (D) OTHER INFORMATION:  G at positions 9, 10, 19 and 35 is 2'-
            O-Methyl-2'-deoxyguanosine.

(ix) FEATURE:
        (D) OTHER INFORMATION:  A at positions 12, 24 and 27 is 2'-O-
            Methyl-2'-deoxyadenosine.

(ix) FEATURE:
        (D) OTHER INFORMATION:  C at positions 23, 32 and 33 is 2'-
            fluoro-2'-deoxycytidine.

(ix) FEATURE:
        (D) OTHER INFORMATION:  U at position 34 is 2'-O-Methyl-2'-
            deoxyuridine.

(ix) FEATURE:
        (D) OTHER INFORMATION:  Nucleotide 36 is an inverted
            orientation T (3'-3'-linked).

(xi) SEQUENCE DESCRIPTION: SEQ ID NO: 135:

CAGGCUACGG CACGTAGAGC AUCACCATGA TCCUGT                                     36
```

(2) INFORMATION FOR SEQ ID NO: 136:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION: U at positions 6 and 22 is 2'-fluoro-2'-deoxyuridine.

(ix) FEATURE:
        (D) OTHER INFORMATION: C at positions 8, 11, 20, 25 and 26 is 2'-O-Methyl-2'-deoxycytidine.

(ix) FEATURE:
        (D) OTHER INFORMATION: G at positions 9, 10, 17, 19 and 35 is 2'-O-Methyl-2'-deoxyguanosine.

(ix) FEATURE:
        (D) OTHER INFORMATION: A at positions 12, 24 and 27 is 2'-O-Methyl-2'-deoxyadenosine.

(ix) FEATURE:
        (D) OTHER INFORMATION: C at positions 23, 32 and 33 is 2'-fluoro-2'-deoxycytidine.

(ix) FEATURE:
        (D) OTHER INFORMATION: U at position 34 is 2'-O-Methyl-2'-deoxyuridine.

(ix) FEATURE:
        (D) OTHER INFORMATION: Nucleotide 36 is an inverted orientation T (3'-3'-linked).

(xi) SEQUENCE DESCRIPTION: SEQ ID NO: 136:

CAGGCUACGG CACGTAGAGC AUCACCATGA TCCUGT                    36

(2) INFORMATION FOR SEQ ID NO: 137:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION: U at positions 6 and 22 is 2'-fluoro-2'-deoxyuridine.

(ix) FEATURE:
        (D) OTHER INFORMATION: C at positions 8, 11, 25 and 26 is 2'-O-Methyl-2'-deoxycytidine.

(ix) FEATURE:
        (D) OTHER INFORMATION: G at positions 9, 10, 17, 19 and 35 is 2'-O-Methyl-2'-deoxyguanosine.

(ix) FEATURE:
        (D) OTHER INFORMATION: A at positions 12, 24 and 27 is 2'-O-Methyl-2'-deoxyadenosine.

(ix) FEATURE:
        (D) OTHER INFORMATION: C at positions 23, 32 and 33 is 2'-fluoro-2'-deoxycytidine.

(ix) FEATURE:
        (D) OTHER INFORMATION: U at position 34 is 2'-O-Methyl-2'-deoxyuridine.

(ix) FEATURE:
        (D) OTHER INFORMATION: Nucleotide 36 is an inverted orientation T (3'-3'-linked).

(xi) SEQUENCE DESCRIPTION: SEQ ID NO: 137:

CAGGCUACGG CACGTAGAGC AUCACCATGA TCCUGT                36

(2) INFORMATION FOR SEQ ID NO: 138:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION: U at positions 6 and 22 is 2'-fluoro-
            2'-deoxyuridine.

(ix) FEATURE:
        (D) OTHER INFORMATION: A at positions 7, 12, 24 and 27 is 2'-
            O-Methyl-2'-deoxyadenosine.

(ix) FEATURE:
        (D) OTHER INFORMATION: C at positions 8, 11, 25 and 26 is 2'-
            O-Methyl-2'-deoxycytidine.

(ix) FEATURE:
        (D) OTHER INFORMATION: G at positions 9, 10, 17, 19 and 35 is
            2'-O-Methyl-2'-deoxyguanosine.

(ix) FEATURE:
        (D) OTHER INFORMATION: C at positions 23, 32 and 33 is 2'-
            fluoro-2'-deoxycytidine.

(ix) FEATURE:
        (D) OTHER INFORMATION: U at position 34 is 2'-O-Methyl-2'-
            deoxyuridine.

(ix) FEATURE:
        (D) OTHER INFORMATION: Nucleotide 36 is an inverted
            orientation T (3'-3'-linked).

(xi) SEQUENCE DESCRIPTION: SEQ ID NO: 138:

CAGGCUACGG CACGTAGAGC AUCACCATGA TCCUGT                36

(2) INFORMATION FOR SEQ ID NO: 139:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
        (D) OTHER INFORMATION: U at positions 6 and 20 is 2'-fluoro-
            2'-deoxyuridine.

(ix) FEATURE:
        (D) OTHER INFORMATION: C at position 8 is 2'-O-Methyl-2'-
            deoxycytidine.

(ix) FEATURE:
        (D) OTHER INFORMATION: G at positions 9, 17, and 31 is 2'-O-
            Methyl-2'-deoxyguanosine.

(ix) FEATURE:
        (D) OTHER INFORMATION: S at positions 10 and 23 is a
            hexaethyleneglycol spacer.

(ix) FEATURE:
        (D) OTHER INFORMATION: C at positions 21, 28 and 29 is 2'-
            fluoro-2'-deoxycytidine.

(ix) FEATURE:
        (D) OTHER INFORMATION: A at position 22 is 2'-O-Methyl-2'-
            deoxyadenosine.

(ix) FEATURE:
        (D) OTHER INFORMATION: U at position 30 is 2'-O-Methyl-2'-
            deoxyuridine.

(ix) FEATURE:
        (D) OTHER INFORMATION:  Nucleotide 32 is an inverted
            orientation T (3'-3'-linked).

(xi) SEQUENCE DESCRIPTION: SEQ ID NO: 139:

CAGGCUACGS CGTAGAGCAU CASTGATCCU GT                                      32

(2) INFORMATION FOR SEQ ID NO: 140:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
        (D) OTHER INFORMATION:  U at positions 6 and 20 is 2'-fluoro-
            2'-deoxyuridine.

(ix) FEATURE:
        (D) OTHER INFORMATION:  C at position 8 is 2'-O-Methyl-2'-
            deoxycytidine.

(ix) FEATURE:
        (D) OTHER INFORMATION:  G at positions 9, 15, 17, and 31 is
            2'-O-Methyl-2'-deoxyguanosine.

(ix) FEATURE:
        (D) OTHER INFORMATION:  S at positions 10 and 23 is a
            hexaethyleneglycol spacer.

(ix) FEATURE:
        (D) OTHER INFORMATION:  C at positions 21, 28 and 29 is 2'-
            fluoro-2'-deoxycytidine.

(ix) FEATURE:
        (D) OTHER INFORMATION:  A at position 22 is 2'-O-Methyl-2'-
            deoxyadenosine.

(ix) FEATURE:
        (D) OTHER INFORMATION:  U at position 30 is 2'-O-Methyl-2'-
            deoxyuridine.

(ix) FEATURE:
        (D) OTHER INFORMATION:  Nucleotide 32 is an inverted
            orientation T (3'-3'-linked).

(xi) SEQUENCE DESCRIPTION: SEQ ID NO: 140:

CAGGCUACGS CGTAGAGCAU CASTGATCCU GT                                      32

(2) INFORMATION FOR SEQ ID NO: 141:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (D) OTHER INFORMATION:  Nucleotide 36 is an inverted
            orientation T (3'-3'-linked).

(xi) SEQUENCE DESCRIPTION: SEQ ID NO: 141:

CAGGCTACGG CACGTAGAGC ATCACCATGA TCCTGT                                  36

(2) INFORMATION FOR SEQ ID NO: 142:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:

```
            (D) OTHER INFORMATION: U at positions 6, 20 and 30 is 2'-
                fluoro-2'-deoxyuridine.

(ix) FEATURE:
            (D) OTHER INFORMATION: C at positions 8, 21, 28 and 29 is 2'-
                fluoro-2'-deoxycytidine.

(ix) FEATURE:
            (D) OTHER INFORMATION: G at positions 9, 15, 17, and 31 is
                2'-O-Methyl-2'-deoxyguanosine.

(ix) FEATURE:
            (D) OTHER INFORMATION: S at positions 10 and 23 is a
                hexaethyleneglycol spacer.

(ix) FEATURE:
            (D) OTHER INFORMATION: A at position 22 is 2'-O-Methyl-2'-
                deoxyadenosine.

(ix) FEATURE:
            (D) OTHER INFORMATION: Nucleotide 32 is an inverted
                orientation T (3'-3'-linked).

(xi) SEQUENCE DESCRIPTION: SEQ ID NO: 142:

CAGGCUACGS CGTAGAGCAU CASTGATCCU GT                                     32

(2) INFORMATION FOR SEQ ID NO: 143:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ix) FEATURE:
            (D) OTHER INFORMATION: U at positions 6, 20 and 30 is 2'-
                fluoro-2'-deoxyuridine.

(ix) FEATURE:
            (D) OTHER INFORMATION: C at positions 8, 21, 28 and 29 is 2'-
                fluoro-2'-deoxycytidine.

(ix) FEATURE:
            (D) OTHER INFORMATION: G at positions 9, 15, 17, and 31 is
                2'-O-Methyl-2'-deoxyguanosine.

(ix) FEATURE:
            (D) OTHER INFORMATION: N at positions 10 and 23 is a
                hexaethyleneglycol spacer.

(ix) FEATURE:
            (D) OTHER INFORMATION: A at position 22 is 2'-O-Methyl-2'-
                deoxyadenosine.

(ix) FEATURE:
            (D) OTHER INFORMATION: Nucleotide 32 is an inverted
                orientation T (3'-3'-linked).

(xi) SEQUENCE DESCRIPTION: SEQ ID NO: 143:

CAGGCUACGN CGTAGAGCAU CANTGATCCU GT                                     32

(2) INFORMATION FOR SEQ ID NO: 144:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ix) FEATURE:
            (D) OTHER INFORMATION: G at positions 3, 4, 12, and 25 is 2'-
                O-Methyl-2'-deoxyguanosine.

(ix) FEATURE:
            (D) OTHER INFORMATION: U at positions 6, 20 and 27 is 2'-
                fluoro-2'-deoxyuridine.
```

(ix) FEATURE:
            (D) OTHER INFORMATION:  N at positions 10 and 23 is a
                hexaethyleneglycol spacer.

(ix) FEATURE:
            (D) OTHER INFORMATION:  C at positions 11, 18, 21 and 29 is
                2'-fluoro-2'-deoxycytidine.

(ix) FEATURE:
            (D) OTHER INFORMATION:  A at position 16 is 2'-O-Methyl-2'-
                deoxyadenosine.

(ix) FEATURE:
            (D) OTHER INFORMATION:  Nucleotide 32 is an inverted
                orientation T (3'-3'-linked).

(xi) SEQUENCE DESCRIPTION: SEQ ID NO: 144:

CAGGCUACGN CGTAGAGCAU CANTGAUCCT GT                                         32

(2) INFORMATION FOR SEQ ID NO: 145:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
        (D) OTHER INFORMATION:  C at positions 4, 8, 21 and 29 is 2'-
            fluoro-2'-deoxycytidine.

(ix) FEATURE:
        (D) OTHER INFORMATION:  U at positions 6, 20 and 30 is 2'-
            fluoro-2'-deoxyuridine.

(ix) FEATURE:
        (D) OTHER INFORMATION:  G at positions 5, 9, 17, and 31 is 2'-
            O-Methyl-2'-deoxyguanosine.

(ix) FEATURE:
        (D) OTHER INFORMATION:  A at position 22 is 2'-O-Methyl-2'-
            deoxyadenosine.

(ix) FEATURE:
        (D) OTHER INFORMATION:  N at positions 10 and 23 is a
            hexaethylene glycol phosphoramidite.

(ix) FEATURE:
        (D) OTHER INFORMATION:  Nucleotide 32 is an inverted
            orientation T (3'-3'-linked).

(xi) SEQUENCE DESCRIPTION: SEQ ID NO: 145:

CAGCGUACGN CGTACCGATU CANTGAAGCU GT                                         32

(2) INFORMATION FOR SEQ ID NO: 146:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
        (D) OTHER INFORMATION:  U at positions 6, 20 and 30 is 2'-
            fluoro-2'-deoxyuridine.

(ix) FEATURE:
        (D) OTHER INFORMATION:  C at positions 8, 21, 28, and 29 is
            2'-fluoro-2'-deoxycytidine.

(ix) FEATURE:
        (D) OTHER INFORMATION:  G at positions 9, 15, 17, and 31 is
            2'-O-Methyl-2'-deoxyguanosine.

(ix) FEATURE:

(D) OTHER INFORMATION:  A at position 22 is 2'-O-Methyl-2'-
                    deoxyadenosine.

(ix) FEATURE:
                (D) OTHER INFORMATION:  N at positions 10 and 23 is a
                    hexaethylene glycol phosphoramidite.

(ix) FEATURE:
                (D) OTHER INFORMATION:  Nucleotide 32 is an inverted
                    orientation T (3'-3'-linked).

(xi) SEQUENCE DESCRIPTION: SEQ ID NO: 146:

CAGGCUACGN CGTAGAGCAU CANTGATCCU GT                                         32

(2) INFORMATION FOR SEQ ID NO: 147:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (ix) FEATURE:
                (D) OTHER INFORMATION:  C at positions 4, 8, 21 and 29 is 2'-
                    fluoro-2'-deoxycytidine.

(ix) FEATURE:
                (D) OTHER INFORMATION:  U at positions 6, 20 and 30 is 2'-
                    fluoro-2'-deoxyuridine.

(ix) FEATURE:
                (D) OTHER INFORMATION:  G at positions 5, 9, 17, and 31 is 2'-
                    O-Methyl-2'-deoxyguanosine.

(ix) FEATURE:
                (D) OTHER INFORMATION:  A at position 22 is 2'-O-Methyl-2'-
                    deoxyadenosine.

(ix) FEATURE:
                (D) OTHER INFORMATION:  N at positions 10 and 23 is a
                    hexaethylene glycol phosphoramidite.

(ix) FEATURE:
                (D) OTHER INFORMATION:  Nucleotide 32 is an inverted
                    orientation T (3'-3'-linked).

(xi) SEQUENCE DESCRIPTION: SEQ ID NO: 147:

CAGCGUACGN CGTACCGATU CANTGAAGCU GT                                         32

(2) INFORMATION FOR SEQ ID NO: 148:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (ix) FEATURE:
                (D) OTHER INFORMATION:  U at positions 6, 20 and 30 is 2'-
                    fluoro-2'-deoxyuridine.

(ix) FEATURE:
                (D) OTHER INFORMATION:  C at positions 8, 21, 28 and 29 is 2'-
                    fluoro-2'-deoxycytidine.

(ix) FEATURE:
                (D) OTHER INFORMATION:  G at positions 9, 15, 17, and 31 is
                    2'-O-Methyl-2'-deoxyguanosine.

(ix) FEATURE:
                (D) OTHER INFORMATION:  S at positions 10 and 23 is a
                    hexaethyleneglycol spacer.

(ix) FEATURE:
                (D) OTHER INFORMATION:  A at position 22 is 2'-O-Methyl-2'-
                    deoxyadenosine.

```
            (ix) FEATURE:
                 (D) OTHER INFORMATION:  Nucleotide 32 is an inverted
                     orientation T (3'-3'-linked).

(xi) SEQUENCE DESCRIPTION: SEQ ID NO: 148:

CAGGCUACGS CGTAGAGCAU CASTGATCCU GT                                32

(2) INFORMATION FOR SEQ ID NO: 149:

(i) SEQUENCE CHARACTERISTICS:
                 (A) LENGTH: 32 base pairs
                 (B) TYPE: nucleic acid
                 (C) STRANDEDNESS: single
                 (D) TOPOLOGY: linear (ix) FEATURE:
                 (D) OTHER INFORMATION:  C at positions 4, 8, 21 and 29 is 2'-
                     fluoro-2'-deoxycytidine.

(ix) FEATURE:
                 (D) OTHER INFORMATION:  G at positions 5, 9, 17, and 31 is 2'-
                     O-Methyl-2'-deoxyguanosine.

(ix) FEATURE:
                 (D) OTHER INFORMATION:  U at positions 6, 20 and 30 is 2'-
                     fluoro-2'-deoxyuridine.

(ix) FEATURE:
                 (D) OTHER INFORMATION:  N at positions 10 and 23 is a
                     hexaethyleneglycol spacer.

(ix) FEATURE:
                 (D) OTHER INFORMATION:  A at position 22 is 2'-O-Methyl-2'-
                     deoxyadenosine.

(ix) FEATURE:
                 (D) OTHER INFORMATION:  Nucleotide 32 is an inverted
                     orientation T (3'-3'-linked).

(xi) SEQUENCE DESCRIPTION: SEQ ID NO: 149:

CAGCGUACGN CGTACCGATU CANTGAAGCU GT                                32
```

We claim:

1. A complex comprising a platelet derived growth factor (PDGF) nucleic acid ligand of SEQ ID NO:146 and a non-immunogenic, high molecular weight compound, wherein N at positions 10 and 23 of SEQ ID NO:146 is

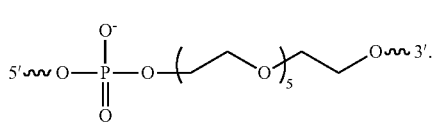

2. The complex of claim 1, wherein the non-immunogenic, high molecular weight compound is a polyalkylene glycol.

3. The complex of claim 2, having one or more polyalkylene glycols.

4. The complex of claim 3, wherein each of the one or more polyalkylene glycols is polyethylene glycol.

5. The complex of claim 4, wherein the polyethylene glycol has a molecular weight of about 10-80K.

6. The complex of claim 5, wherein the polyethylene glycol has a molecular weight of about 20-45K.

7. The complex of claim 3, wherein the one or more polyalkylene glycols are two 20K polyethylene glycols.

8. The complex of claim 1, wherein the non-immunogenic, high molecular weight compound is attached to the PDGF nucleic acid ligand via a linker.

9. The complex of claim 7, wherein the two 20K polyethylene glycols are attached to the PDGF nucleic acid ligand via a linker.

10. The complex of claim 9, wherein formation of the linker comprises conjugating the following compound

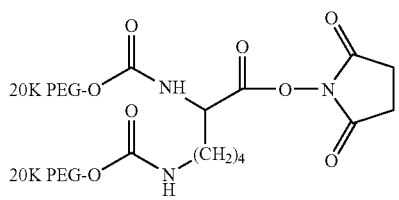

to a 5' primary amino group of an aminolinker on the 5'-end of the PDGF nucleic acid ligand.

11. A complex having the structure A-B-Y, wherein A is one or more polyalkylene glycols, B is a linker, and Y is a PDGF nucleic acid ligand of SEQ ID NO:146, wherein N at positions 10 and 23 of SEQ ID NO:146 is

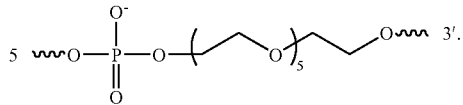

12. The complex of claim 11, wherein each of the one or more polyalkylene glycols is polyethylene glycol.

13. The complex of claim 12, wherein the polyethylene glycol has a molecular weight of about 10-80 K.

14. The complex of claim 12, wherein the polyethylene glycol has a molecular weight of about 20-45K.

15. The complex of claim 11, wherein the one or more polyalkylene glycols are two 20K polyethylene glycols.

16. The complex of claim 11, wherein each of the one or more polyalkylene glycols (A) is attached to the spacer (B) via a linker.

17. A complex comprising a non-immunogenic, high molecular weight compound and a platelet derived growth factor (PDGF) nucleic acid ligand, wherein the nucleic acid ligand has the structure:

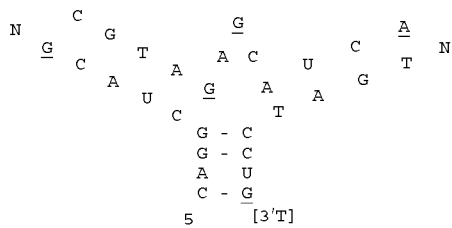

in which the N is

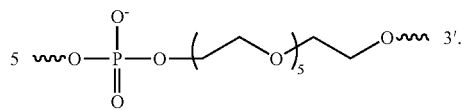

18. The complex of claim 17, wherein the non-immunogenic, high molecular weight compound is a polyalkylene glycol.

19. The complex of claim 18, having one or more polyalkylene glycols.

20. The complex of claim 19, wherein each of the one or more polyalkylene glycols is polyethylene glycol.

21. The complex of claim 20, wherein the polyethylene glycol has a molecular weight of about 10-80K.

22. The complex of claim 20, wherein the polyethylene glycol has a molecular weight of about 20-45K.

23. The complex of claim 19, wherein the one or more polyalkylene glycols are two 20K polyethylene glycols.

24. The complex of claim 17, wherein the non-immunogenic, high molecular weight compound is attached to the PDGF nucleic acid ligand via a linker.

25. The complex of claim 23, wherein the two 20K polyethylene glycols are attached to the PDGF nucleic acid ligand via a linker.

26. The complex of claim 25, wherein formation of the linker comprises conjugating the following compound

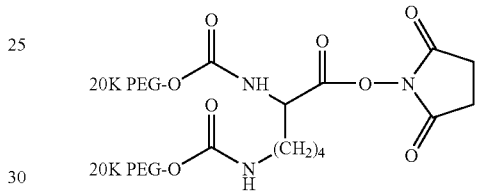

to a primary amino group of an aminolinker on the 5'-end of the PDGF nucleic acid ligand.

* * * * *

UNITED STATES PATENT AND TRADEMARK OFFICE
CERTIFICATE OF CORRECTION

PATENT NO. : 7,939,654 B2
APPLICATION NO. : 12/512780
DATED : May 10, 2011
INVENTOR(S) : Nebojsa Janjic and Larry Gold It is certified that error appears in the above-identified patent and that said Letters Patent is hereby corrected as shown below:

At column 143, line 5, the word "from" was mistakenly omitted between the words "is" and "a" and should have been included as indicated below for line 5:

(D) OTHER INFORMATION: N at positions 10 and 23 is from a

At column 145, line 45, the word "from" is missing after "is" and should have been included as indicated below for line 45:

at positions 10 and 23 of SEQ ID NO: 146 is from

At column 146, line 59, the word "from" is missing after "is" and should have been included as indicated below for line 59:

positions 10 and 23 of SEQ ID NO: 146 is from

At column 147, line 29, the word "from" is missing after "is" and should have been included as indicated below for line 29:

in which the N is from

Signed and Sealed this
Eleventh Day of October, 2011

David J. Kappos
*Director of the United States Patent and Trademark Office*